US012570727B2

(12) United States Patent
Li et al.

(10) Patent No.: US 12,570,727 B2
(45) Date of Patent: Mar. 10, 2026

(54) **ANTIBODIES SPECIFICALLY RECOGNIZING *PSEUDOMONAS* Psl AND USES THEREOF**

(71) Applicant: Beijing Solobio Genetechnology Co., Ltd., Beijing (CN)

(72) Inventors: Zhong Li, Beijing (CN); Maorong Yu, Beijing (CN)

(73) Assignee: Beijing Solobio Genetechnology Co., Ltd., Beijing (CN)

( * ) Notice: Subject to any disclaimer, the term of this patent is extended or adjusted under 35 U.S.C. 154(b) by 546 days.

(21) Appl. No.: 18/020,180

(22) PCT Filed: Aug. 4, 2021

(86) PCT No.: PCT/CN2021/110429
§ 371 (c)(1),
(2) Date: Feb. 7, 2023

(87) PCT Pub. No.: WO2022/028444
PCT Pub. Date: Feb. 10, 2022

(65) Prior Publication Data
US 2023/0295279 A1 Sep. 21, 2023

(30) Foreign Application Priority Data
Aug. 7, 2020 (WO) ................ PCT/CN2020/107666

(51) Int. Cl.
| | |
|---|---|
| *C07K 16/00* | (2006.01) |
| *A61P 31/04* | (2006.01) |
| *C07H 21/04* | (2006.01) |
| *C07K 16/1214* | (2026.01) |
| *C12N 1/12* | (2006.01) |
| *C12N 5/06* | (2006.01) |
| *C12N 15/85* | (2006.01) |
| *C12P 21/04* | (2006.01) |
| *C12P 21/06* | (2006.01) |
| *C07K 1/00* | (2006.01) |

(52) U.S. Cl.
CPC .......... *C07K 16/1214* (2013.01); *A61P 31/04* (2018.01); *C12N 15/85* (2013.01); *C12N 2800/107* (2013.01)

(58) Field of Classification Search
None
See application file for complete search history.

(56) References Cited

U.S. PATENT DOCUMENTS

| | | |
|---|---|---|
| 2015/0023966 A1 | 1/2015 | Digiandomenico et al. |
| 2016/0297872 A1 | 10/2016 | DiGiandomenico et al. |

FOREIGN PATENT DOCUMENTS

| | | |
|---|---|---|
| CN | 103974975 A | 8/2014 |
| CN | 104136042 A | 11/2014 |
| CN | 104995209 A | 10/2015 |
| JP | 2014519334 A | 8/2014 |
| JP | 2015504421 A | 2/2015 |
| JP | 2015535005 A | 12/2015 |
| WO | WO2012170807 A2 | 12/2012 |
| WO | WO2013070615 A1 | 5/2013 |

OTHER PUBLICATIONS

Rudikoff et al., Single amino acid substitution altering antigen-binding specificity, Proc. Natl. Acad. Sci. USA, Mar. 1982, vol. 79, p. 1979-1983.

Brown et al., Tolerance of single, but not multiple, amino acid replacements in antibody VH CDR 2: a means of minimizing B cell wastage from somatic hypermutation?, The Journal of Immunology, Feb. 1996, vol. 156, p. 3285-3291.

Digiandomenico et al., Identification of broadly protective human antibodies to Pseudomonas aeruginosa exopolysaccharide Psl by phenotypic screening, The Journal of Experimental Medicine, 2012, vol. 209, No. 7, p. 1273-1287.

Guan et al., Screening and activity verification of monoclonal antibody against PcrV protein of pseudomonas aeruginosa, Chinese Journal of Immunology, 2018, vol. 34, No. 2, p. 233-238, and its English abstract.

*Primary Examiner* — Chun W Dahle

(74) *Attorney, Agent, or Firm* — Bret E. Field; Bozicevic, Field & Francis LLP

(57) ABSTRACT

Provided herein are antibodies including antigen-binding fragments thereof that specifically recognizing *Pseudomonas* Psl. Also provided are methods of making and using these antibodies.

9 Claims, 16 Drawing Sheets

Specification includes a Sequence Listing.

SEQUENCE LISTING

```
<160> NUMBER OF SEQ ID NOS: 214

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

Ser Ser Gly Asp Tyr Trp Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct

<400> SEQUENCE: 2

Ser Thr Ser Tyr Trp Ala
1               5
```

-continued

```
<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Ser Asp Ser Tyr Trp Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Ile His Ser Val His
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Asp Tyr Tyr Trp Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Ser Asp Tyr Trp Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Ser Thr Ser Tyr Trp
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Ser Gly Tyr Tyr Trp Ser
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Ser Gly Ser Tyr Tyr Trp Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Ser Ser Asp Tyr Tyr Trp Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Ser Ser Ser Ser Tyr Trp Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Gly Thr Tyr Val His
1               5

<210> SEQ ID NO 13
<211> LENGTH: 16
<212> TYPE: PRT
<213> ORGANISM: Artificial Sequence
<220> FEATURE:
<223> OTHER INFORMATION: Synthetic Construct

<400> SEQUENCE: 13

Ser Ile His Asn Gln Gly Ser Thr Tyr Tyr Asn Pro Ser Leu Lys Gly
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic Construct

<400> SEQUENCE: 14

Thr Ile Tyr Tyr Asp Gly Tyr Thr Phe Tyr Asn Pro Ser Leu Lys Ser
1               5                   10                  15

<210> SEQ ID NO 15
```

```
<211> LENGTH: 16
<212> TYPE: PRT
<213> ORGANISM: Artificial Sequence
<220> FEATURE:
<223> OTHER INFORMATION: Synthetic Construct

<400> SEQUENCE: 15

Thr Ile Tyr Tyr Asp Gly Thr Thr Phe Tyr Asn Pro Ser Leu Arg Ser
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Thr Ile Ile Ser Ser Gly Thr Thr Thr Thr Tyr Ala Gln Ser Phe Gln
1               5                   10                  15

Asp

<210> SEQ ID NO 17
<211> LENGTH: 16
<212> TYPE: PRT
<213> ORGANISM: Artificial Sequence
<220> FEATURE:
<223> OTHER INFORMATION: Synthetic Construct

<400> SEQUENCE: 17

Tyr Ile His Ser Ser Gly Ser Thr Asp Tyr Asn Pro Ser Leu Lys Ser
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct

<400> SEQUENCE: 18

Tyr Ile Ser Asp Ser Gly Ser Thr Asp Tyr Asn Pro Ser Leu Lys Ser
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic Construct

<400> SEQUENCE: 19

Ser Ile His His Ser Gly Ser Thr Tyr Tyr Asn Pro Ser Leu Gln Ser
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic Construct

<400> SEQUENCE: 20

Phe Ile His Asn Asn Gly Tyr Thr Asn Tyr Asn Pro Ser Leu Lys Ser
1               5                   10                  15
```

<210> SEQ ID NO 21
<211> LENGTH: 16
<212> TYPE: PRT
<213> ORGANISM: Artificial Sequence
<220> FEATURE:
<223> OTHER INFORMATION: Synthetic Construct

<400> SEQUENCE: 21

Ser Ile Asn Tyr Ala Gly Ser Thr Tyr Tyr Asn Pro Ser Leu Lys Ser
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic Construct

<400> SEQUENCE: 22

Ser Ile Tyr Asp Asp Gly Thr Thr Phe Tyr Asn Pro Ser Phe Lys Ser
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: Synthetic Construct

<400> SEQUENCE: 23

Trp Ile Asp Arg Asn Arg Gly Gly Thr Asn Tyr Ala Gln Lys Phe Gln
1               5                   10                  15

Gly

<210> SEQ ID NO 24
<211> LENGTH: 13
<212> TYPE: PRT
<213> ORGANISM: Artificial Sequence
<220> FEATURE:
<223> OTHER INFORMATION: Synthetic Construct

<400> SEQUENCE: 24

Gln Phe Gly Ser Glu Thr Tyr Tyr Thr Gly Ile Asp Pro
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic Construct

<400> SEQUENCE: 25

His Asp Ser Gly Gln Gln Leu Ile Asn Asn Trp Phe Asp Pro
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

His Glu Ser Gly Gln Gln Leu Val Asn Asn Trp Phe Asp Pro
1               5                   10

<210> SEQ ID NO 27
<211> LENGTH: 4
<212> TYPE: PRT
<213> ORGANISM: Artificial Sequence
<220> FEATURE:
<223> OTHER INFORMATION: Synthetic Construct

<400> SEQUENCE: 27

Asp Gly Asp Ser
1

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Ala Gln Gly Gly Ser Arg Arg Thr Leu Asp Tyr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Ala Thr Val Thr Thr Tyr Ser Phe Asp Tyr
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Ala Glu Tyr Tyr Tyr Glu Ser Ser Gly Pro Leu Phe Asp Tyr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct

<400> SEQUENCE: 31

Gly Glu Thr Tyr Glu Ser Ser Gly Tyr Tyr Asp Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Gln Asn Thr Ala Arg Gly Ile Ser Thr Asp Phe
1               5                   10

-continued

```
<210> SEQ ID NO 33
<211> LENGTH: 13
<212> TYPE: PRT
<213> ORGANISM: Artificial Sequence
<220> FEATURE:
<223> OTHER INFORMATION: Synthetic Construct

<400> SEQUENCE: 33

Thr Pro Tyr Gly Asp Tyr Ala Ser Tyr Phe Phe Asp Tyr
1               5                   10

<210> SEQ ID NO 34
<211> LENGTH: 3
<212> TYPE: PRT
<213> ORGANISM: Artificial Sequence
<220> FEATURE:
<223> OTHER INFORMATION: Synthetic Construct

<400> SEQUENCE: 34

Asp Pro Gly
1

<210> SEQ ID NO 35
<211> LENGTH: 4
<212> TYPE: PRT
<213> ORGANISM: Artificial Sequence
<220> FEATURE:
<223> OTHER INFORMATION: Synthetic Construct

<400> SEQUENCE: 35

Asp Gly Thr Ser
1

<210> SEQ ID NO 36
<211> LENGTH: 13
<212> TYPE: PRT
<213> ORGANISM: Artificial Sequence
<220> FEATURE:
<223> OTHER INFORMATION: Synthetic Construct

<400> SEQUENCE: 36

Gln Phe Gly Ser Glu Thr Tyr Tyr Asn Gly Ile Gln Pro
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Synthetic Construct

<400> SEQUENCE: 37

Arg Ser Ser Gln Ser Leu Leu His Ser Asn Gly Tyr Asn Tyr Leu Asp
1               5                   10                  15

<210> SEQ ID NO 38
<211> LENGTH: 11
<212> TYPE: PRT
<213> ORGANISM: Artificial Sequence
<220> FEATURE:
<223> OTHER INFORMATION: Synthetic Construct

<400> SEQUENCE: 38

Arg Ala Ser Gln Ser Ile Gly Tyr Tyr Leu Asn
1               5                   10

<210> SEQ ID NO 39
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 39

Arg Ala Ser Gln Ser Val Ser Ser Asn Leu Ala
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic Construct

<400> SEQUENCE: 40

Arg Ala Ser Gln Gly Ile Ser Ser Trp Leu Ala
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Construct

<400> SEQUENCE: 41

Arg Ala Ser Gln Thr Ile Ser Ser Tyr Leu Asn
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

Arg Ala Ser Gln Gly Ile Asn Arg Trp Leu Ala
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct

<400> SEQUENCE: 43

Arg Ala Ser Gln Gly Ile Ser Ser Tyr Leu Ala
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic Construct

<400> SEQUENCE: 44

Gln Ala Ser Gln Asp Ile Ser Asn Ser Leu Asn
1               5                   10

<210> SEQ ID NO 45
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 45

Arg Ala Ser Gln Ser Ile Ser Ser Tyr Leu Asn
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Arg Ala Ser Gln Ser Ile Gly Arg Tyr Leu Asn
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic Construct

<400> SEQUENCE: 47

Arg Ala Ser Gln Ser Val Ser Ser Ser Tyr Leu Ala
1               5                   10

<210> SEQ ID NO 48
<211> LENGTH: 16
<212> TYPE: PRT
<213> ORGANISM: Artificial Sequence
<220> FEATURE:
<223> OTHER INFORMATION: Synthetic Construct

<400> SEQUENCE: 48

Lys Ser Ser Gln Ser Leu Leu His Ser Asp Gly Lys Thr Tyr Leu Tyr
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic Construct

<400> SEQUENCE: 49

Arg Ser Ser Gln Ser Leu Leu His Ser Asn Gly Asn Asn Tyr Leu Asp
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic Construct

<400> SEQUENCE: 50

Arg Ser Ser Gln Ser Leu Leu His Ser Arg Gly Tyr Asn Tyr Leu Asp
1               5                   10                  15

<210> SEQ ID NO 51
<211> LENGTH: 7
<212> TYPE: PRT
```

-continued

<213> ORGANISM: Artificial Sequence
<220> FEATURE:
<223> OTHER INFORMATION: Synthetic Construct

<400> SEQUENCE: 51

Leu Gly Ser Asn Arg Ala Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Ala Ala Ser Ser Leu Gln Ser
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Gly Ala Ser Thr Arg Ala Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

His Ala Ser Thr Leu Glu Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic Construct

<400> SEQUENCE: 55

Ala Thr Ser Thr Leu Gln Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct

<400> SEQUENCE: 56

Ala Ala Ser Arg Leu Gln Ser
1               5

<210> SEQ ID NO 57
<211> LENGTH: 7
<212> TYPE: PRT
<213> ORGANISM: Artificial Sequence

```
<220> FEATURE:
<223> OTHER INFORMATION: Synthetic Construct

<400> SEQUENCE: 57

Asp Ala Ser Asn Leu Glu Thr
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct

<400> SEQUENCE: 58

Thr Ala Ser Asn Leu Gln Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic Construct

<400> SEQUENCE: 59

Gly Ala Ser Ser Arg Ala Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic Construct

<400> SEQUENCE: 60

Glu Val Ser Asn Arg Phe Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct

<400> SEQUENCE: 61

Met Gly Ser Asn Arg Ala Ser
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct

<400> SEQUENCE: 62

Met Gln Ala Leu Gln Thr Pro Tyr Thr
1               5

<210> SEQ ID NO 63
<211> LENGTH: 9
<212> TYPE: PRT
<213> ORGANISM: Artificial Sequence
<220> FEATURE:
```

-continued

```
<223> OTHER INFORMATION: Synthetic Construct

<400> SEQUENCE: 63

Gln Gln Ser Tyr Thr Ile Pro Tyr Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic Construct

<400> SEQUENCE: 64

Gln Gln Ser Gly Asp Ser Leu Val Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Leu Gln Ala Asn Ser Leu Pro His Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Gln Gln Ser Tyr Ser Thr Pro Tyr Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Gln Gln Gly Tyr Thr Leu Pro Pro Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Gln Gln Ser Phe Ser Val Pro Ile Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 69

Met Gln Ala Leu Gln Thr Pro Arg Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Construct

<400> SEQUENCE: 70

Gln Gln Ser Tyr Thr Ala Pro Tyr Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct

<400> SEQUENCE: 71

Gln Gln Ser Tyr Asp Ser Pro Leu Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Construct

<400> SEQUENCE: 72

Gln Gln Ala Asn Ser Leu Pro Phe Thr
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Construct

<400> SEQUENCE: 73

Gln His Tyr Asp Asn Ser Leu Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Construct

<400> SEQUENCE: 74

Met Gln Ser Leu Gln Leu Pro Leu Thr
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic Construct

<400> SEQUENCE: 75

Met Gln Gly Leu Gln Thr Pro Leu Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Construct

<400> SEQUENCE: 76

Leu Gln Ala Phe Ser Leu Pro His Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Construct

<400> SEQUENCE: 77

Leu Gln Ala Ser Ser Leu Pro His Thr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Construct

<400> SEQUENCE: 78

Leu Gln Ala Lys Ser Leu Pro His Thr
1               5

<210> SEQ ID NO 79
<211> LENGTH: 123
<212> TYPE: PRT
<213> ORGANISM: Artificial Sequence
<220> FEATURE:
<223> OTHER INFORMATION: Synthetic Construct

<400> SEQUENCE: 79

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Gln Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Thr Gly Ile Asp Pro
            100                 105                 110

Trp Gly Gln Gly Thr Leu Val Thr Val Ser Ser
        115                 120

```
<210> SEQ ID NO 80
<211> LENGTH: 123
<212> TYPE: PRT
<213> ORGANISM: Artificial Sequence
<220> FEATURE:
<223> OTHER INFORMATION: Synthetic Construct

<400> SEQUENCE: 80

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser Tyr Trp Ala Trp Ile Arg Gln Pro Pro Gly Lys Gly Leu Glu Trp
        35                  40                  45

Ile Gly Thr Ile Tyr Tyr Asp Gly Tyr Thr Phe Tyr Asn Pro Ser Leu
    50                  55                  60

Lys Ser Arg Val Thr Ile Ser Gly Asp Thr Ser Lys Arg Gln Tyr Phe
65                  70                  75                  80

Leu Arg Leu Ser Ser Val Thr Ala Ala Asp Thr Ala Val Tyr Tyr Cys
                85                  90                  95

Ala Arg His Asp Ser Gly Gln Gln Leu Ile Asn Asn Trp Phe Asp Pro
            100                 105                 110

Trp Gly Gln Gly Thr Val Val Thr Val Ser Ser
        115                 120

<210> SEQ ID NO 81
<211> LENGTH: 123
<212> TYPE: PRT
<213> ORGANISM: Artificial Sequence
<220> FEATURE:
<223> OTHER INFORMATION: Synthetic Construct

<400> SEQUENCE: 81

Gln Val Gln Leu Gln Glu Ser Gly Pro Gly Leu Val Lys Ser Ser Glu
1               5                   10                  15

Thr Leu Ser Leu Thr Cys Thr Val Ser Gly Asp Ser Ile Ser Ser Asp
            20                  25                  30

Ser Tyr Trp Gly Trp Ile Arg Gln Pro Pro Gly Lys Gly Leu Glu Trp
        35                  40                  45

Leu Ala Thr Ile Tyr Tyr Asp Gly Thr Thr Phe Tyr Asn Pro Ser Leu
    50                  55                  60

Arg Ser Arg Leu Ile Ile Ser Gly Asp Ala Ser Lys Lys Gln Phe Ser
65                  70                  75                  80

Leu Arg Leu Ser Ser Val Thr Ala Ala Asp Thr Ala Ile Tyr Tyr Cys
                85                  90                  95

Ala Arg His Glu Ser Gly Gln Gln Leu Val Asn Asn Trp Phe Asp Pro
            100                 105                 110

Trp Gly Gln Gly Thr Val Val Thr Val Ser Ser
        115                 120

<210> SEQ ID NO 82
<211> LENGTH: 113
<212> TYPE: PRT
<213> ORGANISM: Artificial Sequence
<220> FEATURE:
<223> OTHER INFORMATION: Synthetic Construct

<400> SEQUENCE: 82

Gln Val Gln Leu Val Gln Ser Gly Ala Glu Val Lys Lys Pro Gly Ala
1               5                   10                  15
```

Ser Val Lys Val Ser Cys Lys Ala Ser Gly Asp Thr Ser Thr Ile His
             20                  25                  30

Ser Val His Trp Val Arg Gln Ala Pro Gly Gln Gly Leu Glu Trp Met
         35                  40                  45

Gly Thr Ile Ile Ser Ser Gly Thr Thr Thr Tyr Ala Gln Ser Phe
     50                  55                  60

Gln Asp Arg Val Ser Met Thr Ile Asp Arg Ser Thr Ser Thr Gly Tyr
65                  70                  75                  80

Met Glu Leu Ser Ser Leu Arg Phe Glu Asp Thr Ala Val Tyr Tyr Cys
                 85                  90                  95

Thr Thr Asp Gly Asp Ser Trp Gly Gln Gly Thr Leu Val Thr Val Ser
             100                 105                 110

Ser

<210> SEQ ID NO 83
<211> LENGTH: 119
<212> TYPE: PRT
<213> ORGANISM: Artificial Sequence
<220> FEATURE:
<223> OTHER INFORMATION: Synthetic Construct

<400> SEQUENCE: 83

Gln Val Gln Leu Gln Gln Ser Gly Pro Gly Leu Val Lys Thr Ser Glu
1                5                  10                  15

Thr Leu Ser Leu Thr Cys Thr Val Ser Gly Gly Ser Val Ser Asp Tyr
             20                  25                  30

Tyr Trp Ser Trp Ile Arg Gln Pro Pro Gly Lys Gly Leu Glu Trp Ile
         35                  40                  45

Gly Tyr Ile His Ser Ser Gly Ser Thr Asp Tyr Asn Pro Ser Leu Lys
     50                  55                  60

Ser Arg Leu Thr Ile Ser Gly Asp Ala Ala Lys Lys Gln Phe Ser Leu
65                  70                  75                  80

Asn Leu Ser Ser Val Thr Ala Ala Asp Thr Ala Leu Tyr Tyr Cys Ala
                 85                  90                  95

Arg Ala Gln Gly Gly Ser Arg Arg Thr Leu Asp Tyr Trp Gly Gln Gly
             100                 105                 110

Thr Leu Val Thr Val Ser Ser
         115

<210> SEQ ID NO 84
<211> LENGTH: 118
<212> TYPE: PRT
<213> ORGANISM: Artificial Sequence
<220> FEATURE:
<223> OTHER INFORMATION: Synthetic Construct

<400> SEQUENCE: 84

Gln Val Gln Leu Val Glu Ser Gly Pro Gly Leu Val Lys Pro Ser Glu
1                5                  10                  15

Thr Leu Ser Leu Thr Cys Thr Val Ser Val Asp Ser Thr Ser Ser Asp
             20                  25                  30

Tyr Trp Ser Trp Ile Arg Gln Ser Pro Gly Arg Gly Leu Glu Trp Ile
         35                  40                  45

Gly Tyr Ile Ser Asp Ser Gly Ser Thr Asp Tyr Asn Pro Ser Leu Lys
     50                  55                  60

Ser Arg Val Thr Ile Ser Gly Asp Arg Ser Thr Lys Gln Phe Ser Leu
65                  70                  75                  80

Lys Leu Thr Ser Val Thr Ala Ala Asp Thr Ala Val Tyr Tyr Cys Ala
                    85                  90                  95

Arg Ala Thr Val Thr Thr Tyr Ser Phe Asp Tyr Trp Gly Gln Gly Ala
                100                 105                 110

Leu Val Thr Val Ser Ser
        115

<210> SEQ ID NO 85
<211> LENGTH: 123
<212> TYPE: PRT
<213> ORGANISM: Artificial Sequence
<220> FEATURE:
<223> OTHER INFORMATION: Synthetic Construct

<400> SEQUENCE: 85

Gln Val Gln Leu Gln Gln Ser Gly Pro Gly Leu Val Lys Pro Ser Glu
1                   5                   10                  15

Thr Leu Ser Leu Thr Cys Thr Val Ser Gly Gly Ser Ile Ser Ser Thr
                20                  25                  30

Ser Tyr Trp Ala Trp Ile Arg Gln Pro Pro Gly Lys Gly Leu Glu Trp
        35                  40                  45

Ile Gly Thr Ile Tyr Tyr Asp Gly Tyr Thr Phe Tyr Asn Pro Ser Leu
    50                  55                  60

Lys Ser Arg Val Thr Ile Ser Gly Asp Thr Ser Lys Arg Gln Tyr Phe
65                  70                  75                  80

Leu Arg Leu Ser Ser Val Thr Ala Ala Asp Thr Ala Val Tyr Tyr Cys
                85                  90                  95

Ala Arg His Asp Ser Gly Gln Gln Leu Ile Asn Asn Trp Phe Asp Pro
                100                 105                 110

Trp Gly Gln Gly Thr Val Val Thr Val Ser Ser
        115                 120

<210> SEQ ID NO 86
<211> LENGTH: 123
<212> TYPE: PRT
<213> ORGANISM: Artificial Sequence
<220> FEATURE:
<223> OTHER INFORMATION: Synthetic Construct

<400> SEQUENCE: 86

Gln Val Gln Leu Gln Gln Ser Gly Pro Gly Leu Val Lys Pro Ser Glu
1                   5                   10                  15

Thr Leu Ser Leu Thr Cys Thr Val Ser Gly Tyr Ser Ile Ser Ser Gly
                20                  25                  30

Tyr Tyr Trp Ser Trp Val Arg Gln Pro Pro Gly Lys Gly Leu Glu Trp
        35                  40                  45

Ile Gly Ser Ile His His Ser Gly Ser Thr Tyr Tyr Asn Pro Ser Leu
    50                  55                  60

Gln Ser Arg Val Thr Ile Ser Gly Asp Thr Ser Lys Lys Glu Phe Ser
65                  70                  75                  80

Leu Gln Leu Ser Ser Val Thr Ala Ala Asp Thr Ala Val Tyr Tyr Cys
                85                  90                  95

Ala Arg Ala Glu Tyr Tyr Tyr Glu Ser Ser Gly Pro Leu Phe Asp Tyr
                100                 105                 110

Trp Gly Gln Gly Thr Leu Val Thr Val Ser Ser
        115                 120

<210> SEQ ID NO 87
<211> LENGTH: 122
<212> TYPE: PRT
<213> ORGANISM: Artificial Sequence
<220> FEATURE:
<223> OTHER INFORMATION: Synthetic Construct

<400> SEQUENCE: 87

```
Gln Val Gln Leu Gln Glu Ser Gly Pro Gly Leu Val Lys Pro Ser Glu
1               5                   10                  15

Thr Leu Ser Leu Thr Cys Thr Val Ser Asp Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Phe Ile His Asn Asn Gly Tyr Thr Asn Tyr Asn Pro Ser
    50                  55                  60

Leu Lys Ser Arg Val Thr Ile Ser Gly Asp Thr Ser Lys Lys Gln Phe
65                  70                  75                  80

Ser Leu Lys Val Thr Ser Val Thr Ala Ala Asp Thr Ala Val Tyr Tyr
                85                  90                  95

Cys Ala Arg Gly Glu Thr Tyr Glu Ser Ser Gly Tyr Tyr Asp Tyr Trp
            100                 105                 110

Gly Gln Gly Thr Leu Val Thr Val Ser Ser
        115                 120
```

<210> SEQ ID NO 88
<211> LENGTH: 121
<212> TYPE: PRT
<213> ORGANISM: Artificial Sequence
<220> FEATURE:
<223> OTHER INFORMATION: Synthetic Construct

<400> SEQUENCE: 88

```
Glu Val Gln Leu Leu Glu Ser Gly Pro Gly Leu Met Lys Pro Ser Glu
1               5                   10                  15

Thr Leu Ser Leu Thr Cys Ser Val Ser Gly Asp Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Ala Ser Ile Asn Tyr Ala Gly Ser Thr Tyr Tyr Asn Pro Ser
    50                  55                  60

Leu Lys Ser Arg Val Thr Ile Ser Gly Asp Thr Ser Lys Lys Gln Leu
65                  70                  75                  80

Tyr Leu Lys Leu Thr Ser Val Thr Ala Ala Asp Thr Ala Arg Tyr Tyr
                85                  90                  95

Cys Thr Arg Gln Asn Thr Ala Arg Gly Ile Ser Thr Asp Phe Trp Gly
            100                 105                 110

Leu Gly Thr Leu Val Thr Val Ser Ser
        115                 120
```

<210> SEQ ID NO 89
<211> LENGTH: 123
<212> TYPE: PRT
<213> ORGANISM: Artificial Sequence
<220> FEATURE:
<223> OTHER INFORMATION: Synthetic Construct

<400> SEQUENCE: 89

```
Glu Val Gln Leu Val Glu Ser Gly Pro Gly Leu Val Lys Pro Ser Glu
1               5                   10                  15
```

```
Thr Leu Ser Leu Thr Cys Thr Val Ser Gly Asp Ser Ile Arg Ser Ser
        20                  25                  30

Ser Ser Tyr Trp Gly Trp Ile Arg Gln Pro Pro Gly Lys Gly Leu Glu
        35                  40                  45

Trp Ile Gly Ser Ile Tyr Asp Asp Gly Thr Thr Phe Tyr Asn Pro Ser
    50                  55                  60

Phe Lys Ser Arg Val Thr Ile Ser Gly Asp Arg Ser Gln Met Gln Phe
65                  70                  75                  80

Ser Leu Lys Met Thr Ser Val Thr Ala Ala Asp Thr Ala Val Tyr Tyr
                85                  90                  95

Cys Ala Arg Thr Pro Tyr Gly Asp Tyr Ala Ser Tyr Phe Phe Asp Tyr
            100                 105                 110

Trp Gly Gln Gly Thr Leu Val Thr Val Ser Ser
        115                 120
```

<210> SEQ ID NO 90
<211> LENGTH: 112
<212> TYPE: PRT
<213> ORGANISM: Artificial Sequence
<220> FEATURE:
<223> OTHER INFORMATION: Synthetic Construct

<400> SEQUENCE: 90

```
Glu Val Gln Leu Val Gln Ser Gly Ala Glu Val Lys Asn Pro Gly Ala
1                   5                   10                  15

Ser Val Lys Val Ser Cys Lys Ala Ser Gly His Ala Phe Ala Gly Thr
                20                  25                  30

Tyr Val His Trp Val Arg Gln Ala Pro Gly Gln Gly Phe Glu Trp Ile
            35                  40                  45

Gly Trp Ile Asp Arg Asn Arg Gly Gly Thr Asn Tyr Ala Gln Lys Phe
    50                  55                  60

Gln Gly Arg Val Thr Met Thr Arg Asp Thr Ser Ile Ser Thr Val Tyr
65                  70                  75                  80

Met Glu Leu Ser Ser Leu Arg Ser Asp Asp Thr Ala Val Tyr Tyr Cys
                85                  90                  95

Ala Ser Asp Pro Gly Leu Gly Gln Gly Thr Leu Val Thr Val Ser Ser
            100                 105                 110
```

<210> SEQ ID NO 91
<211> LENGTH: 112
<212> TYPE: PRT
<213> ORGANISM: Artificial Sequence
<220> FEATURE:
<223> OTHER INFORMATION: Synthetic Construct

<400> SEQUENCE: 91

```
Asp Ile Val Met Thr Gln Thr Pro Leu Ser Leu Pro Val Thr Pro Gly
1                   5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Ala
              85                  90                  95

Leu Gln Thr Pro Tyr Thr Phe Gly Gln Gly Thr Lys Leu Glu Ile Lys
              100                 105                 110

<210> SEQ ID NO 92
<211> LENGTH: 107
<212> TYPE: PRT
<213> ORGANISM: Artificial Sequence
<220> FEATURE:
<223> OTHER INFORMATION: Synthetic Construct

<400> SEQUENCE: 92

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Tyr Tyr
              20                  25                  30

Leu Asn Trp Tyr Gln Gln Lys Pro Gly Glu Ala Pro Lys Leu Leu Ile
          35                  40                  45

Tyr Ala Ala Ser Ser Leu Gln Ser Gly Val Pro Ser Arg Phe Ser Gly
      50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ile Pro Tyr
              85                  90                  95

Thr Phe Gly Gln Gly Thr Lys Leu Glu Ile Lys
              100                 105

<210> SEQ ID NO 93
<211> LENGTH: 107
<212> TYPE: PRT
<213> ORGANISM: Artificial Sequence
<220> FEATURE:
<223> OTHER INFORMATION: Synthetic Construct

<400> SEQUENCE: 93

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
              20                  25                  30

Leu Ala Trp Tyr Gln Gln Lys Pro Gly Gln Ala Pro Arg Leu Leu Ile
          35                  40                  45

Tyr Gly Ala Ser Thr Arg Ala Thr Gly Ile Pro Ala Arg Phe Ser Gly
      50                  55                  60

Ser Gly Ser Gly Thr Glu Phe Thr Leu Thr Ile Ser Arg Leu Glu Pro
65                  70                  75                  80

Glu Asp Phe Ala Val Tyr Tyr Cys Gln Gln Ser Gly Asp Ser Leu Val
              85                  90                  95

Thr Phe Gly Gln Gly Thr Arg Leu Glu Ile Lys
              100                 105

<210> SEQ ID NO 94
<211> LENGTH: 107
<212> TYPE: PRT
<213> ORGANISM: Artificial Sequence
<220> FEATURE:
<223> OTHER INFORMATION: Synthetic Construct

<400> SEQUENCE: 94

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Asn Ser Leu Pro His
                85                  90                  95

Thr Phe Gly Gln Gly Thr Lys Leu Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: Synthetic Construct

<400> SEQUENCE: 95

Glu Ile Val Met Thr Gln Ser Pro Ser Thr Leu Ser Ala Ser Val Gly
1               5                   10                  15

Asp Arg Val Ala Ile Thr Cys Arg Ala Ser Gln Thr Ile Ser Ser Tyr
            20                  25                  30

Leu Asn Trp Tyr Gln Leu Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Asp Ile Lys
            100                 105

<210> SEQ ID NO 96
<211> LENGTH: 107
<212> TYPE: PRT
<213> ORGANISM: Artificial Sequence
<220> FEATURE:
<223> OTHER INFORMATION: Synthetic Construct

<400> SEQUENCE: 96

Asp Ile Gln Leu Thr Gln Ser Pro Ser Ser Val Ser Ala Ser Val Gly
1               5                   10                  15

Asp Thr Val Thr Ile Thr Cys Arg Ala Ser Gln Gly Ile Asn Arg Trp
            20                  25                  30

Leu Ala Trp Tyr Gln Gln Lys Pro Gly Lys Ala Pro Asn Leu Leu Ile
        35                  40                  45

Tyr Ala Thr Ser Thr Leu Gln Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Gly Tyr Thr Leu Pro Pro
                85                  90                  95

Thr Leu Gly Gln Gly Thr Arg Leu Glu Ile Lys
            100                 105

<210> SEQ ID NO 97
<211> LENGTH: 107
<212> TYPE: PRT
<213> ORGANISM: Artificial Sequence
<220> FEATURE:
<223> OTHER INFORMATION: Synthetic Construct

<400> SEQUENCE: 97

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Val Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Asp Ser Leu Gln Pro
65                  70                  75                  80

Glu Asp Phe Ala Thr Tyr Phe Cys Gln Gln Ser Phe Ser Val Pro Ile
                85                  90                  95

Thr Phe Gly Gln Gly Thr Arg Leu Glu Ile Lys
            100                 105

<210> SEQ ID NO 98
<211> LENGTH: 112
<212> TYPE: PRT
<213> ORGANISM: Artificial Sequence
<220> FEATURE:
<223> OTHER INFORMATION: Synthetic Construct

<400> SEQUENCE: 98

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Leu Glu Ile Lys
            100                 105                 110

<210> SEQ ID NO 99
<211> LENGTH: 107
<212> TYPE: PRT
<213> ORGANISM: Artificial Sequence
<220> FEATURE:
<223> OTHER INFORMATION: Synthetic Construct

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Ser
            20                  25                  30

Leu Asn Trp Tyr Gln Gln Arg Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Thr Ala Pro Tyr
                85                  90                  95

Thr Phe Gly Gln Gly Thr Lys Leu Glu Ile Lys
            100                 105

<210> SEQ ID NO 100
<211> LENGTH: 107
<212> TYPE: PRT
<213> ORGANISM: Artificial Sequence
<220> FEATURE:
<223> OTHER INFORMATION: Synthetic Construct

<400> SEQUENCE: 100

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Glu Leu Leu Ile
        35                  40                  45

Tyr Thr Ala Ser Asn Leu Gln Thr Gly Val Pro Ala Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Cys Gln Gln Ser Tyr Asp Ser Pro Leu
                85                  90                  95

Thr Phe Gly Gly Gly Thr Lys Val Asp Ile Lys
            100                 105

<210> SEQ ID NO 101
<211> LENGTH: 107
<212> TYPE: PRT
<213> ORGANISM: Artificial Sequence
<220> FEATURE:
<223> OTHER INFORMATION: Synthetic Construct

<400> SEQUENCE: 101

Val Ile Arg Met Thr Gln Ser Pro Ser Ser Leu Ser Ala Ser Leu Gly
1               5                   10                  15

Asp Arg Val Thr Ile Thr Cys Arg Ala Ser Gln Ser Ile Gly Arg Tyr
            20                  25                  30

Leu Asn Trp Tyr Gln His Lys Ala Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Leu Pro Phe
                85                  90                  95

Thr Phe Gly Gln Gly Thr Arg Leu Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Synthetic Construct

<400> SEQUENCE: 102

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Phe Gly Ala Ser Ser Arg Ala Thr Gly Ile Pro Asp Arg Phe Ser
        50                  55                  60

Gly Ser Gly Ser Gly Thr Asp Phe Ile Leu Thr Ile Ser Arg Leu Glu
65                  70                  75                  80

Pro Glu Asp Phe Ala Val Tyr Tyr Cys Gln His Tyr Asp Asn Ser Leu
                85                  90                  95

Thr Phe Gly Gly Gly Thr Lys Leu Glu Ile Lys
            100                 105

<210> SEQ ID NO 103
<211> LENGTH: 112
<212> TYPE: PRT
<213> ORGANISM: Artificial Sequence
<220> FEATURE:
<223> OTHER INFORMATION: Synthetic Construct

<400> SEQUENCE: 103

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Glu Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Gln Leu Pro Leu Thr Phe Gly Gly Gly Thr Lys Leu Glu Ile Lys
            100                 105                 110

<210> SEQ ID NO 104
<211> LENGTH: 112
<212> TYPE: PRT
<213> ORGANISM: Artificial Sequence
<220> FEATURE:
<223> OTHER INFORMATION: Synthetic Construct

<400> SEQUENCE: 104

Glu Ile Val Leu Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Met Gly Ser Asn Arg Ala Ser Gly Val Ser
    50                  55                  60

Asp Arg Phe Asn Gly Ser Gly Ser Gly Arg Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Leu Thr Phe Gly Gly Gly Thr Lys Leu Glu Ile Lys
            100                 105                 110

<210> SEQ ID NO 105
<211> LENGTH: 113
<212> TYPE: PRT
<213> ORGANISM: Artificial Sequence
<220> FEATURE:
<223> OTHER INFORMATION: Synthetic Construct

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Ser Thr Ile His
            20                  25                  30

Ser Val His Trp Val Arg Gln Ala Pro Gly Gln Gly Leu Glu Trp Met
        35                  40                  45

Gly Thr Ile Ile Ser Ser Gly Thr Thr Thr Tyr Ala Gln Ser Phe
    50                  55                  60

Gln Asp Arg Val Ser Met Thr Ile Asp Arg Ser Thr Ser Thr Gly Tyr
65                  70                  75                  80

Met Glu Leu Ser Ser Leu Arg Phe Glu Asp Thr Ala Val Tyr Tyr Cys
                85                  90                  95

Thr Thr Asp Gly Asp Ala Trp Gly Gln Gly Thr Leu Val Thr Val Ser
            100                 105                 110

Ser

<210> SEQ ID NO 106
<211> LENGTH: 113
<212> TYPE: PRT
<213> ORGANISM: Artificial Sequence
<220> FEATURE:
<223> OTHER INFORMATION: Synthetic Construct

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Ser Thr Ile His
            20                  25                  30

Ser Val His Trp Val Arg Gln Ala Pro Gly Gln Gly Leu Glu Trp Met
        35                  40                  45

Gly Thr Ile Ile Ser Ser Gly Thr Thr Thr Thr Tyr Ala Gln Ser Phe
    50                  55                  60

-continued

```
Gln Asp Arg Val Ser Met Thr Ile Asp Arg Ser Thr Ser Thr Gly Tyr
65                  70                  75                  80

Met Glu Leu Ser Ser Leu Arg Phe Glu Asp Thr Ala Val Tyr Tyr Cys
                85                  90                  95

Thr Thr Asp Gly Asp Thr Trp Gly Gln Gly Thr Leu Val Thr Val Ser
                100                 105                 110

Ser
```

<210> SEQ ID NO 107
<211> LENGTH: 113
<212> TYPE: PRT
<213> ORGANISM: Artificial Sequence
<220> FEATURE:
<223> OTHER INFORMATION: Synthetic Construct

<400> SEQUENCE: 107

```
Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Ser Thr Ile His
                20                  25                  30

Ser Val His Trp Val Arg Gln Ala Pro Gly Gln Gly Leu Glu Trp Met
            35                  40                  45

Gly Thr Ile Ile Ser Ser Gly Thr Thr Thr Thr Tyr Ala Gln Ser Phe
        50                  55                  60

Gln Asp Arg Val Ser Met Thr Ile Asp Arg Ser Thr Ser Thr Gly Tyr
65                  70                  75                  80

Met Glu Leu Ser Ser Leu Arg Phe Glu Asp Thr Ala Val Tyr Tyr Cys
                85                  90                  95

Thr Thr Asp Gly Thr Ser Trp Gly Gln Gly Thr Leu Val Thr Val Ser
                100                 105                 110

Ser
```

<210> SEQ ID NO 108
<211> LENGTH: 113
<212> TYPE: PRT
<213> ORGANISM: Artificial Sequence
<220> FEATURE:
<223> OTHER INFORMATION: Synthetic Construct

<400> SEQUENCE: 108

```
Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Ser Thr Ile His
                20                  25                  30

Ser Val His Trp Val Arg Gln Ala Pro Gly Gln Gly Leu Glu Trp Met
            35                  40                  45

Gly Thr Ile Ile Ser Ser Gly Thr Thr Thr Thr Tyr Ala Gln Ser Phe
        50                  55                  60

Gln Asp Arg Val Ser Met Thr Ile Asp Arg Ser Thr Ser Thr Gly Tyr
65                  70                  75                  80

Met Glu Leu Ser Ser Leu Arg Phe Glu Asp Thr Ala Val Tyr Tyr Cys
                85                  90                  95

Thr Thr Tyr Gly Asp Ser Trp Gly Gln Gly Thr Leu Val Thr Val Ser
                100                 105                 110

Ser
```

<210> SEQ ID NO 109

<211> LENGTH: 113
<212> TYPE: PRT
<213> ORGANISM: Artificial Sequence
<220> FEATURE:
<223> OTHER INFORMATION: Synthetic Construct

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Ser Thr Ile His
            20                  25                  30

Ser Val His Trp Val Arg Gln Ala Pro Gly Gln Gly Leu Glu Trp Met
        35                  40                  45

Gly Thr Ile Ile Ser Ser Gly Thr Thr Thr Thr Tyr Ala Gln Ser Phe
    50                  55                  60

Gln Asp Arg Val Ser Met Thr Ile Asp Arg Ser Thr Ser Thr Gly Tyr
65                  70                  75                  80

Met Glu Leu Ser Ser Leu Arg Phe Glu Asp Thr Ala Val Tyr Tyr Cys
                85                  90                  95

Thr Thr Asn Gly Asp Ser Trp Gly Gln Gly Thr Leu Val Thr Val Ser
            100                 105                 110

Ser

<210> SEQ ID NO 110
<211> LENGTH: 113
<212> TYPE: PRT
<213> ORGANISM: Artificial Sequence
<220> FEATURE:
<223> OTHER INFORMATION: Synthetic Construct

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Ser Thr Ile His
            20                  25                  30

Ser Val His Trp Val Arg Gln Ala Pro Gly Gln Gly Leu Glu Trp Met
        35                  40                  45

Gly Thr Ile Ile Ser Ser Gly Thr Thr Thr Thr Tyr Ala Gln Ser Phe
    50                  55                  60

Gln Asp Arg Val Ser Met Thr Ile Asp Arg Ser Thr Ser Thr Gly Tyr
65                  70                  75                  80

Met Glu Leu Ser Ser Leu Arg Phe Glu Asp Thr Ala Val Tyr Tyr Cys
                85                  90                  95

Thr Thr Asp Ala Asp Ser Trp Gly Gln Gly Thr Leu Val Thr Val Ser
            100                 105                 110

Ser

<210> SEQ ID NO 111
<211> LENGTH: 107
<212> TYPE: PRT
<213> ORGANISM: Artificial Sequence
<220> FEATURE:
<223> OTHER INFORMATION: Synthetic Construct

<400> SEQUENCE: 111

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Asp Ser Leu Pro His
                85                  90                  95

Thr Phe Gly Gln Gly Thr Lys Leu Glu Ile Lys
                100                 105

<210> SEQ ID NO 112
<211> LENGTH: 107
<212> TYPE: PRT
<213> ORGANISM: Artificial Sequence
<220> FEATURE:
<223> OTHER INFORMATION: Synthetic Construct

<400> SEQUENCE: 112

Asp Ile Gln Leu Thr Gln Ser Pro Ser Ser Val Ser Ala Ser Val Gly
1                   5                   10                  15

Asp Arg Val Thr Ile Ala Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Tyr Ser Leu Pro His
                85                  90                  95

Thr Phe Gly Gln Gly Thr Lys Leu Glu Ile Lys
                100                 105

<210> SEQ ID NO 113
<211> LENGTH: 107
<212> TYPE: PRT
<213> ORGANISM: Artificial Sequence
<220> FEATURE:
<223> OTHER INFORMATION: Synthetic Construct

<400> SEQUENCE: 113

Asp Ile Gln Leu Thr Gln Ser Pro Ser Ser Val Ser Ala Ser Val Gly
1                   5                   10                  15

Asp Arg Val Thr Ile Ala Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Phe Ser Leu Pro His
                85                  90                  95

Thr Phe Gly Gln Gly Thr Lys Leu Glu Ile Lys
                100                 105

-continued

```
<210> SEQ ID NO 114
<211> LENGTH: 107
<212> TYPE: PRT
<213> ORGANISM: Artificial Sequence
<220> FEATURE:
<223> OTHER INFORMATION: Synthetic Construct

<400> SEQUENCE: 114

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Leu Ser Leu Pro His
                85                  90                  95

Thr Phe Gly Gln Gly Thr Lys Leu Glu Ile Lys
            100                 105

<210> SEQ ID NO 115
<211> LENGTH: 107
<212> TYPE: PRT
<213> ORGANISM: Artificial Sequence
<220> FEATURE:
<223> OTHER INFORMATION: Synthetic Construct

<400> SEQUENCE: 115

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Gly Ser Leu Pro His
                85                  90                  95

Thr Phe Gly Gln Gly Thr Lys Leu Glu Ile Lys
            100                 105

<210> SEQ ID NO 116
<211> LENGTH: 107
<212> TYPE: PRT
<213> ORGANISM: Artificial Sequence
<220> FEATURE:
<223> OTHER INFORMATION: Synthetic Construct

<400> SEQUENCE: 116

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45
```

-continued

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Lys Ser Leu Pro His
                85                  90                  95

Thr Phe Gly Gln Gly Thr Lys Leu Glu Ile Lys
            100                 105

<210> SEQ ID NO 117
<211> LENGTH: 107
<212> TYPE: PRT
<213> ORGANISM: Artificial Sequence
<220> FEATURE:
<223> OTHER INFORMATION: Synthetic Construct

<400> SEQUENCE: 117

Asp Ile Gln Leu Thr Gln Ser Pro Ser Ser Val Ser Ala Ser Val Gly
1                   5                   10                  15

Asp Arg Val Thr Ile Ala Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala His Ser Leu Pro His
                85                  90                  95

Thr Phe Gly Gln Gly Thr Lys Leu Glu Ile Lys
            100                 105

<210> SEQ ID NO 118
<211> LENGTH: 107
<212> TYPE: PRT
<213> ORGANISM: Artificial Sequence
<220> FEATURE:
<223> OTHER INFORMATION: Synthetic Construct

<400> SEQUENCE: 118

Asp Ile Gln Leu Thr Gln Ser Pro Ser Ser Val Ser Ala Ser Val Gly
1                   5                   10                  15

Asp Arg Val Thr Ile Ala Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Ala Ser Leu Pro His
                85                  90                  95

Thr Phe Gly Gln Gly Thr Lys Leu Glu Ile Lys
            100                 105

<210> SEQ ID NO 119
<211> LENGTH: 107
<212> TYPE: PRT

<213> ORGANISM: Artificial Sequence
<220> FEATURE:
<223> OTHER INFORMATION: Synthetic Construct

<400> SEQUENCE: 119

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Cys Ser Leu Pro His
                85                  90                  95

Thr Phe Gly Gln Gly Thr Lys Leu Glu Ile Lys
            100                 105

<210> SEQ ID NO 120
<211> LENGTH: 107
<212> TYPE: PRT
<213> ORGANISM: Artificial Sequence
<220> FEATURE:
<223> OTHER INFORMATION: Synthetic Construct

<400> SEQUENCE: 120

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Glu Ser Leu Pro His
                85                  90                  95

Thr Phe Gly Gln Gly Thr Lys Leu Glu Ile Lys
            100                 105

<210> SEQ ID NO 121
<211> LENGTH: 107
<212> TYPE: PRT
<213> ORGANISM: Artificial Sequence
<220> FEATURE:
<223> OTHER INFORMATION: Synthetic Construct

<400> SEQUENCE: 121

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

-continued

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Gln Ser Leu Pro His
                85                  90                  95

Thr Phe Gly Gln Gly Thr Lys Leu Glu Ile Lys
            100                 105

<210> SEQ ID NO 122
<211> LENGTH: 107
<212> TYPE: PRT
<213> ORGANISM: Artificial Sequence
<220> FEATURE:
<223> OTHER INFORMATION: Synthetic Construct

<400> SEQUENCE: 122

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr His Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Arg Ser Leu Pro His
                85                  90                  95

Thr Phe Gly Gln Gly Thr Lys Leu Glu Ile Lys
            100                 105

<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr His Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Ser Ser Leu Pro His
                85                  90                  95

Thr Phe Gly Gln Gly Thr Lys Leu Glu Ile Lys
            100                 105

<210> SEQ ID NO 124
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 124

```
Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Thr Ser Leu Pro His
                85                  90                  95

Thr Phe Gly Gln Gly Thr Lys Leu Glu Ile Lys
            100                 105
```

<210> SEQ ID NO 125
<211> LENGTH: 107
<212> TYPE: PRT
<213> ORGANISM: Artificial Sequence
<220> FEATURE:
<223> OTHER INFORMATION: Synthetic Construct

<400> SEQUENCE: 125

```
Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Val Ser Leu Pro His
                85                  90                  95

Thr Phe Gly Gln Gly Thr Lys Leu Glu Ile Lys
            100                 105
```

<210> SEQ ID NO 126
<211> LENGTH: 107
<212> TYPE: PRT
<213> ORGANISM: Artificial Sequence
<220> FEATURE:
<223> OTHER INFORMATION: Synthetic Construct

<400> SEQUENCE: 126

```
Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Leu Gln Ala Trp Ser Leu Pro His
            85                  90                  95

Thr Phe Gly Gln Gly Thr Lys Leu Glu Ile Lys
            100                 105

<210> SEQ ID NO 127
<211> LENGTH: 107
<212> TYPE: PRT
<213> ORGANISM: Artificial Sequence
<220> FEATURE:
<223> OTHER INFORMATION: Synthetic Construct

<400> SEQUENCE: 127

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Pro Ser Leu Pro His
            85                  90                  95

Thr Phe Gly Gln Gly Thr Lys Leu Glu Ile Lys
            100                 105

<210> SEQ ID NO 128
<211> LENGTH: 123
<212> TYPE: PRT
<213> ORGANISM: Artificial Sequence
<220> FEATURE:
<223> OTHER INFORMATION: Synthetic Construct

<400> SEQUENCE: 128

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
            85                  90                  95

Cys Ala Arg Gln Phe Gly Ser Glu Thr Tyr Tyr Asn Gly Ile Tyr Pro
            100                 105                 110

Trp Gly Gln Gly Thr Leu Val Thr Val Ser Ser
        115                 120

<210> SEQ ID NO 129
<211> LENGTH: 123
<212> TYPE: PRT
<213> ORGANISM: Artificial Sequence
<220> FEATURE:
<223> OTHER INFORMATION: Synthetic Construct
```

<400> SEQUENCE: 129

Gln Val Gln Leu Gln Gln Ser Gly Pro Gly Leu Val Lys Pro Ser Glu
1                   5                   10                  15

Thr Leu Ser Leu Thr Cys Thr Val Ser Gly Gly Pro Ile Thr Ser Ser
                20                  25                  30

Gly Asp Tyr Trp Gly Trp Ile Arg Gln Pro Pro Gly Lys Gly Leu Glu
            35                  40                  45

Leu Ile Gly Ser Ile His Asn Ser Gly Ser Thr Tyr Tyr Asn Pro Ser
        50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Cys Pro
            100                 105                 110

Trp Gly Gln Gly Thr Leu Val Thr Val Ser Ser
        115                 120

<210> SEQ ID NO 130
<211> LENGTH: 123
<212> TYPE: PRT
<213> ORGANISM: Artificial Sequence
<220> FEATURE:
<223> OTHER INFORMATION: Synthetic Construct

<400> SEQUENCE: 130

Gln Val Gln Leu Gln Gln Ser Gly Pro Gly Leu Val Lys Pro Ser Glu
1                   5                   10                  15

Thr Leu Ser Leu Thr Cys Thr Val Ser Gly Gly Pro Ile Thr Ser Ser
                20                  25                  30

Gly Asp Tyr Trp Gly Trp Ile Arg Gln Pro Pro Gly Lys Gly Leu Glu
            35                  40                  45

Leu Ile Gly Ser Ile His Asn Ser Gly Ser Thr Tyr Tyr Asn Pro Ser
        50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile His Pro
            100                 105                 110

Trp Gly Gln Gly Thr Leu Val Thr Val Ser Ser
        115                 120

<210> SEQ ID NO 131
<211> LENGTH: 123
<212> TYPE: PRT
<213> ORGANISM: Artificial Sequence
<220> FEATURE:
<223> OTHER INFORMATION: Synthetic Construct

<400> SEQUENCE: 131

Gln Val Gln Leu Gln Gln Ser Gly Pro Gly Leu Val Lys Pro Ser Glu
1                   5                   10                  15

Thr Leu Ser Leu Thr Cys Thr Val Ser Gly Gly Pro Ile Thr Ser Ser
                20                  25                  30

Gly Asp Tyr Trp Gly Trp Ile Arg Gln Pro Pro Gly Lys Gly Leu Glu
            35                  40                  45

-continued

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Ser Pro
            100                 105                 110

Trp Gly Gln Gly Thr Leu Val Thr Val Ser Ser
        115                 120

<210> SEQ ID NO 132
<211> LENGTH: 123
<212> TYPE: PRT
<213> ORGANISM: Artificial Sequence
<220> FEATURE:
<223> OTHER INFORMATION: Synthetic Construct

<400> SEQUENCE: 132

Gln Val Gln Leu Gln Gln Ser Gly Pro Gly Leu Val Lys Pro Ser Glu
1                   5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Gln Pro
            100                 105                 110

Trp Gly Gln Gly Thr Leu Val Thr Val Ser Ser
        115                 120

<210> SEQ ID NO 133
<211> LENGTH: 123
<212> TYPE: PRT
<213> ORGANISM: Artificial Sequence
<220> FEATURE:
<223> OTHER INFORMATION: Synthetic Construct

<400> SEQUENCE: 133

Gln Val Gln Leu Gln Gln Ser Gly Pro Gly Leu Val Lys Pro Ser Glu
1                   5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

```
Cys Ala Arg Gln Phe Gly Ser Glu Thr Tyr Tyr Asn Gly Ile Arg Pro
                100                 105                 110

Trp Gly Gln Gly Thr Leu Val Thr Val Ser Ser
        115                 120

<210> SEQ ID NO 134
<211> LENGTH: 123
<212> TYPE: PRT
<213> ORGANISM: Artificial Sequence
<220> FEATURE:
<223> OTHER INFORMATION: Synthetic Construct

<400> SEQUENCE: 134

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
                20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Ala Pro
                100                 105                 110

Trp Gly Gln Gly Thr Leu Val Thr Val Ser Ser
        115                 120

<210> SEQ ID NO 135
<211> LENGTH: 123
<212> TYPE: PRT
<213> ORGANISM: Artificial Sequence
<220> FEATURE:
<223> OTHER INFORMATION: Synthetic Construct

<400> SEQUENCE: 135

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
                20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Glu Pro
                100                 105                 110

Trp Gly Gln Gly Thr Leu Val Thr Val Ser Ser
        115                 120

<210> SEQ ID NO 136
<211> LENGTH: 123
<212> TYPE: PRT
```

<213> ORGANISM: Artificial Sequence
<220> FEATURE:
<223> OTHER INFORMATION: Synthetic Construct

<400> SEQUENCE: 136

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Gly Pro
            100                 105                 110

Trp Gly Gln Gly Thr Leu Val Thr Val Ser Ser
        115                 120

<210> SEQ ID NO 137
<211> LENGTH: 123
<212> TYPE: PRT
<213> ORGANISM: Artificial Sequence
<220> FEATURE:
<223> OTHER INFORMATION: Synthetic Construct

<400> SEQUENCE: 137

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Lys Pro
            100                 105                 110

Trp Gly Gln Gly Thr Leu Val Thr Val Ser Ser
        115                 120

<210> SEQ ID NO 138
<211> LENGTH: 123
<212> TYPE: PRT
<213> ORGANISM: Artificial Sequence
<220> FEATURE:
<223> OTHER INFORMATION: Synthetic Construct

<400> SEQUENCE: 138

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

-continued

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Trp Pro
            100                 105                 110

Trp Gly Gln Gly Thr Leu Val Thr Val Ser Ser
        115                 120

<210> SEQ ID NO 139
<211> LENGTH: 123
<212> TYPE: PRT
<213> ORGANISM: Artificial Sequence
<220> FEATURE:
<223> OTHER INFORMATION: Synthetic Construct

<400> SEQUENCE: 139

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Val Pro
            100                 105                 110

Trp Gly Gln Gly Thr Leu Val Thr Val Ser Ser
        115                 120

<210> SEQ ID NO 140
<211> LENGTH: 112
<212> TYPE: PRT
<213> ORGANISM: Artificial Sequence
<220> FEATURE:
<223> OTHER INFORMATION: Synthetic Construct

<400> SEQUENCE: 140

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Ala Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

-continued

Ser Arg Val Glu Ala Glu Asp Val Gly Val Tyr Tyr Cys Met Gln Ala
            85                  90                  95

Leu Gln Thr Pro Tyr Thr Phe Gly Gln Gly Thr Lys Leu Glu Ile Lys
            100                 105                 110

<210> SEQ ID NO 141
<211> LENGTH: 112
<212> TYPE: PRT
<213> ORGANISM: Artificial Sequence
<220> FEATURE:
<223> OTHER INFORMATION: Synthetic Construct

<400> SEQUENCE: 141

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Val Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro Tyr Thr Phe Gly Gln Gly Thr Lys Leu Glu Ile Lys
            100                 105                 110

<210> SEQ ID NO 142
<211> LENGTH: 112
<212> TYPE: PRT
<213> ORGANISM: Artificial Sequence
<220> FEATURE:
<223> OTHER INFORMATION: Synthetic Construct

<400> SEQUENCE: 142

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Phe Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro Tyr Thr Phe Gly Gln Gly Thr Lys Leu Glu Ile Lys
            100                 105                 110

<210> SEQ ID NO 143
<211> LENGTH: 112
<212> TYPE: PRT
<213> ORGANISM: Artificial Sequence
<220> FEATURE:
<223> OTHER INFORMATION: Synthetic Construct

```
<400> SEQUENCE: 143

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Arg Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 144
<211> LENGTH: 112
<212> TYPE: PRT
<213> ORGANISM: Artificial Sequence
<220> FEATURE:
<223> OTHER INFORMATION: Synthetic Construct

<400> SEQUENCE: 144

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Gly Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 145
<211> LENGTH: 112
<212> TYPE: PRT
<213> ORGANISM: Artificial Sequence
<220> FEATURE:
<223> OTHER INFORMATION: Synthetic Construct

<400> SEQUENCE: 145

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

-continued

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
                100                 105                 110

<210> SEQ ID NO 146
<211> LENGTH: 112
<212> TYPE: PRT
<213> ORGANISM: Artificial Sequence
<220> FEATURE:
<223> OTHER INFORMATION: Synthetic Construct

<400> SEQUENCE: 146

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Gln Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
                100                 105                 110

<210> SEQ ID NO 147
<211> LENGTH: 112
<212> TYPE: PRT
<213> ORGANISM: Artificial Sequence
<220> FEATURE:
<223> OTHER INFORMATION: Synthetic Construct

<400> SEQUENCE: 147

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Trp Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
                100                 105                 110

<210> SEQ ID NO 148
<211> LENGTH: 112
<212> TYPE: PRT
<213> ORGANISM: Artificial Sequence
<220> FEATURE:
<223> OTHER INFORMATION: Synthetic Construct

<400> SEQUENCE: 148

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Pro Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 149
<211> LENGTH: 123
<212> TYPE: PRT
<213> ORGANISM: Artificial Sequence
<220> FEATURE:
<223> OTHER INFORMATION: Synthetic Construct

<400> SEQUENCE: 149

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Gln Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Pro Gly Ile Asp Pro
            100                 105                 110

Trp Gly Gln Gly Thr Leu Val Thr Val Ser Ser
        115                 120

<210> SEQ ID NO 150
<211> LENGTH: 123
<212> TYPE: PRT
<213> ORGANISM: Artificial Sequence
<220> FEATURE:
<223> OTHER INFORMATION: Synthetic Construct

<400> SEQUENCE: 150

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Lys Gly Ser Thr Tyr Tyr Asn Pro Ser
    50                  55                  60

```
Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Thr Gly Ile Asp Pro
            100                 105                 110

Trp Gly Gln Gly Thr Leu Val Thr Val Ser Ser
        115                 120

<210> SEQ ID NO 151
<211> LENGTH: 123
<212> TYPE: PRT
<213> ORGANISM: Artificial Sequence
<220> FEATURE:
<223> OTHER INFORMATION: Synthetic Construct

<400> SEQUENCE: 151

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
                20                  25                  30

Gly Asp Tyr Trp Gly Trp Ile Arg Gln Pro Pro Gly Lys Gly Leu Glu
            35                  40                  45

Leu Ile Gly Ser Ile His Asn Ser Gly Ser Thr Tyr Tyr Asn Pro Ser
        50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Asp Pro
            100                 105                 110

Trp Gly Gln Gly Thr Leu Val Thr Val Ser Ser
        115                 120

<210> SEQ ID NO 152
<211> LENGTH: 123
<212> TYPE: PRT
<213> ORGANISM: Artificial Sequence
<220> FEATURE:
<223> OTHER INFORMATION: Synthetic Construct

<400> SEQUENCE: 152

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
                20                  25                  30

Gly Asp Tyr Trp Gly Trp Ile Arg Gln Pro Pro Gly Lys Gly Leu Glu
            35                  40                  45

Leu Ile Gly Ser Ile His Asn Gln Gly Ser Thr Tyr Tyr Asn Pro Ser
        50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Thr Gly Ile Gln Pro
            100                 105                 110
```

```
Trp Gly Gln Gly Thr Leu Val Thr Val Ser Ser
        115                 120

<210> SEQ ID NO 153
<211> LENGTH: 123
<212> TYPE: PRT
<213> ORGANISM: Artificial Sequence
<220> FEATURE:
<223> OTHER INFORMATION: Synthetic Construct

<400> SEQUENCE: 153

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Lys Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Thr Gly Ile Gln Pro
            100                 105                 110

Trp Gly Gln Gly Thr Leu Val Thr Val Ser Ser
        115                 120

<210> SEQ ID NO 154
<211> LENGTH: 123
<212> TYPE: PRT
<213> ORGANISM: Artificial Sequence
<220> FEATURE:
<223> OTHER INFORMATION: Synthetic Construct

<400> SEQUENCE: 154

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Ser Gly Ile Asp Pro
            100                 105                 110

Trp Gly Gln Gly Thr Leu Val Thr Val Ser Ser
        115                 120

<210> SEQ ID NO 155
<211> LENGTH: 123
<212> TYPE: PRT
<213> ORGANISM: Artificial Sequence
<220> FEATURE:
<223> OTHER INFORMATION: Synthetic Construct
```

-continued

<400> SEQUENCE: 155

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Val Gly Ile Asp Pro
            100                 105                 110

Trp Gly Gln Gly Thr Leu Val Thr Val Ser Ser
        115                 120

<210> SEQ ID NO 156
<211> LENGTH: 123
<212> TYPE: PRT
<213> ORGANISM: Artificial Sequence
<220> FEATURE:
<223> OTHER INFORMATION: Synthetic Construct

<400> SEQUENCE: 156

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Val Gly Ile Gln Pro
            100                 105                 110

Trp Gly Gln Gly Thr Leu Val Thr Val Ser Ser
        115                 120

<210> SEQ ID NO 157
<211> LENGTH: 123
<212> TYPE: PRT
<213> ORGANISM: Artificial Sequence
<220> FEATURE:
<223> OTHER INFORMATION: Synthetic Construct

<400> SEQUENCE: 157

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

```
Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Ser Gly Ile Gln Pro
            100                 105                 110

Trp Gly Gln Gly Thr Leu Val Thr Val Ser Ser
        115                 120
```

<210> SEQ ID NO 158
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser, Pro, Leu, Tyr, Lys, Arg, Thr, Gln,
      Ala, Asn, Phe, Trp, Val, Gly, Cys, Asp, Glu, or His

<400> SEQUENCE: 158

```
Leu Gln Ala Xaa Ser Leu Pro His Thr
1               5
```

<210> SEQ ID NO 159
<211> LENGTH: 119
<212> TYPE: PRT
<213> ORGANISM: Artificial Sequence
<220> FEATURE:
<223> OTHER INFORMATION: Synthetic Construct

<400> SEQUENCE: 159

```
Gln Val Gln Leu Gln Gln Ser Gly Pro Gly Leu Val Lys Thr Ser Glu
1               5                   10                  15

Thr Leu Ser Leu Thr Cys Thr Val Ser Gly Gly Ser Val Ser Asp Tyr
                20                  25                  30

Tyr Trp Ser Trp Ile Arg Gln Pro Pro Gly Lys Gly Leu Glu Trp Ile
            35                  40                  45

Gly Tyr Ile His Ser Ser Gly Ser Thr Asp Tyr Asn Pro Ser Leu Lys
    50                  55                  60

Ser Arg Leu Thr Ile Ser Gly Asp Ala Ala Lys Lys Gln Phe Ser Leu
65                  70                  75                  80

Lys Leu Ser Ser Val Thr Ala Ala Asp Thr Ala Leu Tyr Tyr Cys Ala
                85                  90                  95

Arg Ala Gln Gly Gly Ser Arg Arg Thr Leu Asp Tyr Trp Gly Gln Gly
            100                 105                 110

Thr Leu Val Thr Val Ser Ser
        115
```

<210> SEQ ID NO 160
<211> LENGTH: 330
<212> TYPE: PRT
<213> ORGANISM: Artificial Sequence
<220> FEATURE:
<223> OTHER INFORMATION: Synthetic Construct -continued

<400> SEQUENCE: 160

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 161
<211> LENGTH: 327
<212> TYPE: PRT
<213> ORGANISM: Artificial Sequence
<220> FEATURE:
<223> OTHER INFORMATION: Synthetic Construct

<400> SEQUENCE: 161

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 162
<211> LENGTH: 107
<212> TYPE: PRT
<213> ORGANISM: Artificial Sequence
<220> FEATURE:
<223> OTHER INFORMATION: Synthetic Construct

<400> SEQUENCE: 162

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

-continued

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 163
<211> LENGTH: 16
<212> TYPE: PRT
<213> ORGANISM: Artificial Sequence
<220> FEATURE:
<223> OTHER INFORMATION: Synthetic Construct

<400> SEQUENCE: 163

Ser Ile His Asn Ser Gly Ser Thr Tyr Tyr Asn Pro Ser Leu Lys Gly
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Synthetic Construct

<400> SEQUENCE: 164

Ser Ile His Asn Lys Gly Ser Thr Tyr Tyr Asn Pro Ser Leu Lys Gly
1               5                   10                  15

<210> SEQ ID NO 165
<211> LENGTH: 4
<212> TYPE: PRT
<213> ORGANISM: Artificial Sequence
<220> FEATURE:
<223> OTHER INFORMATION: Synthetic Construct

<400> SEQUENCE: 165

Asp Gly Asp Ala
1

<210> SEQ ID NO 166
<211> LENGTH: 4
<212> TYPE: PRT
<213> ORGANISM: Artificial Sequence
<220> FEATURE:
<223> OTHER INFORMATION: Synthetic Construct

<400> SEQUENCE: 166

Asp Gly Asp Thr
1

<210> SEQ ID NO 167
<211> LENGTH: 4
<212> TYPE: PRT
<213> ORGANISM: Artificial Sequence
<220> FEATURE:
<223> OTHER INFORMATION: Synthetic Construct

<400> SEQUENCE: 167

Tyr Gly Asp Ser
1

<210> SEQ ID NO 168
```

```
<211> LENGTH: 4
<212> TYPE: PRT
<213> ORGANISM: Artificial Sequence
<220> FEATURE:
<223> OTHER INFORMATION: Synthetic Construct

<400> SEQUENCE: 168

Asn Gly Asp Ser
1

<210> SEQ ID NO 169
<211> LENGTH: 4
<212> TYPE: PRT
<213> ORGANISM: Artificial Sequence
<220> FEATURE:
<223> OTHER INFORMATION: Synthetic Construct

<400> SEQUENCE: 169

Asp Ala Asp Ser
1

<210> SEQ ID NO 170
<211> LENGTH: 13
<212> TYPE: PRT
<213> ORGANISM: Artificial Sequence
<220> FEATURE:
<223> OTHER INFORMATION: Synthetic Construct

<400> SEQUENCE: 170

Gln Phe Gly Ser Glu Thr Tyr Tyr Asn Gly Ile Tyr Pro
1               5                   10

<210> SEQ ID NO 171
<211> LENGTH: 13
<212> TYPE: PRT
<213> ORGANISM: Artificial Sequence
<220> FEATURE:
<223> OTHER INFORMATION: Synthetic Construct

<400> SEQUENCE: 171

Gln Phe Gly Ser Glu Thr Tyr Tyr Asn Gly Ile Cys Pro
1               5                   10

<210> SEQ ID NO 172
<211> LENGTH: 13
<212> TYPE: PRT
<213> ORGANISM: Artificial Sequence
<220> FEATURE:
<223> OTHER INFORMATION: Synthetic Construct

<400> SEQUENCE: 172

Gln Phe Gly Ser Glu Thr Tyr Tyr Asn Gly Ile His Pro
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Synthetic Construct

<400> SEQUENCE: 173

Gln Phe Gly Ser Glu Thr Tyr Tyr Asn Gly Ile Ser Pro
1               5                   10

<210> SEQ ID NO 174
<211> LENGTH: 13
```

<212> TYPE: PRT
<213> ORGANISM: Artificial Sequence
<220> FEATURE:
<223> OTHER INFORMATION: Synthetic Construct

<400> SEQUENCE: 174

Gln Phe Gly Ser Glu Thr Tyr Tyr Asn Gly Ile Arg Pro
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Synthetic Construct

<400> SEQUENCE: 175

Gln Phe Gly Ser Glu Thr Tyr Tyr Asn Gly Ile Ala Pro
1               5                   10

<210> SEQ ID NO 176
<211> LENGTH: 13
<212> TYPE: PRT
<213> ORGANISM: Artificial Sequence
<220> FEATURE:
<223> OTHER INFORMATION: Synthetic Construct

<400> SEQUENCE: 176

Gln Phe Gly Ser Glu Thr Tyr Tyr Asn Gly Ile Glu Pro
1               5                   10

<210> SEQ ID NO 177
<211> LENGTH: 13
<212> TYPE: PRT
<213> ORGANISM: Artificial Sequence
<220> FEATURE:
<223> OTHER INFORMATION: Synthetic Construct

<400> SEQUENCE: 177

Gln Phe Gly Ser Glu Thr Tyr Tyr Asn Gly Ile Gly Pro
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Synthetic Construct

<400> SEQUENCE: 178

Gln Phe Gly Ser Glu Thr Tyr Tyr Asn Gly Ile Lys Pro
1               5                   10

<210> SEQ ID NO 179
<211> LENGTH: 13
<212> TYPE: PRT
<213> ORGANISM: Artificial Sequence
<220> FEATURE:
<223> OTHER INFORMATION: Synthetic Construct

<400> SEQUENCE: 179

Gln Phe Gly Ser Glu Thr Tyr Tyr Asn Gly Ile Trp Pro
1               5                   10

<210> SEQ ID NO 180
<211> LENGTH: 13
<212> TYPE: PRT

```
<213> ORGANISM: Artificial Sequence
<220> FEATURE:
<223> OTHER INFORMATION: Synthetic Construct

<400> SEQUENCE: 180

Gln Phe Gly Ser Glu Thr Tyr Tyr Asn Gly Ile Val Pro
1               5                   10

<210> SEQ ID NO 181
<211> LENGTH: 13
<212> TYPE: PRT
<213> ORGANISM: Artificial Sequence
<220> FEATURE:
<223> OTHER INFORMATION: Synthetic Construct

<400> SEQUENCE: 181

Gln Phe Gly Ser Glu Thr Tyr Tyr Pro Gly Ile Asp Pro
1               5                   10

<210> SEQ ID NO 182
<211> LENGTH: 13
<212> TYPE: PRT
<213> ORGANISM: Artificial Sequence
<220> FEATURE:
<223> OTHER INFORMATION: Synthetic Construct

<400> SEQUENCE: 182

Gln Phe Gly Ser Glu Thr Tyr Tyr Asn Gly Ile Asp Pro
1               5                   10

<210> SEQ ID NO 183
<211> LENGTH: 13
<212> TYPE: PRT
<213> ORGANISM: Artificial Sequence
<220> FEATURE:
<223> OTHER INFORMATION: Synthetic Construct

<400> SEQUENCE: 183

Gln Phe Gly Ser Glu Thr Tyr Tyr Thr Gly Ile Gln Pro
1               5                   10

<210> SEQ ID NO 184
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10
<223> OTHER INFORMATION: Xaa = Pro, Arg, Gln, Ala, Asn, Phe, Trp, Val,
      Gly, or His

<400> SEQUENCE: 184

Arg Ser Ser Gln Ser Leu Leu His Ser Xaa Gly Tyr Asn Tyr Leu Asp
1               5                   10                  15

<210> SEQ ID NO 185
<211> LENGTH: 13
<212> TYPE: PRT
<213> ORGANISM: Artificial Sequence
<220> FEATURE:
<223> OTHER INFORMATION: Synthetic Construct

<400> SEQUENCE: 185

Gln Phe Gly Ser Glu Thr Tyr Tyr Ser Gly Ile Asp Pro
1               5                   10
```

-continued

```
<210> SEQ ID NO 186
<211> LENGTH: 13
<212> TYPE: PRT
<213> ORGANISM: Artificial Sequence
<220> FEATURE:
<223> OTHER INFORMATION: Synthetic Construct

<400> SEQUENCE: 186

Gln Phe Gly Ser Glu Thr Tyr Tyr Val Gly Ile Asp Pro
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Synthetic Construct

<400> SEQUENCE: 187

Gln Phe Gly Ser Glu Thr Tyr Tyr Val Gly Ile Gln Pro
1               5                   10

<210> SEQ ID NO 188
<211> LENGTH: 13
<212> TYPE: PRT
<213> ORGANISM: Artificial Sequence
<220> FEATURE:
<223> OTHER INFORMATION: Synthetic Construct

<400> SEQUENCE: 188

Gln Phe Gly Ser Glu Thr Tyr Tyr Ser Gly Ile Gln Pro
1               5                   10

<210> SEQ ID NO 189
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp, Tyr, or Asn
<220> FEATURE:
<221> NAME/KEY: VARIANT
<222> LOCATION: 2
<223> OTHER INFORMATION: Xaa = Gly or Ala
<220> FEATURE:
<221> NAME/KEY: VARIANT
<222> LOCATION: 3
<223> OTHER INFORMATION: Xaa = Asp or Thr
<220> FEATURE:
<221> NAME/KEY: VARIANT
<222> LOCATION: 4
<223> OTHER INFORMATION: Xaa = Ser, Ala, or Thr

<400> SEQUENCE: 189

Xaa Xaa Xaa Xaa
1

<210> SEQ ID NO 190
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = Ser, Pro, Thr, Asn, or Val
```

```
<220> FEATURE:
<221> NAME/KEY: VARIANT
<222> LOCATION: 12
<223> OTHER INFORMATION: Xaa = Ser, Tyr, Arg, Lys, Gln, Ala, Trp, Val,
      Gly, Cys, Asp, Glu, or His

<400> SEQUENCE: 190

Gln Phe Gly Ser Glu Thr Tyr Tyr Xaa Gly Ile Xaa Pro
1               5                   10

<210> SEQ ID NO 191
<211> LENGTH: 16
<212> TYPE: PRT
<213> ORGANISM: Artificial Sequence
<220> FEATURE:
<223> OTHER INFORMATION: Synthetic Construct

<400> SEQUENCE: 191

Arg Ser Ser Gln Ser Leu Leu His Ser Ala Gly Tyr Asn Tyr Leu Asp
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Synthetic Construct

<400> SEQUENCE: 192

Arg Ser Ser Gln Ser Leu Leu His Ser Val Gly Tyr Asn Tyr Leu Asp
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Synthetic Construct

<400> SEQUENCE: 193

Arg Ser Ser Gln Ser Leu Leu His Ser Phe Gly Tyr Asn Tyr Leu Asp
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Synthetic Construct

<400> SEQUENCE: 194

Arg Ser Ser Gln Ser Leu Leu His Ser Gly Gly Tyr Asn Tyr Leu Asp
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Synthetic Construct

<400> SEQUENCE: 195

Arg Ser Ser Gln Ser Leu Leu His Ser His Gly Tyr Asn Tyr Leu Asp
1               5                   10                  15

<210> SEQ ID NO 196
<211> LENGTH: 16
```

```
<212> TYPE: PRT
<213> ORGANISM: Artificial Sequence
<220> FEATURE:
<223> OTHER INFORMATION: Synthetic Construct

<400> SEQUENCE: 196

Arg Ser Ser Gln Ser Leu Leu His Ser Gln Gly Tyr Asn Tyr Leu Asp
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Synthetic Construct

<400> SEQUENCE: 197

Arg Ser Ser Gln Ser Leu Leu His Ser Trp Gly Tyr Asn Tyr Leu Asp
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: Synthetic Construct

<400> SEQUENCE: 198

Arg Ser Ser Gln Ser Leu Leu His Ser Pro Gly Tyr Asn Tyr Leu Asp
1               5                   10                  15

<210> SEQ ID NO 199
<211> LENGTH: 9
<212> TYPE: PRT
<213> ORGANISM: Artificial Sequence
<220> FEATURE:
<223> OTHER INFORMATION: Synthetic Construct

<400> SEQUENCE: 199

Leu Gln Ala Asp Ser Leu Pro His Thr
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic Construct

<400> SEQUENCE: 200

Leu Gln Ala Tyr Ser Leu Pro His Thr
1               5

<210> SEQ ID NO 201
<211> LENGTH: 9
<212> TYPE: PRT
<213> ORGANISM: Artificial Sequence
<220> FEATURE:
<223> OTHER INFORMATION: Synthetic Construct

<400> SEQUENCE: 201

Leu Gln Ala Leu Ser Leu Pro His Thr
1               5

<210> SEQ ID NO 202
<211> LENGTH: 9
<212> TYPE: PRT
```

<213> ORGANISM: Artificial Sequence
<220> FEATURE:
<223> OTHER INFORMATION: Synthetic Construct

<400> SEQUENCE: 202

Leu Gln Ala Gly Ser Leu Pro His Thr
1               5

<210> SEQ ID NO 203
<211> LENGTH: 9
<212> TYPE: PRT
<213> ORGANISM: Artificial Sequence
<220> FEATURE:
<223> OTHER INFORMATION: Synthetic Construct

<400> SEQUENCE: 203

Leu Gln Ala His Ser Leu Pro His Thr
1               5

<210> SEQ ID NO 204
<211> LENGTH: 9
<212> TYPE: PRT
<213> ORGANISM: Artificial Sequence
<220> FEATURE:
<223> OTHER INFORMATION: Synthetic Construct

<400> SEQUENCE: 204

Leu Gln Ala Ala Ser Leu Pro His Thr
1               5

<210> SEQ ID NO 205
<211> LENGTH: 9
<212> TYPE: PRT
<213> ORGANISM: Artificial Sequence
<220> FEATURE:
<223> OTHER INFORMATION: Synthetic Construct

<400> SEQUENCE: 205

Leu Gln Ala Cys Ser Leu Pro His Thr
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic Construct

<400> SEQUENCE: 206

Leu Gln Ala Glu Ser Leu Pro His Thr
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic Construct

<400> SEQUENCE: 207

Leu Gln Ala Gln Ser Leu Pro His Thr
1               5

<210> SEQ ID NO 208
<211> LENGTH: 9
<212> TYPE: PRT
<213> ORGANISM: Artificial Sequence
<220> FEATURE:
<223> OTHER INFORMATION: Synthetic Construct

<400> SEQUENCE: 208

Leu Gln Ala Arg Ser Leu Pro His Thr
1               5

<210> SEQ ID NO 209
<211> LENGTH: 9
<212> TYPE: PRT
<213> ORGANISM: Artificial Sequence
<220> FEATURE:
<223> OTHER INFORMATION: Synthetic Construct

<400> SEQUENCE: 209

Leu Gln Ala Thr Ser Leu Pro His Thr
1               5

<210> SEQ ID NO 210
<211> LENGTH: 9
<212> TYPE: PRT
<213> ORGANISM: Artificial Sequence
<220> FEATURE:
<223> OTHER INFORMATION: Synthetic Construct

<400> SEQUENCE: 210

Leu Gln Ala Val Ser Leu Pro His Thr
1               5

<210> SEQ ID NO 211
<211> LENGTH: 9
<212> TYPE: PRT
<213> ORGANISM: Artificial Sequence
<220> FEATURE:
<223> OTHER INFORMATION: Synthetic Construct

<400> SEQUENCE: 211

Leu Gln Ala Trp Ser Leu Pro His Thr
1               5

<210> SEQ ID NO 212
<211> LENGTH: 9
<212> TYPE: PRT
<213> ORGANISM: Artificial Sequence
<220> FEATURE:
<223> OTHER INFORMATION: Synthetic Construct

<400> SEQUENCE: 212

Leu Gln Ala Pro Ser Leu Pro His Thr
1               5

<210> SEQ ID NO 213
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser, Gln, or Lys

<400> SEQUENCE: 213

Ser Ile His Asn Xaa Gly Ser Thr Tyr Tyr Asn Pro Ser Leu Lys Gly
1               5                   10                  15

<210> SEQ ID NO 214

```
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8
<223> OTHER INFORMATION: Xaa = Tyr or Arg

<400> SEQUENCE: 214

Met Gln Ala Leu Gln Thr Pro Xaa Thr
1               5
```

ANTIBODIES SPECIFICALLY RECOGNIZING *PSEUDOMONAS* Psl AND USES THEREOF

SUBMISSION OF SEQUENCE LISTING ON ASCII TEXT FILE

The content of the following submission on ASCII text file is incorporated herein by reference in its entirety: a computer readable form (CRF) of the Sequence Listing (file name: PSL_202007138989_SEQLIST.TXT, date recorded: Jul. 13, 2020, size: 116 KB).

FIELD OF THE APPLICATION

This application pertains to antibodies that specifically recognize Psl from *Pseudomonas aeruginosa*, and methods of manufacture and uses thereof, including methods of treating and preventing *Pseudomonas* infections.

BACKGROUND OF THE APPLICATION

*Pseudomonas aeruginosa* is an obligately aerobic gram-negative *Bacillus* being widely existing in the natural world. Although its pathogenicity is usually low, it is a pathogen that causes opportunistic infections, often occurring in patients suffering from various pre-existing diseases such as cancer, diabetes, immunodeficiency diseases and patients administered with pharmaceuticals exhibiting immune-inhibitory action. Patients with breached skin mucous membrane are prone to *P. aeruginosa* infections while it also poses considerable risk to patients with chronic structural lung diseases (such as COPD or cystic fibrosis). *P. aeruginosa* may often cause pneumonia, urinary tract infection, sepsis and the like, and often leading to severe results. Up to 10% of nosocomial infections are attributed to *P. aeruginosa*, with mortality rates approaching 40% in patients with *P. aeruginosa* bacteremia. In clinical fields, *P. aeruginosa* infection is considered as one of the most difficult infections to be treated not only because *P. aeruginosa* has inherently low sensitivity to existent antibiotics, but also because of its high tendency to acquire resistance to various antibiotics. Thus, the strategy of developing an arsenal of antibiotics has limited merits in combating *P. aeruginosa* infections.

*Pseudomonas aeruginosa* is a major cause of hospital-acquired infections, particularly in mechanically ventilated patients, and it is the leading cause of death in cystic fibrosis patients. One key component of the *P. aeruginosa* biofilm matrix is the polysaccharide Psl, which is produced by proteins encoded within the polysaccharide synthesis locus. Psl is both cell-free and surface-associated. The structure of cell-free Psl is composed of a repeating pentasaccharide of D-mannose, L-rhamnose, and D-glucose. Since Psl serves both structural and protective functions during biofilm formation, and is also known to protect biofilms from antibiotics, by chemical binding, and from the immune system by an unknown mechanism, it may be an ideal target for novel therapeutic options (Ray VA. et al. Anti-Psl Targeting of *Pseudomonas aeruginosa* Biofilms for Neutrophil-Mediated Disruption. Sci Rep. 2017). Human monoclonal antibodies (mAbs) targeting Psl, for example, Wapr-001, Wapr-016, Cam-003 or its derivative, psl0096 were described (DiGiandomenico, A. et al. Identification of broadly protective human antibodies to *Pseudomonas aeruginosa* exopolysaccharide Psl by phenotypic screening. J Exp Med 209, 1273-1287; Valerie A. Ray, et al, Anti-Psl targeting of

2

*Pseudomonas aeruginosa* biofilms for neutrophil mediated disruption, Scientific Reports7, Article number: 16065 (2017)).

The disclosures of all publications, patents, patent applications and published patent applications referred to herein are hereby incorporated herein by reference in their entirety.

BRIEF SUMMARY OF THE APPLICATION

The present application provides an isolated antibody or antigen binding fragment that specifically binds to *Pseudomonas* Psl, and methods of use thereof for preventing and treating *Pseudomonas* infections.

In one aspect, the present application provides an isolated antibody or antigen binding fragment thereof which specially binds to *Pseudomonas* Psl comprising: a $V_H$ comprising an HC-CDR1 comprising the amino acid sequence of any one of SEQ ID NOs: 2-3, and 5-12, or a variant thereof comprising up to about 3 amino acid substitutions; an HC-CDR2 comprising the amino acid sequence of any one of SEQ ID NOs: 14-15, and 17-23, or a variant thereof comprising up to about 3 amino acid substitutions; and an HC-CDR3 comprising the amino acid sequence of any one of SEQ ID NOs: 25-26, and 28-34, or a variant thereof comprising up to about 3 amino acid substitutions.

In one aspect, the present application provides an isolated antibody or antigen binding fragment thereof which specially binds to *Pseudomonas* Psl comprising: a $V_L$ comprising an LC-CDR1 comprising the amino acid sequence of any one of SEQ ID NOs: 38-39, and 41-49, or a variant thereof comprising up to about 3 amino acid substitutions; an LC-CDR2 comprising the amino acid sequence of any one of SEQ ID NOs: 52-53, and 55-61, or a variant thereof comprising up to about 3 amino acid substitutions; and an LC-CDR3 comprising the amino acid sequence of any one of SEQ ID NOs: 63-64, 66-68, and 70-75, or a variant thereof comprising up to about 3 amino acid substitutions.

In one aspect, the present application provides an isolated antibody or antigen binding fragment thereof which specially binds to *Pseudomonas* Psl comprising: a $V_H$ comprising an HC-CDR1 comprising the amino acid sequence of any one of SEQ ID NOs: 2-3, and 5-12, or a variant thereof comprising up to about 3 amino acid substitutions; an HC-CDR2 comprising the amino acid sequence of any one of SEQ ID NOs: 14-15, and 17-23, or a variant thereof comprising up to about 3 amino acid substitutions; and an HC-CDR3 comprising the amino acid sequence of any one of SEQ ID NOs: 25-26, and 28-34, or a variant thereof comprising up to about 3 amino acid substitutions; and a $V_L$ comprising an LC-CDR1 comprising the amino acid sequence of any one of SEQ ID NOs: 38-39, and 41-49, or a variant thereof comprising up to about 3 amino acid substitutions; an LC-CDR2 comprising the amino acid sequence of any one of SEQ ID NOs: 52-53, and 55-61, or a variant thereof comprising up to about 3 amino acid substitutions; and an LC-CDR3 comprising the amino acid sequence of any one of SEQ ID NOs: 63-64, 66-68, and 70-75, or a variant thereof comprising up to about 3 amino acid substitutions.

In one aspect, the present application provides an isolated antibody or antigen binding fragment thereof which specially binds to *Pseudomonas* Psl comprising: (i) a $V_H$ comprising an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; (ii) a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; (iii) a $V_H$ comprising an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28, or a variant thereof comprising up to about 5 amino acid substitutions in the HC-CDRs; (iv) a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29, or a variant thereof comprising up to about 5 amino acid substitutions in the HC-CDRs; (v) a $V_H$ comprising an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; (vi) a $V_H$ comprising an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30, or a variant thereof comprising up to about 5 amino acid substitutions in the HC-CDRs; (vii) a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; (viii) a $V_H$ comprising an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31, or a variant thereof comprising up to about 5 amino acid substitutions in the HC-CDRs; (ix) a $V_H$ comprising an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32, or a variant thereof comprising up to about 5 amino acid substitutions in the HC-CDRs; (x) a $V_H$ comprising an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33, or a variant thereof comprising up to about 5 amino acid substitutions in the HC-CDRs; or (xi) a $V_H$ comprising an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34, or a variant thereof comprising up to about 5 amino acid substitutions in the HC-CDRs.

In one aspect, the present application provides an isolated antibody or antigen binding fragment thereof which specially binds to *Pseudomonas* Psl comprising: (i) a $V_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63, or a variant thereof comprising up to about 5 amino acid substitutions in the LC-CDRs; (ii) a $V_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64, or a variant thereof comprising up to about 5 amino acid substitutions in the LC-CDRs; (iii) a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66, or a variant thereof comprising up to about 5 amino acid substitutions in the LC-CDRs; (iv) a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67, or a variant thereof comprising up to about 5 amino acid substitutions in the LC-CDRs; (v) a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68, or a variant thereof comprising up to about 5 amino acid substitutions in the LC-CDRs; (vi) a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70, or a variant thereof comprising up to about 5 amino acid substitutions in the LC-CDRs; (vii) a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71, or a variant thereof comprising up to about 5 amino acid substitutions in the LC-CDRs; (viii) a $V_L$ comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72, or a variant thereof comprising up to about 5 amino acid substitutions in the LC-CDRs; (ix) a $V_L$ comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73, or a variant thereof comprising up to about 5 amino acid substitutions in the LC-CDRs; (x) a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74, or a variant thereof comprising up to about 5 amino acid substitutions in the LC-CDRs; or (xi) a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75, or a variant thereof comprising up to about 5 amino acid substitutions in the LC-CDRs.

In one aspect, the present application provides an isolated antibody or antigen binding fragment thereof which specially binds to *Pseudomonas* Psl comprising: (i) a $V_H$ comprising an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; and a $V_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63, or a variant thereof comprising up to about 5 amino acid substitutions in the LC-CDRs; (ii) a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; and a $V_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64, or a variant thereof comprising up to about 5 amino acid substitutions in the LC-CDRs; (iii) a $V_H$ comprising an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28, or a variant thereof comprising up to about 5 amino acid substitutions in the HC-CDRs; and a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66, or a variant thereof comprising up to about 5 amino acid substitutions in the LC-CDRs; (iv) a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29, or a variant thereof comprising up to about 5 amino acid substitutions in the HC-CDRs; and a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67, or a variant thereof comprising up to about 5 amino acid substitutions in the LC-CDRs; (v) a $V_H$ comprising an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; and a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68, or a variant thereof comprising up to about 5 amino acid substitutions in the LC-CDRs; (vi) a $V_H$ comprising an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30, or a variant thereof comprising up to about 5 amino acid substitutions in the HC-CDRs; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70, or a variant thereof comprising up to about 5 amino acid substitutions in the LC-CDRs; (vii) a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; and a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71, or a variant thereof comprising up to about 5 amino acid substitutions in the LC-CDRs; (viii) a $V_H$ comprising an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31, or a variant thereof comprising up to about 5 amino acid substitutions in the HC-CDRs; and a $V_L$ comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72, or a variant thereof comprising up to about 5 amino acid substitutions in the LC-CDRs; (ix) a $V_H$ comprising an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32, or a variant thereof comprising up to about 5 amino acid substitutions in the HC-CDRs; and a $V_L$ comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73, or a variant thereof comprising up to about 5 amino acid substitutions in the LC-CDRs; (x) a $V_H$ comprising an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33, or a variant thereof comprising up to about 5 amino acid substitutions in the HC-CDRs; and a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74, or a variant thereof comprising up to about 5 amino acid substitutions in the LC-CDRs; or (xi) a $V_H$ comprising an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34, or a variant thereof comprising up to about 5 amino acid substitutions in the HC-CDRs; and a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75, or a variant thereof comprising up to about 5 amino acid substitutions in the LC-CDRs.

In one aspect, the present application provides an isolated antibody or antigen binding fragment thereof which specially binds to *Pseudomonas* Psl comprising: a $V_H$ comprising an HC-CDR1, an HC-CDR2, and an HC-CDR3 of the $V_H$ comprising the amino acid sequence of any one of SEQ ID NOs: 80-81, 83-90, and 159; and a $V_L$ comprising an LC-CDR1, an LC-CDR2, and an LC-CDR3 of the $V_L$ comprising the amino acid sequence of any one of SEQ ID NOs: 92-93, 95-97, and 99-104.

In one aspect, the present application provides an isolated antibody or antigen binding fragment thereof which specially binds to *Pseudomonas* Psl comprising: a $V_H$ comprising the amino acid sequence of any one of SEQ ID NOs: 80-81, 83-90, and 159 or a variant thereof having at least about 90% (for example at least about any of 91%, 92%, 93%, 94%, 95%, 96%, 97%, 98%, or 99%) sequence identity to the amino acid sequence of any one of SEQ ID NOs: 80-81, 83-90, and 159; and a $V_L$ comprising the amino acid sequence of any one of SEQ ID NOs: 92-93, 95-97, and 99-104 or a variant thereof having at least about 90% (for example at least about any of 91%, 92%, 93%, 94%, 95%, 96%, 97%, 98%, or 99%) sequence identity to the amino acid sequence of any one of SEQ ID NOs: 92-93, 95-97, and 99-104.

In one aspect, the present application provides an isolated antibody or antigen binding fragment thereof which specially binds to *Pseudomonas* Psl comprising: a $V_H$ comprising the amino acid sequence of any one of SEQ ID NOs: 80-81, 83-90, and 159; and a $V_L$ comprising the amino acid sequence of any one of SEQ ID NOs: 92-93, 95-97, and 99-104.

In one aspect, the present application provides an isolated antibody or antigen binding fragment thereof which specially binds to *Pseudomonas* Psl comprising: (i) a $V_H$ comprising the amino acid sequence of SEQ ID NO: 80 and a $V_L$ comprising the amino acid sequence of SEQ ID NO: 92; (ii) a $V_H$ comprising the amino acid sequence of SEQ ID NO: 81 and a $V_L$ comprising the amino acid sequence of SEQ ID NO: 93; (iii) a $V_H$ comprising the amino acid sequence of SEQ ID NO: 83 and a $V_L$ comprising the amino acid sequence of SEQ ID NO: 95; (iv) a $V_H$ comprising the amino acid sequence of SEQ ID NO: 84 and a $V_L$ comprising the amino acid sequence of SEQ ID NO: 96; (v) a $V_H$ comprising the amino acid sequence of SEQ ID NO: 85 and a $V_L$ comprising the amino acid sequence of SEQ ID NO: 97; (vi) a $V_H$ comprising the amino acid sequence of SEQ ID NO: 86 and a $V_L$ comprising the amino acid sequence of SEQ ID NO: 99; (vii) a $V_H$ comprising the amino acid sequence of SEQ ID NO: 81 and a $V_L$ comprising the amino acid sequence of SEQ ID NO: 100; (viii) a $V_H$ comprising the amino acid sequence of SEQ ID NO: 87 and a $V_L$ comprising the amino acid sequence of SEQ ID NO: 101; (ix) a $V_H$ comprising the amino acid sequence of SEQ ID NO: 88 and a $V_L$ comprising the amino acid sequence of SEQ ID NO: 102; (x) a $V_H$ comprising the amino acid sequence of SEQ ID NO: 89 and a $V_L$ comprising the amino acid sequence of SEQ ID NO: 103; (xi) a $V_H$ comprising the amino acid sequence of SEQ ID NO: 90 and a $V_L$ comprising the amino acid sequence of SEQ ID NO: 104; or (xii) a $V_H$ comprising the amino acid sequence of SEQ ID NO: 159 and a $V_L$ comprising the amino acid sequence of SEQ ID NO: 95.

In one aspect, the present application provides an isolated antibody or antigen binding fragment thereof which specially binds to *Pseudomonas* Psl comprising: a heavy chain variable domain ($V_H$) comprising a heavy chain complementarity determining region (HC-CDR) 1 comprising IHSVH (SEQ ID NO: 4), or a variant thereof comprising up to about 3 amino acid substitutions; an HC-CDR2 comprising TIISSGTTTTYAQSFQD (SEQ ID NO: 16), or a variant thereof comprising up to about 3 amino acid substitutions; and an HC-CDR3 comprising $X_1X_2X_3X_4$(SEQ ID NO: 189), or a variant thereof comprising up to about 3 amino acid substitutions, wherein $X_1$ is D, Y or N, $X_2$ is G, or A, $X_3$ is D, or T, $X_4$ is S, A, or T; and a light chain variable domain ($V_L$) comprising a light chain complementarity determining region (LC-CDR) 1 comprising RASQGISS-WLA (SEQ ID NO: 40), or a variant thereof comprising up to about 3 amino acid substitutions; an LC-CDR2 comprising HASTLES (SEQ ID NO: 54), or a variant thereof comprising up to about 3 amino acid substitutions; and an LC-CDR3 comprising LQAX$_1$SLPHT (SEQ ID NO: 158), or a variant thereof comprising up to about 3 amino acid substitutions, wherein $X_1$ is N, D, Y, F, P, G, K, H, A, C, E, Q, R, S, T, V, W or L.

In one aspect, the present application provides an isolated antibody or antigen binding fragment thereof which specially binds to *Pseudomonas* Psl comprising: a heavy chain variable domain ($V_H$) comprising a heavy chain complementarity determining region (HC-CDR) 1 comprising IHSVH (SEQ ID NO: 4); an HC-CDR2 comprising TIIS-SGTTTTYAQSFQD (SEQ ID NO: 16); and an HC-CDR3 comprising an amino acid sequence selected from a group of SEQ ID NO: 27, SEQ ID NO: 35, and SEQ ID NOs: 165-169; and a light chain variable domain ($V_L$) comprising a light chain complementarity determining region (LC-CDR) 1 comprising RASQGISSWLA (SEQ ID NO: 40); an LC-CDR2 comprising HASTLES (SEQ ID NO: 54); and an LC-CDR3 comprising an amino acid sequence selected from a group of SEQ ID NO: 65, SEQ ID NOs: 76-78, and SEQ ID NOs: 199-212.

In one aspect, the present application provides an isolated antibody or antigen binding fragment thereof which specially binds to *Pseudomonas* Psl comprising: (i) a $V_H$ comprising an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65, or a variant thereof comprising up to about 5 amino acid substitutions in the LC-CDRs; (ii) a $V_H$ comprising an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35, or a variant thereof comprising up to about 5 amino acid substitutions in the HC-CDRs; and a $V_L$ comprising an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78, or a variant thereof comprising up to about 5 amino acid substitutions in the LC-CDRs; (iii) a $V_H$ comprising an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35, or a variant thereof comprising up to about 5 amino acid substitutions in the HC-CDRs; and a $V_L$ comprising an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 76, or a variant thereof comprising up to about 5 amino acid substitutions in the LC-CDRs; or (iv) a $V_H$ comprising an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35, or a variant thereof comprising up to about 5 amino acid substitutions in the HC-CDRs; and a $V_L$ comprising an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 77, or a variant thereof comprising up to about 5 amino acid substitutions in the LC-CDRs.

In one aspect, the present application provides an isolated antibody or antigen binding fragment thereof which specially binds to *Pseudomonas* Psl comprising: (i) a $V_H$ comprising the amino acid sequence of SEQ ID NOs: 82 or a variant thereof having at least about 90% (for example at least about any of 91%, 92%, 93%, 94%, 95%, 96%, 97%, 98%, or 99%) sequence identity to the amino acid sequence of SEQ ID NOs: 82, and a $V_L$ comprising the amino acid sequence of SEQ ID NO: 94 or a variant thereof having at least about 90% (for example at least about any of 91%, 92%, 93%, 94%, 95%, 96%, 97%, 98%, or 99%) sequence identity to the amino acid sequence of SEQ ID NOs: 94; (ii) a $V_H$ comprising the amino acid sequence of any one of SEQ ID NOs: 105-110 or a variant thereof having at least about 90% (for example at least about any of 91%, 92%, 93%, 94%, 95%, 96%, 97%, 98%, or 99%) sequence identity to the amino acid sequence of any one of SEQ ID NOs: 105-110, and a $V_L$ comprising the amino acid sequence of SEQ ID NO: 94 or a variant thereof having at least about 90% (for example at least about any of 91%, 92%, 93%, 94%, 95%, 96%, 97%, 98%, or 99%) sequence identity to the amino acid sequence of SEQ ID NO: 94; (iii) a $V_H$ comprising the amino acid sequence of SEQ ID NO: 82 or a variant thereof having at least about 90% (for example at least about any of 91%, 92%, 93%, 94%, 95%, 96%, 97%, 98%, or 99%) sequence identity to the amino acid sequence of SEQ ID NO: 82, and a $V_L$ comprising the amino acid sequence of any one of SEQ ID NO: 111-127 or a variant thereof having at least about 90% (for example at least about any of 91%, 92%, 93%, 94%, 95%, 96%, 97%, 98%, or 99%) sequence identity to the amino acid sequence of any one of SEQ ID NO: 111-127; (iv) a $V_H$ comprising the amino acid sequence of SEQ ID NO: 107 or a variant thereof having at least about 90% (for example at least about any of 91%, 92%, 93%, 94%, 95%, 96%, 97%, 98%, or 99%) sequence identity to the amino acid sequence of SEQ ID NO: 107, and a $V_L$ comprising the amino acid sequence of SEQ ID NO: 113 or a variant thereof having at least about 90% (for example at least about any of 91%, 92%, 93%, 94%, 95%, 96%, 97%, 98%, or 99%) sequence identity to the amino acid sequence of SEQ ID NO: 113; (v) a $V_H$ comprising the amino acid sequence of SEQ ID NO: 107 or a variant thereof having at least about 90% (for example at least about any of 91%, 92%, 93%, 94%, 95%, 96%, 97%, 98%, or 99%) sequence identity to the amino acid sequence of SEQ ID NO: 107, and a $V_L$ comprising the amino acid sequence of SEQ ID NO: 123 or a variant thereof having at least about 90% (for example at least about any of 91%, 92%, 93%, 94%, 95%, 96%, 97%, 98%, or 99%) sequence identity to the amino acid sequence of SEQ ID NO: 123; or (vi) a $V_H$ comprising the amino acid sequence of SEQ ID NO: 107 or a variant thereof having at least about 90% (for example at least about any of 91%, 92%, 93%, 94%, 95%, 96%, 97%, 98%, or 99%) sequence identity to the amino acid sequence of SEQ ID NO: 107, and a $V_L$ comprising the amino acid sequence of SEQ ID NO: 116 or a variant thereof having at least about 90% (for example at least about any of 91%, 92%, 93%, 94%, 95%, 96%, 97%, 98%, or 99%) sequence identity to the amino acid sequence of SEQ ID NO: 116.

In one aspect, the present application provides an isolated antibody or antigen binding fragment thereof which specially binds to *Pseudomonas* Psl comprising: a heavy chain variable domain ($V_H$) comprising a heavy chain complementarity determining region (HC-CDR) 1 comprising SSGDYWG (SEQ ID NO: 1), or a variant thereof comprising up to about 3 amino acid substitutions; an HC-CDR2 comprising SINX$_1$GSTYYNPSLKG (SEQ ID NO: 213), or a variant thereof comprising up to about 3 amino acid substitutions, wherein X$_1$ is S, K, or Q; and an HC-CDR3 comprising QFGSETYYX$_1$GIX$_2$P (SEQ ID NO: 190), or a variant thereof comprising up to about 3 amino acid substitutions, wherein X$_1$ is N, S, V, T, or P, X$_2$ is D, Y, C, H, S, R, A, E, G, K, W, V, or Q; and a light chain variable domain ($V_L$) comprising a light chain complementarity determining region (LC-CDR) 1 comprising RSSQSLLHSX$_1$GYNYLD (SEQ ID NO: 184), or a variant thereof comprising up to about 3 amino acid substitutions, wherein X$_1$ is N, A, V, F, R, G, H, Q, W, or P; an LC-CDR2 comprising LGSNRAS (SEQ ID NO: 51), or a variant thereof comprising up to about 3 amino acid substitutions; and an LC-CDR3 comprising MQALQTPX$_1$T (SEQ ID NO: 214), wherein X$_1$ is R or Y, or a variant thereof comprising up to about 3 amino acid substitutions.

In one aspect, the present application provides an isolated antibody or antigen binding fragment thereof which specially binds to *Pseudomonas* Psl comprising: a heavy chain variable domain ($V_H$) comprising a heavy chain complementarity determining region (HC-CDR) 1 comprising SSGDYWG (SEQ ID NO: 1); an HC-CDR2 comprising an amino acid sequence selected from the group of SEQ ID NO:13, and SEQ ID NOs:163-164; and an HC-CDR3 comprising an amino acid sequence selected from the group of SEQ ID NO: 24, SEQ ID NO: 36, SEQ ID NOs: 170-183, and SEQ ID NOs: 185-188; and a light chain variable domain ($V_L$) comprising a light chain complementarity determining region (LC-CDR) 1 comprising an amino acid sequence selected from the group of SEQ ID NO: 37, SEQ ID NO: 50, and SEQ ID NOs: 191-198; an LC-CDR2 comprising LGSNRAS (SEQ ID NO: 51); and an LC-CDR3 comprising an amino acid sequence selected from the group of SEQ ID NO: 62 and SEQ ID NO: 69.

In one aspect, the present application provides an isolated antibody or antigen binding fragment thereof which specially binds to *Pseudomonas* Psl comprising: (i) a $V_H$ comprising an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 24, or a variant thereof comprising up to about 5 amino acid substitutions in the HC-CDRs; and a $V_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs; (ii) a $V_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36, or a variant thereof comprising up to about 5 amino acid substitutions in the HC-CDRs; and a $V_L$ comprising an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs; (iii) a $V_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs; or (iv) a $V_H$ comprising an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 183, or a variant thereof comprising up to about 5 amino acid substitutions in the HC-CDRs; and a $V_L$ comprising an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In one aspect, the present application provides an isolated antibody or antigen binding fragment thereof which specially binds to *Pseudomonas* Psl comprising: (i) a $V_H$ comprising the amino acid sequence of SEQ ID NOs: 79 or a variant thereof having at least about 90% (for example at least about any of 91%, 92%, 93%, 94%, 95%, 96%, 97%, 98%, or 99%) sequence identity to the amino acid sequence of SEQ ID NO:79, and a $V_L$ comprising the amino acid sequence of SEQ ID NO: 91 or a variant thereof having at least about 90% (for example at least about any of 91%, 92%, 93%, 94%, 95%, 96%, 97%, 98%, or 99%) sequence identity to the amino acid sequence of SEQ ID NO:91; (ii) a $V_H$ comprising the amino acid sequence of any one of SEQ ID NOs: 128-139, SEQ ID NOs: 149-151, SEQ ID NOs: 154-155 or a variant thereof having at least about 90% (for example at least about any of 91%, 92%, 93%, 94%, 95%, 96%, 97%, 98%, or 99%) sequence identity to the amino acid sequence of any one of SEQ ID NOs: 128-139, SEQ ID NOs: 149-151, SEQ ID NOs:154-155, and a $V_L$ comprising the amino acid sequence of SEQ ID NO: 91 or a variant thereof having at least about 90% (for example at least about any of 91%, 92%, 93%, 94%, 95%, 96%, 97%, 98%, or 99%) sequence identity to the amino acid sequence of SEQ ID NO: 91; (iii) a $V_H$ comprising the amino acid sequence of SEQ ID NO: 151 or a variant thereof having at least about 90% (for example at least about any of 91%, 92%, 93%, 94%, 95%, 96%, 97%, 98%, or 99%) sequence identity to the amino acid sequence of SEQ ID NO: 151, and a $V_L$ comprising the amino acid sequence of any one of SEQ ID NOs: 140-148 or a variant thereof having at least about 90% (for example at least about any of 91%, 92%, 93%, 94%, 95%, 96%, 97%, 98%, or 99%) sequence identity to the amino acid sequence of any one of SEQ ID NOs: 140-148; (iv) a $V_H$ comprising the amino acid sequence of any one of SEQ ID NO: 132, SEQ ID NO:149, SEQ ID NOs: 152-153, SEQ ID NOs: 156-157 or a variant thereof having at least about 90% (for example at least about any of 91%, 92%, 93%, 94%, 95%, 96%, 97%, 98%, or 99%) sequence identity to the amino acid sequence of any one of SEQ ID NO: 132, SEQ ID NO:149, SEQ ID NOs: 152-153, SEQ ID NOs: 156-157, and a $V_L$ comprising the amino acid sequence of SEQ ID NO: 143 or a variant thereof having at least about 90% (for example at least about any of 91%, 92%, 93%, 94%, 95%, 96%, 97%, 98%, or 99%) sequence identity to the amino acid sequence of SEQ ID NO: 143; or (v) a $V_H$ comprising the amino acid sequence of SEQ ID NO: 151 or a variant thereof having at least about 90% (for example at least about any of 91%, 92%, 93%, 94%, 95%, 96%, 97%, 98%, or 99%) sequence identity to the amino acid sequence of SEQ ID NO: 151, and a $V_L$ comprising the amino acid sequence of SEQ ID NO: 98 or a variant thereof having at least about 90% (for example at least about any of 91%, 92%, 93%, 94%, 95%, 96%, 97%, 98%, or 99%) sequence identity to the amino acid sequence of SEQ ID NO: 98.

In some embodiments, there is provided an isolated antibody or antigen binding fragment thereof which specially binds to *Pseudomonas* Psl competitively with any one of the antibodies or antigen binding fragments thereof which specially binds to *Pseudomonas* Psl described above. In some embodiments, there is provided an isolated antibody or antigen binding fragment thereof which specially binds to *Pseudomonas* Psl that specifically binds to the same epitope as any one of the antibodies or antigen binding fragments thereof which specially binds to *Pseudomonas* Psl described above.

In some embodiments according to any one of the isolated antibodies or antigen binding fragments thereof which specially binds to *Pseudomonas* Psl described above, comprises an Fc fragment. In some embodiments, the isolated antibody or antigen binding fragment thereof which specially binds to *Pseudomonas* Psl is a full-length IgG antibody. In some embodiments, the isolated antibody or antigen binding fragment thereof which specially binds to *Pseudomonas* Psl is a full-length IgG1 or IgG4 antibody. In some embodiments, the isolated antibody or antigen binding fragment thereof which specially binds to *Pseudomonas* Psl is chimeric, human, or humanized. In some embodiments, the isolated antibody or antigen binding fragment thereof which specially binds to *Pseudomonas* Psl is an antigen binding fragment selected from the group consisting of a Fab, a Fab', a F(ab)'2, a Fab'-SH, a single-chain Fv (scFv), an Fv fragment, a dAb, a Fd or a diabody.

In some embodiments, there is provided an isolated nucleic acid molecule(s) that encodes any one of the antibodies or antigen binding fragments thereof which specially binds to *Pseudomonas* Psl described above. In some embodiments, there is provided a vector comprising any one of the nucleic acid molecules described above. In some embodiments, there is provided a host cell comprising any one of the isolated antibodies or antigen binding fragments thereof which specially binds to *Pseudomonas* Psl described above, any one of the nucleic acid molecules described above, or any one of the vectors described above. In some embodiments, there is provided a method of producing an isolated antibody or antigen binding fragment thereof which specially binds to *Pseudomonas* Psl, comprising: a) culturing any one of the host cells described above under conditions effective to express the antibody or antigen binding fragment thereof which specially binds to *Pseudomonas* Psl; and b) obtaining the expressed antibody or antigen binding fragment thereof which specially binds to *Pseudomonas* Psl from the host cell.

In some embodiments, there is provided a method of preventing or treating a disease or condition in an individual in need thereof, comprising administering to the individual an effective amount of antibody or antigen binding fragment thereof which specially binds to *Pseudomonas* Psl described above, or a pharmaceutical composition comprising an antibody or antigen binding fragment thereof which specially binds to *Pseudomonas* Psl described above. In some embodiments, use of the antibody or antigen binding fragment thereof which specially binds to *Pseudomonas* Psl according to any one described above, or a pharmaceutical composition comprising an antibody or antigen binding fragment thereof which specially binds to *Pseudomonas* Psl in the manufacture of a medicament for treating a disease or condition. In some embodiments, the disease or condition is a pathogenic infection. In some embodiments, the infection is a gram-negative bacterial infection. In some embodiments, the bacterium is *Pseudomonas aeruginosa*. In some embodiments, the disease or condition comprises one or more symptoms caused by *Pseudomonas aeruginosa* infection. In some embodiments, the symptom comprises one or more of fever, chills, fatigues, muscle, and joint pain, swelling of joints, headache, diarrhea, skin rashes, pus in wounds, bacteremia, acute pneumonia, or intraperitoneal infection.

In some embodiments according to any one of the methods of treatment described above, the method further comprises administering one or more therapeutic agents. In some embodiments, at least one of the therapeutic agents is an antibiotic. In some embodiments, the antibiotic is one or more of Imipenem, Tobramycin, Ciprofloxacin, Meropenem or Aztreonam.

Also provided are pharmaceutical compositions, kits and articles of manufacture comprising any one of the antibody or antigen binding fragment thereof which specially binds to *Pseudomonas* Psl, nucleic acids, vectors, isolated host cells described above.

BRIEF DESCRIPTION OF THE DRAWINGS

FIG. 12 shows the pharmacokinetic profiles in rats for the anti-Psl antibodies 3F12, 7H9-m23, P59-m21 and the reference antibody psl0096, when administered intravenously at 3 mg/kg dose.

DETAILED DESCRIPTION OF THE APPLICATION

Figure 1A:
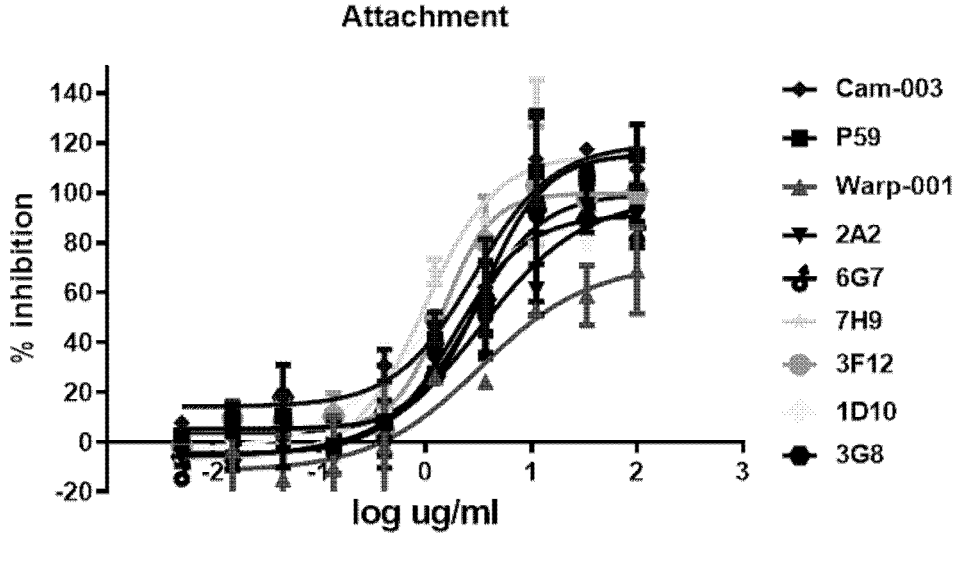
FIGS. 1A and 1B show the ability of the anti-Psl antibodies in inhibiting cell attachment of *P. aeruginosa* to A549 cells compared to the reference antibody Wapr-001 or Cam-003.

The present application in one aspect provides antibody or antigen binding fragment thereof which specially binds to *Pseudomonas* Psl. By using a combination of selections on scFv phage libraries, affinity maturation and appropriately designed biochemical and biological assays, we have identified highly potent antibody molecules that specially bind to Psl which inhibit the attachment of *Pseudomonas aeruginosa* to A549 cells and promote OPK of *Pseudomonas aeruginosa*, and provide both therapeutic and prophylactic protection in vivo against *Pseudomonas aeruginosa*.

The antibody or antigen binding fragment thereof which specially binds to *Pseudomonas* Psl provided by the present application include, for example, full-length anti-Psl antibodies, anti-Psl scFvs, anti-Psl Fc fusion proteins, multi-specific (such as bispecific) anti-Psl antibodies, anti-Psl immunoconjugates, and the like.

Some embodiments include the antibodies or antigen binding fragments thereof which specially binds to *Pseudomonas* Psl having specific sequences and antibodies that compete with or binds to the same epitope as such antibodies or antigen binding fragments.

Also provided are nucleic acids encoding the antibodies or antigen binding fragments thereof which specially binds to *Pseudomonas* Psl, compositions comprising the anti-Psl antibodies, and methods of making and using the anti-Psl antibodies.

Definitions

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., systemic spread of a pathogen) of the disease, preventing or delaying the recurrence of the disease, delaying or slowing the progression of the disease, ameliorating the disease state, providing a remission (partial or total) of the disease, decreasing the dose of one or more of other medications required to treat the disease, delaying the progression of the disease, increasing or improving the quality of life, increasing weight gain, and/or prolonging survival. Also encompassed by "treatment" is a reduction of pathological consequence of infection (such as, for example, host cell lysis or necrosis). The methods of the application contemplate any one or more of these aspects of treatment.

The term "prevent," and similar words such as "prevented," "preventing," "prevention" etc., indicate an approach for preventing, inhibiting, or reducing the likelihood of the occurrence or recurrence of, a disease or condition, e.g., a pathogenic infection. It also refers to delaying the occurrence or recurrence of a disease or condition, or delaying the occurrence or recurrence of the symptoms of a disease or condition. As used herein, "prevention" and similar words also includes reducing the intensity, effect, symptoms and/or burden of a disease or condition prior to occurrence or recurrence of the disease or condition. As used herein, "prevention" and similar words also includes reducing the risk and susceptibility to occurrence or recurrence of the disease or condition, e.g., a pathogenic infection.

The term "antibody" includes full-length antibodies and antigen-binding fragments thereof. A full-length antibody comprises two heavy chains and two light chains. The variable regions of the light and heavy chains are responsible for antigen binding. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein includes an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragments that bind to an antigen but do not comprise a complete antibody structure. An antigen-binding fragment also includes a fusion protein comprises the antibody fragment described above. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody "competes" for binding to a target Psl with a second antibody when the first antibody inhibits target Psl binding of the second antibody by at least about 50% (such as at least about any of 55%, 60%, 65%, 70%, 75%, 80%, 85%, 90%, 95%, 98% or 99%) in the presence of an equimolar concentration of the first antibody, or vice versa. A high throughput process for "binning" antibodies based upon their cross-competition is described in PCT Publication No. WO 03/48731.

As used herein, the term "specifically binds," "specifically recognizing," or "is specific for" refers to measurable and reproducible interactions, such as binding between a target and an antibody, that is determinative of the presence of the target in the presence of a heterogeneous population of molecules, including biological molecules. For example, an antibody that specifically recognizes a target (which can be an epitope) is an antibody that binds to this target with greater affinity, avidity, more readily, and/or with greater duration than its bindings to other targets. In some embodiments, an antibody that specifically recognizes an antigen reacts with one or more antigenic determinants of the antigen with a binding affinity that is at least about 10 times its binding affinity for other targets.

An "isolated" anti-Psl antibody as used herein refers to an anti-Psl antibody that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.,* 273: 927-948 (1997); MacCallum et al., J. Mol. Biol. 262:732-745 (1996); Abhinandan and Martin, *Mol. Immunol.,* 45: 3832-3839 (2008); Lefranc M. P. et al., *Dev. Comp. Immunol.,* 27: 55-77 (2003); and Honegger and Plückthun, *J. Mol. Biol.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, *Mol. Immunol.,* 45: 3832-3839 (2008); Ehrenmann F. et al., *Nucleic Acids Res.*, 38: D301-D307 (2010); and Adolf-Bryfogle J. et al., *Nucleic Acids Res.*, 43: D432-D438 (2015). The contents of the references cited in this paragraph are incorporated herein by reference in their entireties for use in the present application and for possible inclusion in one or more claims herein.

TABLE 1

| | Kabat[1] | Chothia[2] | MacCallum[3] | IMGT[4] | AHo[5] |
|---|---|---|---|---|---|
| CDR DEFINITIONS | | | | | |
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this application (see U.S. Pat. No. 4,816,567; and Morrison et al., Proc. Natl. Acad. Sci. USA, 81:6851-6855 (1984)).

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skilled in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5):1792-1797, 2004; Edgar, R. C., *BMC Bioinformatics* 5(1):113, 2004).

The terms "Fc receptor" or "FcR" are used to describe a receptor that binds to the Fc region of an antibody. In some embodiments, an FcR of this application is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, *Annu. Rev. Immu-*

*nol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent Kd or $IC_{50}$ value) than the parent polypeptide or a native sequence IgG Fc. According to some embodiments, the improvement in binding compared to a parent polypeptide is about 3-fold, such as about any of 5, 10, 25, 50, 60, 100, 150, 200, or up to 500-fold, or about 25% to 1000% improvement in binding. The polypeptide variant which "exhibits decreased binding" to an FcR, binds at least one FcR with lower affinity (e.g., higher apparent Kd or higher $IC_{50}$ value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

The polypeptide comprising a variant Fc region which "exhibits increased ADCC" or mediates ADCC in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g., in an animal model etc. In some embodiments, the variant is from about 5-fold to about 100-fold, e.g. from about 25- to about 50-fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See also, Idusogie et al. *J. Immunol.* 164: 4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an anti-Psl antibody or composition as disclosed herein, is an amount sufficient to carry out a specifically stated purpose. An "effective amount" can be determined empirically and by known methods relating to the stated purpose.

The term "therapeutically effective amount" refers to an amount of an anti-Psl antibody or composition as disclosed herein, effective to "treat" a disease or disorder in an individual. In the case of *P. aeruginosa* infection, the therapeutically effective amount of the anti-Psl antibody or composition as disclosed herein can reduce the number of infected cells; inhibit (i.e., slow to some extent and preferably stop) the spread of infection; and/or relieve to some extent one or more of the symptoms associated with the infection. To the extent the anti-Psl antibody or composition as disclosed herein can prevent *P. aeruginosa* growth and/or kill *P. aeruginosa* in an infection, the anti-Psl can be cytostatic and/or cytotoxic. In some embodiments, the therapeutically effective amount is an amount that inhibits infection in a patient. In some embodiments, the therapeutically effective amount is an amount that completely eradicates infection in a patient.

As used herein, by "pharmaceutically acceptable" or "pharmacologically compatible" is meant a material that is not biological or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

It is understood that embodiments of the application described herein include "consisting of" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat infection of type X means the method is used to treat infection of types other than X.

As used herein and in the appended claims, the singular forms "a," "or," and "the" include plural referents unless the context clearly dictates otherwise.
Anti-Psl Antibodies In one aspect, the present application provides anti-Psl antibodies that specifically bind to Psl. Anti-Psl antibodies include, but are not limited to, humanized antibodies, chimeric antibodies, mouse antibodies, human antibodies, and antibodies comprising the heavy chain and/or light chain complementarity determining regions (CDRs) discussed herein. In one aspect, the application provides isolated antibodies that bind to Psl. Contemplated anti-Psl antibodies include, for example, full-length anti-Psl antibodies (e.g., full-length IgG1, IgG2 or IgG4), anti-Psl scFvs, multi-specific (such as bispecific) anti-Psl antibodies, anti-Psl immunoconjugates, and the like. In some embodiments, the anti-Psl antibody is a Fab, a Fab', a F(ab)'2, a Fab'-SH, a single-chain Fv (scFv), an Fv fragment, a dAb, a Fd, or a diabody. In some embodiments, reference to an antibody that specifically binds to Psl means that the antibody binds to Psl with an affinity that is at least about 10 times (including for example at least about any of 10, $10^2$, $10^3$, $10^4$, $10^5$, $10^6$, or $10^7$ times) its binding affinity for non-target. In some embodiments, the non-target is an antigen that is not Psl. Binding affinity can be determined by methods known in the art, such as ELISA, fluorescence activated cell sorting (FACS) analysis, or radioimmunoprecipitation assay (RIA). Kd can be determined by methods known in the art, such as surface plasmon resonance (SPR) assay or biolayer interferometry (BLI).

In certain aspects, the anti-Psl antibody or antigen-binding fragment thereof that specifically binds to *Pseudomonas* Psl (a) promotes, mediates, or enhances opsonophagocytic killing (OPK) of *P. aeruginosa*, and/or (b) inhibits attachment of *P. aeruginosa* to epithelial cells.

Although anti-Psl antibodies containing human sequences (e.g., human heavy and light chain variable domain sequences comprising human CDR sequences) are extensively discussed herein, non-human anti-Psl antibodies are also contemplated. In some embodiments, non-human anti-Psl antibodies comprise human CDR sequences from an anti-Psl antibody as described herein and non-human framework sequences. Non-human framework sequences include, in some embodiments, any sequence that can be used for generating synthetic heavy and/or light chain variable domains using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human anti-Psl antibody includes an anti-Psl antibody generated by grafting one or more human CDR sequences as described herein onto a non-human framework sequence (e.g., a mouse or chicken framework sequence).

In some embodiments, the anti-Psl antibody described herein specifically recognizes an epitope within *Pseudomonas* Psl. In some embodiments, the anti-Psl antibody is specific for *Pseudomonas* Psl and does not exhibit cross-reactivity with other types of protein.

In some embodiments, the anti-Psl antibody comprises an antibody heavy chain constant region and an antibody light chain constant region. In some embodiments, the anti-Psl antibody comprises an IgG1 heavy chain constant region. In some embodiments, the anti-Psl antibody comprises an IgG2 heavy chain constant region. In some embodiments, the anti-Psl antibody comprises an IgG3 heavy chain constant region. In some embodiments, the anti-Psl antibody comprises an IgG4 heavy chain constant region. In some embodiments, the IgG is a human IgG. In some embodiments, the heavy chain constant region comprises or consists of the amino acid sequence of SEQ ID NO: 160. In some embodiments, the heavy chain constant region comprises or consists of the amino acid sequence of SEQ ID NO: 161. In some embodiments, the anti-Psl comprises a lambda light chain constant region. In some embodiments, the anti-Psl antibody comprises a kappa light chain constant region. In some embodiments, the light chain constant region comprises or consists of the amino acid sequence of SEQ ID NO: 162. In some embodiments, the anti-Psl antibody comprises an antibody heavy chain variable domain and an antibody light chain variable domain.

In one aspect, the present application provides an isolated anti-Psl antibody, wherein the anti-Psl antibody comprises a heavy chain variable domain ($V_H$) comprising a heavy chain complementarity determining region (HC-CDR) 1 comprising the amino acid sequence of any one of SEQ ID NOs: 2-3, and 5-12, or a variant thereof comprising up to about 3 (such as about any of 1, 2, or 3) amino acid substitutions; an HC-CDR2 comprising the amino acid sequence of any one of SEQ ID NOs: 14-15, and 17-23, or a variant thereof comprising up to about 3 (such as about any of 1, 2, or 3) amino acid substitutions; and an HC-CDR3 comprising the amino acid sequence of any one of SEQ ID NOs: 25-26, and 28-34, or a variant thereof comprising up to about 3 (such as about any of 1, 2, or 3) amino acid substitutions.

In some embodiments, the anti-Psl antibody comprises a light chain variable domain ($V_L$) comprising a light chain complementarity determining region (LC-CDR1) comprising the amino acid sequence of any one of SEQ ID NOs: 38-39, and 4149, or a variant thereof comprising up to about 3 (such as about any of 1, 2, or 3) amino acid substitutions; an LC-CDR2 comprising the amino acid sequence of any one of SEQ ID NOs: 52-53, and 55-61, or a variant thereof comprising up to about 3 (such as about any of 1, 2, or 3) amino acid substitutions; and an LC-CDR3 comprising the amino acid sequence of any one of SEQ ID NOs: 63-64, 66-68, and 70-75, or a variant thereof comprising up to about 3 (such as about any of 1, 2, or 3) amino acid substitutions.

In some embodiments, the anti-Psl antibody comprises a $V_H$ comprising: an HC-CDR1 comprising the amino acid sequence of any one of SEQ ID NOs: 2-3, and 5-12, or a variant thereof comprising up to about 3 amino acid substitutions; an HC-CDR2 comprising the amino acid sequence of any one of SEQ ID NOs: 14-15, and 17-23, or a variant thereof comprising up to about 3 amino acid substitutions; and an HC-CDR3 comprising the amino acid sequence of any one of SEQ ID NOs: 25-26, and 28-34, or a variant thereof comprising up to about 3 amino acid substitutions; and a $V_L$ comprising an LC-CDR1 comprising the amino acid sequence of any one of SEQ ID NOs: 38-39, and 41-49, or a variant thereof comprising up to about 3 amino acid substitutions; an LC-CDR2 comprising the amino acid sequence of any one of SEQ ID NOs: 52-53, and 55-61, or a variant thereof comprising up to about 3 amino acid substitutions; and an LC-CDR3 comprising the amino acid sequence of any one of SEQ ID NOs: 63-64, 66-68, and 70-75, or a variant thereof comprising up to about 3 amino acid substitutions.

In some embodiments, the amino acid substitutions described above are limited to "exemplary substitutions" shown in Table 8 of this application. In some embodiments, the amino acid substitutions are limited to "preferred substitutions" shown in Table 8 of this application.

In some embodiments, the anti-Psl antibody comprises a $V_H$ comprising: an HC-CDR1 comprising the amino acid sequence of any one of SEQ ID NOs: 2-3, and 5-12, an HC-CDR2 comprising the amino acid sequence of any one of SEQ ID NOs: 14-15, and 17-23, and an HC-CDR3 comprising the amino acid sequence of any one of SEQ ID NOs: 25-26, and 28-34; and a $V_L$ comprising: an LC-CDR1 comprising the amino acid sequence of any one of SEQ ID NOs: 38-39, and 41-49, an LC-CDR2 comprising the amino acid sequence of any one of SEQ ID NOs: 52-53, and 55-61, and an LC-CDR3 comprising the amino acid sequence of any one of SEQ ID NOs: 63-64, 66-68, and 70-75.

In some embodiments, the anti-Psl antibody comprises a $V_H$ comprising an HC-CDR1, an HC-CDR2 and an HC-CDR3 of the $V_H$ comprising the amino acid sequence of any one of SEQ ID NOs: 80-81, 83-90, and 159; and a $V_L$ comprising an LC-CDR1, an LC-CDR2, and an LC-CDR3 of the $V_L$ comprising the amino acid sequence of any one of SEQ ID NOs: 92-93, 95-97, and 99-104.

In some embodiments, the anti-Psl antibody comprises: (i) a $V_H$ comprising an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; (ii) a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; (iii) a $V_H$ comprising an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28, or a variant thereof comprising up to about 5 amino acid substitutions in the HC-CDRs; (iv) a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29, or a variant thereof comprising up to about 5 amino acid substitutions in the HC-CDRs; (v) a $V_H$ comprising an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; (vi) a $V_H$ comprising an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30, or a variant thereof comprising up to about 5 amino acid substitutions in the HC-CDRs; (vii) a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; (viii) a $V_H$ comprising an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31, or a variant thereof comprising up to about 5 amino acid substitutions in the HC-CDRs; (ix) a $V_H$ comprising an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32, or a variant thereof comprising up to about 5 amino acid substitutions in the HC-CDRs; (x) a $V_H$ comprising an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33, or a variant thereof comprising up to about 5 amino acid substitutions in the HC-CDRs; or (xi) a $V_H$ comprising an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34, or a variant thereof comprising up to about 5 amino acid substitutions in the HC-CDRs.

In some embodiments, the anti-Psl antibody comprises: (i) a $V_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63, or a variant thereof comprising up to about 5 amino acid substitutions in the LC-CDRs; (ii) a $V_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64, or a variant thereof comprising up to about 5 amino acid substitutions in the LC-CDRs; (iii) a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66, or a variant thereof comprising up to about 5 amino acid substitutions in the LC-CDRs; (iv) a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67, or a variant thereof comprising up to about 5 amino acid substitutions in the LC-CDRs; (v) a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68, or a variant thereof comprising up to about 5 amino acid substitutions in the LC-CDRs; (vi) a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70, or a variant thereof comprising up to about 5 amino acid substitutions in the LC-CDRs; (vii) a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71, or a variant thereof comprising up to about 5 amino acid substitutions in the LC-CDRs; (viii) a $V_L$ comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72, or a variant thereof comprising up to about 5 amino acid substitutions in the LC-CDRs; (ix) a $V_L$ comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73, or a variant thereof comprising up to about 5 amino acid substitutions in the LC-CDRs; (x) a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74, or a variant thereof comprising up to about 5 amino acid substitutions in the LC-CDRs; or (xi) a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75, or a variant thereof comprising up to about 5 amino acid substitutions in the LC-CDRs.

In some embodiments, the anti-Psl antibody comprises: (i) a $V_H$ comprising an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; and a $V_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63, or a variant thereof comprising up to about 5 amino acid substitutions in the LC-CDRs; (ii) a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; and a $V_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64, or a variant thereof comprising up to about 5 amino acid substitutions in the LC-CDRs; (iii) a $V_H$ comprising an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28, or a variant thereof comprising up to about 5 amino acid substitutions in the HC-CDRs; and a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66, or a variant thereof comprising up to about 5 amino acid substitutions in the LC-CDRs; (iv) a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29, or a variant thereof comprising up to about 5 amino acid substitutions in the HC-CDRs; and a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67, or a variant thereof comprising up to about 5 amino acid substitutions in the LC-CDRs; (v) a $V_H$ comprising an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; and a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68, or a variant thereof comprising up to about 5 amino acid substitutions in the LC-CDRs; (vi) a $V_H$ comprising an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30, or a variant thereof comprising up to about 5 amino acid substitutions in the HC-CDRs; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70, or a variant thereof comprising up to about 5 amino acid substitutions in the LC-CDRs; (vii) a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; and a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71, or a variant thereof comprising up to about 5 amino acid substitutions in the LC-CDRs; (viii) a $V_H$ comprising an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31, or a variant thereof comprising up to about 5 amino acid substitutions in the HC-CDRs; and a $V_L$ comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72, or a variant thereof comprising up to about 5 amino acid substitutions in the LC-CDRs; (ix) a $V_H$ comprising an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32, or a variant thereof comprising up to about 5 amino acid substitutions in the HC-CDRs; and a $V_L$ comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73, or a variant thereof comprising up to about 5 amino acid substitutions in the LC-CDRs; (x) a $V_H$ comprising an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33, or a variant thereof comprising up to about 5 amino acid substitutions in the HC-CDRs; and a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74, or a variant thereof comprising up to about 5 amino acid substitutions in the LC-CDRs; or (xi) a $V_H$ comprising an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34, or a variant thereof comprising up to about 5 amino acid substitutions in the HC-CDRs; and a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75, or a variant thereof comprising up to about 5 amino acid substitutions in the LC-CDRs.

In some embodiments, the anti-Psl antibody comprises a $V_H$ comprising the amino acid sequence of any one of SEQ ID NOs: 80-81, 83-90, and 159 or a variant thereof having at least about 90% (for example at least about any of 91%, 92%, 93%, 94%, 95%, 96%, 97%, 98%, or 99%) sequence identity, and a $V_L$ comprising the amino acid sequence of any one of SEQ ID NOs: 92-93, 95-97, and 99-104 or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of any one of SEQ ID NOs: 80-81, 83-90, and 159, and a $V_L$ comprising the amino acid sequence of any one of SEQ ID NOs: 92-93, 95-97, and 99-104.

In some embodiments, the anti-Psl is a full-length antibody. In some embodiments, the anti-Psl antibody comprises IgG1 constant domains. In some embodiments, the IgG1 is human IgG1. In some embodiments, the anti-Psl antibody comprises IgG4 constant domains. In some embodiments, the IgG4 is human IgG4. In some embodiments, the anti-Psl heavy chain constant region comprises or consists of the amino acid sequence of SEQ ID NO: 160. In some embodiments, the anti-Psl heavy chain constant region comprises or consists of the amino acid sequence of SEQ ID NO: 161. In some embodiments, the anti-Psl light chain constant region comprises or consists of the amino acid sequence of SEQ ID NO: 162.

In some embodiments, the anti-Psl antibody comprises a $V_H$ comprising HC-CDR1, HC-CDR2 and HC-CDR3 of the $V_H$ of SEQ ID NO: 80, and a $V_L$ comprising LC-CDR1, LC-CDR2 and LC-CDR3 of the $V_L$ of SEQ ID NO: 92. In some embodiments, the anti-Psl antibody comprises a $V_H$ comprising HC-CDR1, HC-CDR2 and HC-CDR3 of the $V_H$ of SEQ ID NO: 81, and a $V_L$ comprising LC-CDR1, LC-CDR2 and LC-CDR3 of the $V_L$ of SEQ ID NO: 93. In some embodiments, the anti-Psl antibody comprises a $V_H$ comprising HC-CDR1, HC-CDR2 and HC-CDR3 of the $V_H$ of SEQ ID NO: 83, and a $V_L$ comprising LC-CDR1, LC-CDR2 and LC-CDR3 of the $V_L$ of SEQ ID NO: 95. In some embodiments, the anti-Psl antibody comprises a $V_H$ comprising HC-CDR1, HC-CDR2 and HC-CDR3 of the $V_H$ of SEQ ID NO: 84, and a $V_L$ comprising LC-CDR1, LC-CDR2 and LC-CDR3 of the $V_L$ of SEQ ID NO: 96. In some embodiments, the anti-Psl antibody comprises a $V_H$ comprising HC-CDR1, HC-CDR2 and HC-CDR3 of the $V_H$ of SEQ ID NO: 85, and a $V_L$ comprising LC-CDR1, LC-CDR2 and LC-CDR3 of the $V_L$ of SEQ ID NO: 97. In some embodiments, the anti-Psl antibody comprises a $V_H$ comprising HC-CDR1, HC-CDR2 and HC-CDR3 of the $V_H$ of SEQ ID NO: 86, and a $V_L$ comprising LC-CDR1, LC-CDR2 and LC-CDR3 of the $V_L$ of SEQ ID NO: 99. In some embodiments, the anti-Psl antibody comprises a $V_H$ comprising HC-CDR1, HC-CDR2 and HC-CDR3 of the $V_H$ of SEQ ID NO: 81, and a $V_L$ comprising LC-CDR1, LC-CDR2 and LC-CDR3 of the $V_L$ of SEQ ID NO: 100. In some embodiments, the anti-Psl antibody comprises a $V_H$ comprising HC-CDR1, HC-CDR2 and HC-CDR3 of the $V_H$ of SEQ ID NO: 87, and a $V_L$ comprising LC-CDR1, LC-CDR2 and LC-CDR3 of the $V_L$ of SEQ ID NO: 101. In some embodiments, the anti-Psl antibody comprises a $V_H$ comprising HC-CDR1, HC-CDR2 and HC-CDR3 of the $V_H$ of SEQ ID NO: 88, and a $V_L$ comprising LC-CDR1, LC-CDR2 and LC-CDR3 of the $V_L$ of SEQ ID NO: 102. In some embodiments, the anti-Psl antibody comprises a $V_H$ comprising HC-CDR1, HC-CDR2 and HC-CDR3 of the V$_H$ of SEQ ID NO: 89, and a V$_L$ comprising LC-CDR1, LC-CDR2 and LC-CDR3 of the V$_L$ of SEQ ID NO: 103. In some embodiments, the anti-Psl antibody comprises a V$_H$ comprising HC-CDR1, HC-CDR2 and HC-CDR3 of the V$_H$ of SEQ ID NO: 90, and a V$_L$ comprising LC-CDR1, LC-CDR2 and LC-CDR3 of the V$_L$ of SEQ ID NO: 104. In some embodiments, the anti-Psl antibody comprises a V$_H$ comprising HC-CDR1, HC-CDR2 and HC-CDR3 of the V$_H$ of SEQ ID NO: 159, and a V$_L$ comprising LC-CDR1, LC-CDR2 and LC-CDR3 of the V$_L$ of SEQ ID NO: 95.

In some embodiments, the anti-Psl antibody comprises a V$_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 24, or a variant thereof comprising up to about 5 amino acid substitutions in the HC-CDRs; and a V$_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a V$_H$ comprising: an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; and a V$_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63, or a variant thereof comprising up to about 5 amino acid substitutions in the LC-CDRs.

In some embodiments, the anti-Psl antibody comprises a V$_H$ comprising: an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25; and a V$_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63. In some embodiments, there is provided an anti-Psl antibody that specifically competes with an antibody comprising a V$_H$ comprising: an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25; and a V$_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63. In some embodiments, there is provided an anti-Psl antibody that binds to the same epitope as an antibody comprising a V$_H$ comprising: an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25; and a V$_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63.

In some embodiments, the anti-Psl antibody comprises a V$_H$ comprising the amino acid sequence of SEQ ID NO: 80, or a variant thereof having at least about 90% (for example at least about any of 91%, 92%, 93%, 94%, 95%, 96%, 97%, 98%, or 99%) sequence identity, and a V$_L$ comprising the amino acid sequence of SEQ ID NO: 92, or a variant thereof having at least about 90% (for example at least about any of 91%, 92%, 93%, 94%, 95%, 96%, 97%, 98%, or 99%) sequence identity. In some embodiments, the anti-Psl antibody comprises a V$_H$ comprising the amino acid sequence of SEQ ID NO: 80 and a V$_L$ comprising the amino acid sequence of SEQ ID NO: 92. In some embodiments, the anti-Psl antibody comprises a V$_H$ comprising an HC-CDR1, an HC-CDR2 and an HC-CDR3 of the V$_H$ comprising the amino acid sequence of SEQ ID NO: 80; and a V$_L$ comprising an LC-CDR1, an LC-CDR2, and an LC-CDR3 of the V$_L$ comprising the amino acid sequence of SEQ ID NOs: 92.

In some embodiments, the anti-Psl antibody comprises a V$_H$ comprising: an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; and a V$_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64, or a variant thereof comprising up to about 5 amino acid substitutions in the LC-CDRs.

In some embodiments, the anti-Psl antibody comprises a V$_H$ comprising: an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a V$_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64. In some embodiments, there is provided an anti-Psl antibody that specifically competes with an antibody comprising a V$_H$ comprising: an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a V$_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64. In some embodiments, there is provided an anti-Psl antibody that binds to the same epitope as an antibody comprising a V$_H$ comprising: an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a V$_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64.

In some embodiments, the anti-Psl antibody comprises a V$_H$ comprising the amino acid sequence of SEQ ID NO: 81, or a variant thereof having at least about 90% (for example at least about any of 91%, 92%, 93%, 94%, 95%, 96%, 97%, 98%, or 99%) sequence identity, and a V$_L$ comprising the amino acid sequence of SEQ ID NO: 93, or a variant thereof having at least about 90% (for example at least about any of 91%, 92%, 93%, 94%, 95%, 96%, 97%, 98%, or 99%)

sequence identity. In some embodiments, the anti-Psl antibody comprises a $V_H$ comprising the amino acid sequence of SEQ ID NO: 81 and a $V_L$ comprising the amino acid sequence of SEQ ID NO: 93. In some embodiments, the anti-Psl antibody comprises a $V_H$ comprising an HC-CDR1, an HC-CDR2 and an HC-CDR3 of the $V_H$ comprising the amino acid sequence of SEQ ID NO: 81; and a $V_L$ comprising an LC-CDR1, an LC-CDR2, and an LC-CDR3 of the $V_L$ comprising the amino acid sequence of SEQ ID NOs: 93.

In some embodiments, the anti-Psl antibody comprises a $V_H$ comprising: an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28, or a variant thereof comprising up to about 5 amino acid substitutions in the HC-CDRs; and a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28; and a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66. In some embodiments, there is provided an anti-Psl antibody that specifically competes with an antibody comprising a $V_H$ comprising: an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28; and a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66. In some embodiments, there is provided an anti-Psl antibody that binds to the same epitope as an antibody comprising a $V_H$ comprising: an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28; and a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66.

In some embodiments, the anti-Psl antibody comprises a $V_H$ comprising the amino acid sequence of SEQ ID NO: 83, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 95, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 83 and a $V_L$ comprising the amino acid sequence of SEQ ID NO: 95. In some embodiments, the anti-Psl antibody comprises a $V_H$ comprising an HC-CDR1, an HC-CDR2 and an HC-CDR3 of the $V_H$ comprising the amino acid sequence of SEQ ID NO: 83; and a $V_L$ comprising an LC-CDR1, an LC-CDR2, and an LC-CDR3 of the $V_L$ comprising the amino acid sequence of SEQ ID NOs: 95.

In some embodiments, the anti-Psl antibody comprises a $V_H$ comprising the amino acid sequence of SEQ ID NO: 159, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 95, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 159 and a $V_L$ comprising the amino acid sequence of SEQ ID NO: 95. In some embodiments, the anti-Psl antibody comprises a $V_H$ comprising an HC-CDR1, an HC-CDR2 and an HC-CDR3 of the $V_H$ comprising the amino acid sequence of SEQ ID NO: 159; and a $V_L$ comprising an LC-CDR1, an LC-CDR2, and an LC-CDR3 of the $V_L$ comprising the amino acid sequence of SEQ ID NOs: 95.

In some embodiments, the anti-Psl antibody comprises a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29, or a variant thereof comprising up to about 5 amino acid substitutions in the HC-CDRs; and a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67, or a variant thereof comprising up to about 5 amino acid substitutions in the LC-CDRs.

In some embodiments, the anti-Psl antibody comprises a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29; and a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67. In some embodiments, there is provided an anti-Psl antibody that specifically competes with an antibody comprising a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29; and a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67. In some embodiments, there is provided an anti-Psl antibody that binds to the same epitope as an antibody comprising a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29; and a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67.

In some embodiments, the anti-Psl antibody comprises a $V_H$ comprising the amino acid sequence of SEQ ID NO: 84, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 96, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 84 and a $V_L$ comprising the amino acid sequence of SEQ ID NO: 96. In some embodiments, the anti-Psl antibody comprises a $V_H$ comprising an HC-CDR1, an HC-CDR2 and an HC-CDR3 of the $V_H$ comprising the amino acid sequence of SEQ ID NO: 84; and a $V_L$ comprising an LC-CDR1, an LC-CDR2, and an LC-CDR3 of the $V_L$ comprising the amino acid sequence of SEQ ID NOs: 96.

In some embodiments, the anti-Psl antibody comprises a $V_H$ comprising: an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25, or a variant thereof comprising up to about 5 amino acid substitutions in the HC-CDRs; and a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25; and a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68. In some embodiments, there is provided an anti-Psl antibody that specifically competes with an antibody comprising a $V_H$ comprising: an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25; and a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68. In some embodiments, there is provided an anti-Psl antibody that binds to the same epitope as an antibody comprising a $V_H$ comprising: an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25; and a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68.

In some embodiments, the anti-Psl antibody comprises a $V_H$ comprising the amino acid sequence of SEQ ID NO: 85, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 97, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 85 and a $V_L$ comprising the amino acid sequence of SEQ ID NO: 97. In some embodiments, the anti-Psl antibody comprises a $V_H$ comprising an HC-CDR1, an HC-CDR2 and an HC-CDR3 of the $V_H$ comprising the amino acid sequence of SEQ ID NO: 85; and a $V_L$ comprising an LC-CDR1, an LC-CDR2, and an LC-CDR3 of the $V_L$ comprising the amino acid sequence of SEQ ID NOs: 97.

In some embodiments, the anti-Psl antibody comprises a $V_H$ comprising: an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30, or a variant thereof comprising up to about 5 amino acid substitutions in the HC-CDRs; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70. In some embodiments, there is provided an anti-Psl antibody that specifically competes with an antibody comprising a $V_H$ comprising: an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70. In some embodiments, there is provided an anti-Psl antibody that binds to the same epitope as an antibody comprising a $V_H$ comprising: an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70.

In some embodiments, the anti-Psl antibody comprises a $V_H$ comprising the amino acid sequence of SEQ ID NO: 86, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 99, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 86 and a $V_L$ comprising the amino acid sequence of SEQ ID NO: 99. In some embodiments, the anti-Psl antibody comprises a $V_H$ comprising an HC-CDR1, an HC-CDR2 and an HC-CDR3 of the $V_H$ comprising the amino acid sequence of SEQ ID NO: 86; and a $V_L$ comprising an LC-CDR1, an LC-CDR2, and an LC-CDR3 of the $V_L$ comprising the amino acid sequence of SEQ ID NOs: 99.

In some embodiments, the anti-Psl antibody comprises a $V_H$ comprising: an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to about 5 amino acid substitutions in the HC-CDRs; and a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71. In some embodiments, there is provided an anti-Psl antibody that specifically competes with an antibody comprising a $V_H$ comprising: an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71. In some embodiments, there is provided an anti-Psl antibody that binds to the same epitope as an antibody comprising a $V_H$ comprising: an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71.

In some embodiments, the anti-Psl antibody comprises a $V_H$ comprising the amino acid sequence of SEQ ID NO: 81, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 100, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 81 and a $V_L$ comprising the amino acid sequence of SEQ ID NO: 100. In some embodiments, the anti-Psl antibody comprises a $V_H$ comprising an HC-CDR1, an HC-CDR2 and an HC-CDR3 of the $V_H$ comprising the amino acid sequence of SEQ ID NO: 81; and a $V_L$ comprising an LC-CDR1, an LC-CDR2, and an LC-CDR3 of the $V_L$ comprising the amino acid sequence of SEQ ID NOs: 100.

In some embodiments, the anti-Psl antibody comprises a $V_H$ comprising: an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31, or a variant thereof comprising up to about 5 amino acid substitutions in the HC-CDRs; and a $V_L$ comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31; and a $V_L$ comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72. In some embodiments, there is provided an anti-Psl antibody that specifically competes with an antibody comprising a $V_H$ comprising: an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31; and a $V_L$ comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72. In some embodiments, there is provided an anti-Psl antibody that binds to the same epitope as an antibody comprising a $V_H$ comprising: an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31; and a $V_L$ comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72.

In some embodiments, the anti-Psl antibody comprises a $V_H$ comprising the amino acid sequence of SEQ ID NO: 87, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 101, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 87 and a $V_L$ comprising the amino acid sequence of SEQ ID NO: 101. In some embodiments, the anti-Psl antibody comprises a $V_H$ comprising an HC-CDR1, an HC-CDR2 and an HC-CDR3 of the $V_H$ comprising the amino acid sequence of SEQ ID NO: 87; and a $V_L$ comprising an LC-CDR1, an LC-CDR2, and an LC-CDR3 of the $V_L$ comprising the amino acid sequence of SEQ ID NOs: 101.

In some embodiments, the anti-Psl antibody comprises a $V_H$ comprising: an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32, or a variant thereof comprising up to about 5 amino acid substitutions in the HC-CDRs; and a $V_L$ comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32; and a $V_L$ comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73. In some embodiments, there is provided an anti-Psl antibody that specifically competes with an antibody comprising a $V_H$ comprising: an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32; and a $V_L$ comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73. In some embodiments, there is provided an anti-Psl antibody that binds to the same epitope as an antibody comprising a $V_H$ comprising: an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32; and a $V_L$ comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73.

In some embodiments, the anti-Psl antibody comprises a $V_H$ comprising the amino acid sequence of SEQ ID NO: 88, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 102, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 88 and a $V_L$ comprising the amino acid sequence of SEQ ID NO: 102. In some embodiments, the anti-Psl antibody comprises a $V_H$ comprising an HC-CDR1, an HC-CDR2 and an HC-CDR3 of the $V_H$ comprising the amino acid sequence of SEQ ID NO: 88; and a $V_L$ comprising an LC-CDR1, an LC-CDR2, and an LC-CDR3 of the $V_L$ comprising the amino acid sequence of SEQ ID NOs: 102.

In some embodiments, the anti-Psl antibody comprises a $V_H$ comprising: an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33, or a variant thereof comprising up to about 5 amino acid substitutions in the HC-CDRs; and a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33; and a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74. In some embodiments, there is provided an anti-Psl antibody that specifically competes with an antibody comprising a $V_H$ comprising: an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33; and a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74. In some embodiments, there is provided an anti-Psl antibody that binds to the same epitope as an antibody comprising a $V_H$ comprising: an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33; and a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74.

In some embodiments, the anti-Psl antibody comprises a $V_H$ comprising the amino acid sequence of SEQ ID NO: 89, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 103, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 89 and a $V_L$ comprising the amino acid sequence of SEQ ID NO: 103. In some embodiments, the anti-Psl antibody comprises a $V_H$ comprising an HC-CDR1, an HC-CDR2 and an HC-CDR3 of the $V_H$ comprising the amino acid sequence of SEQ ID NO: 89; and a $V_L$ comprising an LC-CDR1, an LC-CDR2, and an LC-CDR3 of the $V_L$ comprising the amino acid sequence of SEQ ID NOs: 103.

In some embodiments, the anti-Psl antibody comprises a $V_H$ comprising: an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34, or a variant thereof comprising up to about 5 amino acid substitutions in the HC-CDRs; and a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34; and a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75. In some embodiments, there is provided an anti-Psl antibody that specifically competes with an antibody comprising a $V_H$ comprising: an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34; and a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75. In some embodiments, there is provided an anti-Psl antibody that binds to the same epitope as an antibody comprising a V_H comprising: an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34; and a V_L comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75.

In some embodiments, the anti-Psl antibody comprises a V_H comprising the amino acid sequence of SEQ ID NO: 90, or a variant thereof having at least about 90% (for example at least about any of 91%, 92%, 93%, 94%, 95%, 96%, 97%, 98%, or 99%) sequence identity, and a V_L comprising the amino acid sequence of SEQ ID NO: 104, or a variant thereof having at least about 90% (for example at least about any of 91%, 92%, 93%, 94%, 95%, 96%, 97%, 98%, or 99%) sequence identity. In some embodiments, the anti-Psl antibody comprises a V_H comprising the amino acid sequence of SEQ ID NO: 90 and a V_L comprising the amino acid sequence of SEQ ID NO: 104. In some embodiments, the anti-Psl antibody comprises a V_H comprising an HC-CDR1, an HC-CDR2 and an HC-CDR3 of the V_H comprising the amino acid sequence of SEQ ID NO: 90; and a V_L comprising an LC-CDR1, an LC-CDR2, and an LC-CDR3 of the V_L comprising the amino acid sequence of SEQ ID NOs: 104.

In one aspect, the present application provides an isolated anti-Psl antibody, wherein the anti-Psl antibody comprises a V_H comprising an HC-CDR1 comprising IHSVH (SEQ ID NO: 4), or a variant thereof comprising up to about 3 amino acid substitutions; an HC-CDR2 comprising TIISSGTTT-TYAQSFQD (SEQ ID NO: 16), or a variant thereof comprising up to about 3 amino acid substitutions; and an HC-CDR3 comprising $X_1X_2X_3X_4$ (SEQ ID NO: 189), or a variant thereof comprising up to about 3 amino acid substitutions, wherein $X_1$ is D, Y or N, $X_2$ is G, or A, $X_3$ is D, or T, $X_4$ is S, A, or T; and a V_L comprising an LC-CDR1 comprising RASQGISSWLA (SEQ ID NO: 40), or a variant thereof comprising up to about 3 amino acid substitutions; an LC-CDR2 comprising HASTLES (SEQ ID NO: 54), or a variant thereof comprising up to about 3 amino acid substitutions; and an LC-CDR3 comprising LQAX_1SLPHT (SEQ ID NO: 158), or a variant thereof comprising up to about 3 amino acid substitutions, wherein $X_1$ is N, D, Y, F, P, G, K, H, A, C, E, Q, R, S, T, V, W or L.

In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 94. In some embodiments, the anti-Psl antibody comprises a V_H comprising HC-CDR1, HC-CDR2 and HC-CDR3 of the V_H of SEQ ID NO: 105, and a V_L comprising LC-CDR1, LC-CDR2 and LC-CDR3 of the V_L of SEQ ID NO: 94. In some embodiments, the anti-Psl antibody comprises a V_H comprising HC-CDR1, HC-CDR2 and HC-CDR3 of the V_H of SEQ ID NO: 106, and a V_L comprising LC-CDR1, LC-CDR2 and LC-CDR3 of the V_L of SEQ ID NO: 94. In some embodiments, the anti-Psl antibody comprises a V_H comprising HC-CDR1, HC-CDR2 and HC-CDR3 of the V_H of SEQ ID NO: 107, and a V_L comprising LC-CDR1, LC-CDR2 and LC-CDR3 of the V_L of SEQ ID NO: 94. In some embodiments, the anti-Psl antibody comprises a V_H comprising HC-CDR1, HC-CDR2 and HC-CDR3 of the V_H of SEQ ID NO: 108, and a V_L comprising LC-CDR1, LC-CDR2 and LC-CDR3 of the V_L of SEQ ID NO: 94. In some embodiments, the anti-Psl antibody comprises a V_H comprising HC-CDR1, HC-CDR2 and HC-CDR3 of the V_H of SEQ ID NO: 109, and a V_L comprising LC-CDR1, LC-CDR2 and LC-CDR3 of the V_L of SEQ ID NO: 94. In some embodiments, the anti-Psl antibody comprises a V_H comprising HC-CDR1, HC-CDR2 and HC-CDR3 of the V_H of SEQ ID NO: 110, and a V_L comprising LC-CDR1, LC-CDR2 and LC-CDR3 of the V_L of SEQ ID NO: 94. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 111. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 112. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 113. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 114. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 115. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 116. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 117. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 118. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 119. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 120. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 121. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 122. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 123. In some embodiments, the anti-Psl antibody comprises a V_H comprising HC-CDR1, HC-CDR2 and HC-CDR3 of the V_H of SEQ ID NO: 82, and a V_L comprising LC-CDR1, LC-CDR2 and LC-CDR3 of the V_L of SEQ ID NO: 124. In some embodiments, the anti-Psl antibody comprises a V_H comprising HC-CDR1, HC-CDR2 and HC-CDR3 of the V_H of SEQ ID NO: 82, and a $V_L$ comprising LC-CDR1, LC-CDR2 and LC-CDR3 of the $V_L$ of SEQ ID NO: 125. In some embodiments, the anti-Psl antibody comprises a $V_H$ comprising HC-CDR1, HC-CDR2 and HC-CDR3 of the $V_H$ of SEQ ID NO: 82, and a $V_L$ comprising LC-CDR1, LC-CDR2 and LC-CDR3 of the $V_L$ of SEQ ID NO: 126. In some embodiments, the anti-Psl antibody comprises a $V_H$ comprising HC-CDR1, HC-CDR2 and HC-CDR3 of the $V_H$ of SEQ ID NO: 82, and a $V_L$ comprising LC-CDR1, LC-CDR2 and LC-CDR3 of the $V_L$ of SEQ ID NO: 127. In some embodiments, the anti-Psl antibody comprises a $V_H$ comprising HC-CDR1, HC-CDR2 and HC-CDR3 of the $V_H$ of SEQ ID NO: 107, and a $V_L$ comprising LC-CDR1, LC-CDR2 and LC-CDR3 of the $V_L$ of SEQ ID NO: 113. In some embodiments, the anti-Psl antibody comprises a $V_H$ comprising HC-CDR1, HC-CDR2 and HC-CDR3 of the $V_H$ of SEQ ID NO: 107, and a $V_L$ comprising LC-CDR1, LC-CDR2 and LC-CDR3 of the $V_L$ of SEQ ID NO: 123. In some embodiments, the anti-Psl antibody comprises a $V_H$ comprising HC-CDR1, HC-CDR2 and HC-CDR3 of the $V_H$ of SEQ ID NO: 107, and a $V_L$ comprising LC-CDR1, LC-CDR2 and LC-CDR3 of the $V_L$ of SEQ ID NO: 116.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity to the amino acid sequence of SEQ ID NOs: 82, and a $V_L$ comprising the amino acid sequence of SEQ ID NO: 94 or a variant thereof having at least about 90% (for example at least about any of 91%, 92%, 93%, 94%, 95%, 96%, 97%, 98%, or 99%) sequence identity to the amino acid sequence of SEQ ID NOs: 94. In some embodiments, the anti-Psl antibody comprises a $V_H$ comprising the amino acid sequence of SEQ ID NO: 82 and a $V_L$ comprising the amino acid sequence of SEQ ID NO: 94. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 94.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 165, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 165; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 165; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 165; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65.

In some embodiments, the anti-Psl antibody comprises a $V_H$ comprising the amino acid sequence of SEQ ID NO: 105, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 94, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 105 and a $V_L$ comprising the amino acid sequence of SEQ ID NO: 94. In some embodiments, the anti-Psl antibody comprises a $V_H$ comprising an HC-CDR1, an HC-CDR2 and an HC-CDR3 of the $V_H$ comprising the amino acid sequence of SEQ ID NO: 105; and a $V_L$ comprising an LC-CDR1, an LC-CDR2, and an LC-CDR3 of the $V_L$ comprising the amino acid sequence of SEQ ID NOs: 94.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 166, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 166; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 166; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 166; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65.

In some embodiments, the anti-Psl antibody comprises a $V_H$ comprising the amino acid sequence of SEQ ID NO: 106, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 94, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 106 and a $V_L$ comprising the amino acid sequence of SEQ ID NO: 94. In some embodiments, the anti-Psl antibody comprises a $V_H$ comprising an HC-CDR1, an HC-CDR2 and an HC-CDR3 of the $V_H$ comprising the amino acid sequence of SEQ ID NO: 106; and a $V_L$ comprising an LC-CDR1, an LC-CDR2, and an LC-CDR3 of the $V_L$ comprising the amino acid sequence of SEQ ID NOs: 94.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65.

In some embodiments, the anti-Psl antibody comprises a $V_H$ comprising the amino acid sequence of SEQ ID NO: 107, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 94, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 107 and a $V_L$ comprising the amino acid sequence of SEQ ID NO: 94. In some embodiments, the anti-Psl antibody comprises a $V_H$ comprising an HC-CDR1, an HC-CDR2 and an HC-CDR3 of the $V_H$ comprising the amino acid sequence of SEQ ID NO: 107; and a $V_L$ comprising an LC-CDR1, an LC-CDR2, and an LC-CDR3 of the $V_L$ comprising the amino acid sequence of SEQ ID NOs: 94.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 167, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 167; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 167; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 167; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65.

In some embodiments, the anti-Psl antibody comprises a $V_H$ comprising the amino acid sequence of SEQ ID NO: 108, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 94, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 108 and a $V_L$ comprising the amino acid sequence of SEQ ID NO: 94. In some embodiments, the anti-Psl antibody comprises a $V_H$ comprising an HC-CDR1, an HC-CDR2 and an HC-CDR3 of the $V_H$ comprising the amino acid sequence of SEQ ID NO: 108; and a $V_L$ comprising an LC-CDR1, an LC-CDR2, and an LC-CDR3 of the $V_L$ comprising the amino acid sequence of SEQ ID NOs: 94.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 168, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 168; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 168; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 168; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65.

In some embodiments, the anti-Psl antibody comprises a $V_H$ comprising the amino acid sequence of SEQ ID NO: 109, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 94, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 109 and a $V_L$ comprising the amino acid sequence of SEQ ID NO: 94. In some embodiments, the anti-Psl antibody comprises a $V_H$ comprising an HC-CDR1, an HC-CDR2 and an HC-CDR3 of the $V_H$ comprising the amino acid sequence of SEQ ID NO: 109; and a $V_L$ comprising an LC-CDR1, an LC-CDR2, and an LC-CDR3 of the $V_L$ comprising the amino acid sequence of SEQ ID NOs: 94.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 199, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 199. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 199. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 199.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 111, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 111. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 111.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 200, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 200. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 200. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 200.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 112, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 112. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 112.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 76, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 76. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 76. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 76.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 113, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 113. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 113.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 201, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 201. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 201. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 201.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 114, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 114. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 114.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 202, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 202. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 202. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 202.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 115, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 115. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 115.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 116, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 116. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 116.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 203, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 203. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 203. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 203.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 117, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 117. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 117.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 204, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 204. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 204. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 204.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 118, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 118. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 118.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 205, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 205. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 205. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 205.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 119, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 119. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 119.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 206, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 206. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 206. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 206.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 120, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 120. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 120.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 207, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 207. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 207. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 207.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 121, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 121. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 121.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 208, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 208. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 208. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 208.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 122, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 122. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 122.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 77, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 77. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 77. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 77.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 123, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 123. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 123.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 209, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 209. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 209. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 209.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 124, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 124. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 124.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 210, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 210. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 210. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 210.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 125, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 125. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 125.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 126, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 126. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 126.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 212, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 212. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 212. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 27; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 212.

In some embodiments, the anti-Psl antibody comprises a $V_H$ comprising the amino acid sequence of SEQ ID NO: 82, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 127, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 82 and a $V_L$ comprising the amino acid sequence of SEQ ID NO: 127. In some embodiments, the anti-Psl antibody comprises a $V_H$ comprising an HC-CDR1, an HC-CDR2 and an HC-CDR3 of the $V_H$ comprising the amino acid sequence of SEQ ID NO: 82; and a $V_L$ comprising an LC-CDR1, an LC-CDR2, and an LC-CDR3 of the $V_L$ comprising the amino acid sequence of SEQ ID NOs: 127.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 76, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 76. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 76. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 76.

In some embodiments, the anti-Psl antibody comprises a $V_H$ comprising the amino acid sequence of SEQ ID NO: 107, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 113, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 107 and a $V_L$ comprising the amino acid sequence of SEQ ID NO: 113. In some embodiments, the anti-Psl antibody comprises a $V_H$ comprising an HC-CDR1, an HC-CDR2 and an HC-CDR3 of the $V_H$ comprising the amino acid sequence of SEQ ID NO: 107; and a $V_L$ comprising an LC-CDR1, an LC-CDR2, and an LC-CDR3 of the $V_L$ comprising the amino acid sequence of SEQ ID NOs: 113.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 77, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 77. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 77. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 77.

In some embodiments, the anti-Psl antibody comprises a $V_H$ comprising the amino acid sequence of SEQ ID NO: 107, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 123, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 107 and a $V_L$ comprising the amino acid sequence of SEQ ID NO: 123. In some embodiments, the anti-Psl antibody comprises a $V_H$ comprising an HC-CDR1, an HC-CDR2 and an HC-CDR3 of the $V_H$ comprising the amino acid sequence of SEQ ID NO: 107; and a $V_L$ comprising an LC-CDR1, an LC-CDR2, and an LC-CDR3 of the $V_L$ comprising the amino acid sequence of SEQ ID NOs: 123.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 35; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 78.

In some embodiments, the anti-Psl antibody comprises a $V_H$ comprising the amino acid sequence of SEQ ID NO: 107, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 116, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 107 and a $V_L$ comprising the amino acid sequence of SEQ ID NO: 116. In some embodiments, the anti-Psl antibody comprises a $V_H$ comprising an HC-CDR1, an HC-CDR2 and an HC-CDR3 of the $V_H$ comprising the amino acid sequence of SEQ ID NO: 107; and a $V_L$ comprising an LC-CDR1, an LC-CDR2, and an LC-CDR3 of the $V_L$ comprising the amino acid sequence of SEQ ID NOs: 116.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 169, or a variant thereof comprising up to about 5 amino acid substitutions in the HC-CDRs; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 169; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that specifically competes with an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 169; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65. In some embodiments, there is provided an anti-Psl antibody that binds to the same epitope as an antibody comprising a $V_H$ comprising: an HC-CDR1 comprising the amino acid sequence of SEQ ID NO: 4, an HC-CDR2 comprising the amino acid sequence of SEQ ID NO: 16, and an HC-CDR3 comprising the amino acid sequence of SEQ ID NO: 169; and a $V_L$ comprising: an LC-CDR1 comprising the amino acid sequence of SEQ ID NO: 40, an LC-CDR2 comprising the amino acid sequence of SEQ ID NO: 54, and an LC-CDR3 comprising the amino acid sequence of SEQ ID NO: 65.

In some embodiments, the anti-Psl antibody comprises a $V_H$ comprising the amino acid sequence of SEQ ID NO: 110, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 94, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 110 and a $V_L$ comprising the amino acid sequence of SEQ ID NO: 94. In some embodiments, the anti-Psl antibody comprises a $V_H$ comprising an HC-CDR1, an HC-CDR2 and an HC-CDR3 of the $V_H$ comprising the amino acid sequence of SEQ ID NO: 110; and a $V_L$ comprising an LC-CDR1, an LC-CDR2, and an LC-CDR3 of the $V_L$ comprising the amino acid sequence of SEQ ID NOs: 94.

In one aspect, the present application provides an isolated anti-Psl antibody, wherein the anti-Psl antibody comprises a $V_H$ comprising an HC-CDR1 comprising SSGDYWG (SEQ ID NO: 1), or a variant thereof comprising up to about 3 amino acid substitutions; an HC-CDR2 comprising SIHNX₁GSTYYNPSLKG (SEQ ID NO: 213), or a variant thereof comprising up to about 3 amino acid substitutions, wherein X₁ is S, K, or Q; and an HC-CDR3 comprising QFGSETYYX₁GIX₂P (SEQ ID NO: 190), or a variant thereof comprising up to about 3 amino acid substitutions, wherein X₁ is N, S, V, T, or P, X₂ is D, Y, C, H, S, R, A, E, G, K, W, V, or Q; and a $V_L$ comprising an LC-CDR1 comprising RSSQSLLHSX₁GYNYLD (SEQ ID NO: 184), or a variant thereof comprising up to about 3 amino acid substitutions, wherein X₁ is N, A, V, F, R, G, H, Q, W, or P; an LC-CDR2 comprising LGSNRAS (SEQ ID NO: 51), or a variant thereof comprising up to about 3 amino acid substitutions; and an LC-CDR3 comprising MQALQTPX₁T (SEQ ID NO: 214), wherein X₁ is R or Y, or a variant thereof comprising up to about 3 amino acid substitutions.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 24, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 24; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 24; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 24; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 79, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 79 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 79; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 170, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 170; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 170; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 170; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 128, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 128 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 128; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 171, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 171; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 171; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 171; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 129, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 129 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 129; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 172, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 172; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 172; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 172; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 130, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 130 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 130; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 173, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 173; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 173; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 173; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 131, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 131 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 131; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 132, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 132 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 132; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 174, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 174; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 174; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 174; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 133, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 133 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 133; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 175, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 175; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 175; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 175; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 134, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 134 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 134; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 176, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 176; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 176; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 176; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 135, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 135 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 135; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 177, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 177; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 177; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 177; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 136, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 136 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 136;

and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 178, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 178; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 178; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 178; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 137, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 137 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 137; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 179, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 179; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 179; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 179; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 138, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 138 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 138; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 180, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 180; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 180; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 180; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 139, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 139 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 139; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising: an LC-CDR1 comprising the amino acid sequence of SEQ ID NO: 191, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 191, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 191, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 191, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 140, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 151 and a $V_L$ comprising the amino acid sequence of SEQ ID NO: 140. In some embodiments, the anti-Psl antibody comprises a $V_H$ comprising an HC-CDR1, an HC-CDR2 and an HC-CDR3 of the $V_H$ comprising the amino acid sequence of SEQ ID NO: 151; and a $V_L$ comprising an LC-CDR1, an LC-CDR2, and an LC-CDR3 of the $V_L$ comprising the amino acid sequence of SEQ ID NOs: 140.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising: an LC-CDR1 comprising the amino acid sequence of SEQ ID NO: 192, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 192, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 192, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 192, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 141, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 151 and a $V_L$ comprising the amino acid sequence of SEQ ID NO: 141. In some embodiments, the anti-Psl antibody comprises a $V_H$ comprising an HC-CDR1, an HC-CDR2 and an HC-CDR3 of the $V_H$ comprising the amino acid sequence of SEQ ID NO: 151; and a $V_L$ comprising an LC-CDR1, an LC-CDR2, and an LC-CDR3 of the $V_L$ comprising the amino acid sequence of SEQ ID NOs: 141.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising: an LC-CDR1 comprising the amino acid sequence of SEQ ID NO: 193, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 193, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 193, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 193, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 142, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 151 and a $V_L$ comprising the amino acid sequence of SEQ ID NO: 142. In some embodiments, the anti-Psl antibody comprises a $V_H$ comprising an HC-CDR1, an HC-CDR2 and an HC-CDR3 of the $V_H$ comprising the amino acid sequence of SEQ ID NO: 151; and a $V_L$ comprising an LC-CDR1, an LC-CDR2, and an LC-CDR3 of the $V_L$ comprising the amino acid sequence of SEQ ID NOs: 142.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 143, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 151 and a $V_L$ comprising the amino acid sequence of SEQ ID NO: 143. In some embodiments, the anti-Psl antibody comprises a $V_H$ comprising an HC-CDR1, an HC-CDR2 and an HC-CDR3 of the $V_H$ comprising the amino acid sequence of SEQ ID NO: 151; and a $V_L$ comprising an LC-CDR1, an LC-CDR2, and an LC-CDR3 of the $V_L$ comprising the amino acid sequence of SEQ ID NOs: 143.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising: an LC-CDR1 comprising the amino acid sequence of SEQ ID NO: 194, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 194, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 194, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 194, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 144, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 151 and a $V_L$ comprising the amino acid sequence of SEQ ID NO: 144. In some embodiments, the anti-Psl antibody comprises a $V_H$ comprising an HC-CDR1, an HC-CDR2 and an HC-CDR3 of the $V_H$ comprising the amino acid sequence of SEQ ID NO: 151; and a $V_L$ comprising an LC-CDR1, an LC-CDR2, and an LC-CDR3 of the $V_L$ comprising the amino acid sequence of SEQ ID NOs: 144.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising: an LC-CDR1 comprising the amino acid sequence of SEQ ID NO: 195, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 195, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 195, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 195, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO:

151, or a variant thereof having at least about 90% (for example at least about any of 91%, 92%, 93%, 94%, 95%, 96%, 97%, 98%, or 99%) sequence identity, and a V$_L$ comprising the amino acid sequence of SEQ ID NO: 145, or a variant thereof having at least about 90% (for example at least about any of 91%, 92%, 93%, 94%, 95%, 96%, 97%, 98%, or 99%) sequence identity. In some embodiments, the anti-Psl antibody comprises a V$_H$ comprising the amino acid sequence of SEQ ID NO: 151 and a V$_L$ comprising the amino acid sequence of SEQ ID NO: 145. In some embodiments, the anti-Psl antibody comprises a V$_H$ comprising an HC-CDR1, an HC-CDR2 and an HC-CDR3 of the V$_H$ comprising the amino acid sequence of SEQ ID NO: 151; and a V$_L$ comprising an LC-CDR1, an LC-CDR2, and an LC-CDR3 of the V$_L$ comprising the amino acid sequence of SEQ ID NOs: 145.

In some embodiments, the anti-Psl antibody comprises a V$_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a V$_L$ comprising: an LC-CDR1 comprising the amino acid sequence of SEQ ID NO: 196, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a V$_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a V$_L$ comprising: an LC-CDR1 comprising the amino acid sequence of SEQ ID NO: 196, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a V$_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a V$_L$ comprising: an LC-CDR1 comprising the amino acid sequence of SEQ ID NO: 196, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a V$_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a V$_L$ comprising: an LC-CDR1 comprising the amino acid sequence of SEQ ID NO: 196, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a V$_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a V$_L$ comprising the amino acid sequence of SEQ ID NO: 146, or a variant thereof having at least about 90% (for example at least about any of 91%, 92%, 93%, 94%, 95%, 96%, 97%, 98%, or 99%) sequence identity. In some embodiments, the anti-Psl antibody comprises a V$_H$ comprising the amino acid sequence of SEQ ID NO: 151 and a V$_L$ comprising the amino acid sequence of SEQ ID NO: 146. In some embodiments, the anti-Psl antibody comprises a V$_H$ comprising an HC-CDR1, an HC-CDR2 and an HC-CDR3 of the V$_H$ comprising the amino acid sequence of SEQ ID NO: 151; and a V$_L$ comprising an LC-CDR1, an LC-CDR2, and an LC-CDR3 of the V$_L$ comprising the amino acid sequence of SEQ ID NOs: 146.

In some embodiments, the anti-Psl antibody comprises a V$_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a V$_L$ comprising: an LC-CDR1 comprising the amino acid sequence of SEQ ID NO: 197, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a V$_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a V$_L$ comprising: an LC-CDR1 comprising the amino acid sequence of SEQ ID NO: 197, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a V$_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a V$_L$ comprising: an LC-CDR1 comprising the amino acid sequence of SEQ ID NO: 197, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a V$_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a V$_L$ comprising: an LC-CDR1 comprising the amino acid sequence of SEQ ID NO: 197, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a V$_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a V$_L$ comprising the amino acid sequence of SEQ ID NO: 147, or a variant thereof having at least about 90% (for example at least about any of 91%, 92%, 93%, 94%, 95%, 96%, 97%, 98%, or 99%) sequence identity. In some embodiments, the anti-Psl antibody comprises a V$_H$ comprising the amino acid sequence of SEQ ID NO: 151 and a V$_L$ comprising the amino acid sequence of SEQ ID NO: 147. In some embodiments, the anti-Psl antibody comprises a V$_H$ comprising an HC-CDR1, an HC-CDR2 and an HC-CDR3 of the V$_H$ comprising the amino acid sequence of SEQ ID NO: 151; and a $V_L$ comprising an LC-CDR1, an LC-CDR2, and an LC-CDR3 of the $V_L$ comprising the amino acid sequence of SEQ ID NOs: 147.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36, or a variant thereof comprising up to about 5 amino acid substitutions in the HC-CDRs; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 132, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 143, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 132 and a $V_L$ comprising the amino acid sequence of SEQ ID NO: 143. In some embodiments, the anti-Psl antibody comprises a $V_H$ comprising an HC-CDR1, an HC-CDR2 and an HC-CDR3 of the $V_H$ comprising the amino acid sequence of SEQ ID NO: 132; and a $V_L$ comprising an LC-CDR1, an LC-CDR2, and an LC-CDR3 of the $V_L$ comprising the amino acid sequence of SEQ ID NOs: 143.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising: an LC-CDR1 comprising the amino acid sequence of SEQ ID NO: 198, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 198, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 198, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 198, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 148, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 151 and a $V_L$ comprising the amino acid sequence of SEQ ID NO: 148. In some embodiments, the anti-Psl antibody comprises a $V_H$ comprising an HC-CDR1, an HC-CDR2 and an HC-CDR3 of the $V_H$ comprising the amino acid sequence of SEQ ID NO: 151; and a $V_L$ comprising an LC-CDR1, an LC-CDR2, and an LC-CDR3 of the $V_L$ comprising the amino acid sequence of SEQ ID NOs: 148.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 181, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 181; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 181; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 181; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 149, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 149 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 149; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 164, and an HC-CDR3 comprising the amino acid sequence of SEQ ID NO: 24, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 164, and an HC-CDR3 comprising the amino acid sequence of SEQ ID NO: 24; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 164, and an HC-CDR3 comprising the amino acid sequence of SEQ ID NO: 24; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 164, and an HC-CDR3 comprising the amino acid sequence of SEQ ID NO: 24; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 150, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 150 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 150; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 151 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 151; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 183, or a variant thereof comprising up to about 5 amino acid substitutions in the HC-CDRs; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 183; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 183; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 183; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 152, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 143, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 152 and a $V_L$ comprising the amino acid sequence of SEQ ID NO: 143. In some embodiments, the anti-Psl antibody comprises a $V_H$ comprising an HC-CDR1, an HC-CDR2 and an HC-CDR3 of the $V_H$ comprising the amino acid sequence of SEQ ID NO: 152; and a $V_L$ comprising an LC-CDR1, an LC-CDR2, and an LC-CDR3 of the $V_L$ comprising the amino acid sequence of SEQ ID NOs: 143.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 164, and an HC-CDR3 comprising the amino acid sequence of SEQ ID NO: 183, or a variant thereof comprising up to about 5 amino acid substitutions in the HC-CDRs; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 164, and an HC-CDR3 comprising the amino acid sequence of SEQ ID NO: 183; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 164, and an HC-CDR3 comprising the amino acid sequence of SEQ ID NO: 183; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 164, and an HC-CDR3 comprising the amino acid sequence of SEQ ID NO: 183; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 153, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 143, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 153 and a $V_L$ comprising the amino acid sequence of SEQ ID NO: 143. In some embodiments, the anti-Psl antibody comprises a $V_H$ comprising an HC-CDR1, an HC-CDR2 and an HC-CDR3 of the $V_H$ comprising the amino acid sequence of SEQ ID NO: 153; and a $V_L$ comprising an LC-CDR1, an LC-CDR2, and an LC-CDR3 of the $V_L$ comprising the amino acid sequence of SEQ ID NOs: 143.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 181, or a variant thereof comprising up to about 5 amino acid substitutions in the HC-CDRs; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 181; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 181; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 181; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 149, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 143, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 149 and a $V_L$ comprising the amino acid sequence of SEQ ID NO: 143. In some embodiments, the anti-Psl antibody comprises a $V_H$ comprising an HC-CDR1, an HC-CDR2 and an HC-CDR3 of the $V_H$ comprising the amino acid sequence of SEQ ID NO: 149; and a $V_L$ comprising an LC-CDR1, an LC-CDR2, and an LC-CDR3 of the $V_L$ comprising the amino acid sequence of SEQ ID NOs: 143.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 185, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 185; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 185; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 185; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 154, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 154 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 154; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 186, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 186; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 186; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 186; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 155, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 155 and a $V_L$ comprising the amino acid sequence of SEQ ID NO: 91. In some embodiments, the anti-Psl antibody comprises a $V_H$ comprising an HC-CDR1, an HC-CDR2 and an HC-CDR3 of the $V_H$ comprising the amino acid sequence of SEQ ID NO: 155; and a $V_L$ comprising an LC-CDR1, an LC-CDR2, and an LC-CDR3 of the $V_L$ comprising the amino acid sequence of SEQ ID NOs: 91.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 187, or a variant thereof comprising up to about 5 amino acid substitutions in the HC-CDRs; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 187; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 187; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 187; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 156, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 143, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 156 and a $V_L$ comprising the amino acid sequence of SEQ ID NO: 143. In some embodiments, the anti-Psl antibody comprises a $V_H$ comprising an HC-CDR1, an HC-CDR2 and an HC-CDR3 of the $V_H$ comprising the amino acid sequence of SEQ ID NO: 156;

and a $V_L$ comprising an LC-CDR1, an LC-CDR2, and an LC-CDR3 of the $V_L$ comprising the amino acid sequence of SEQ ID NOs: 143.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 188, or a variant thereof comprising up to about 5 amino acid substitutions in the HC-CDRs; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 188; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 188; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 188; and a $V_L$ comprising: an LC-CDR1 comprising the amino acid sequence of SEQ ID NO: 50, an LC-CDR2 comprising the amino acid sequence of SEQ ID NO: 51, and an LC-CDR3 comprising the amino acid sequence of SEQ ID NO: 62.

In some embodiments, the anti-Psl antibody comprises a $V_H$ comprising the amino acid sequence of SEQ ID NO: 157, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 143, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 157 and a $V_L$ comprising the amino acid sequence of SEQ ID NO: 143. In some embodiments, the anti-Psl antibody comprises a $V_H$ comprising an HC-CDR1, an HC-CDR2 and an HC-CDR3 of the $V_H$ comprising the amino acid sequence of SEQ ID NO: 157; and a $V_L$ comprising an LC-CDR1, an LC-CDR2, and an LC-CDR3 of the $V_L$ comprising the amino acid sequence of SEQ ID NOs: 143.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182, or a variant thereof comprising up to about 5 amino acid substitutions in the HC-CDRs; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 69, or a variant thereof comprising up to about 5 amino acid substitutions in the LC-CDRs.

In some embodiments, the anti-Psl antibody comprises a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 69. In some embodiments, there is provided an anti-Psl antibody that specifically competes with an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 69. In some embodiments, there is provided an anti-Psl antibody that binds to the same epitope as an antibody comprising a $V_H$ comprising: an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising: an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 69.

In some embodiments, the anti-Psl antibody comprises a $V_H$ comprising the amino acid sequence of SEQ ID NO: 151, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 98, or a variant thereof having at least about 90% (for example at least about any of 91%, 92%, 93%, 94%, 95%, 96%, 97%, 98%, or 99%) sequence identity. In some embodiments, the anti-Psl antibody comprises a $V_H$ comprising the amino acid sequence of SEQ ID NO: 151 and a $V_L$ comprising the amino acid sequence of SEQ ID NO: 98. In some embodiments, the anti-Psl antibody comprises a $V_H$ comprising an HC-CDR1, an HC-CDR2 and an HC-CDR3 of the $V_H$ comprising the amino acid sequence of SEQ ID NO: 151; and a $V_L$ comprising an LC-CDR1, an LC-CDR2, and an LC-CDR3 of the $V_L$ comprising the amino acid sequence of SEQ ID NOs: 98.

In some embodiments, competition assays may be used to identify a monoclonal antibody that competes with an anti-Psl antibody described herein for binding to Psl. Competition assays can be used to determine whether two antibodies bind the same epitope by recognizing identical or sterically overlapping epitopes or one antibody competitively inhibits binding of another antibody to the antigen. In certain embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 5000 or more.

In some embodiments, the antibody that competes with an anti-Psl antibody described herein is a chimeric, humanized or human antibody.

Exemplary anti-Psl antibody sequences are shown in Tables 2 and 3, wherein the CDR numbering is according to the EU index of Kabat. Those skilled in the art will recognize that many algorithms are known for prediction of CDR positions and for delimitation of antibody heavy chain and light chain variable regions. Anti-Psl antibodies comprising CDRs, $V_H$ and/or $V_L$ sequences from antibodies described herein, but based on prediction algorithms other than those exemplified in the tables below, are within the scope of this invention.

TABLE 2

| Exemplary anti-Psl antibody CDR sequences. | | | |
|---|---|---|---|
| Name | CDR H1 | CDR H2 | CDR H3 |
| P59 | SSGDYWG (SEQ ID NO: 1) | SIHNQGSTYYNPSLKG (SEQ ID NO: 13) | QFGSETYYTGIDP (SEQ ID NO: 24) |
| 2A2 | STSYWA (SEQ ID NO: 2) | TIYYDGYTFYNPSLKS (SEQ ID NO: 14) | HDSGQQLINNWFDP (SEQ ID NO: 25) |
| 6G7 | SDSYWG (SEQ ID NO: 3) | TIYYDGTTFYNPSLRS (SEQ ID NO: 15) | HESGQQLVNNWFDP (SEQ ID NO: 26) |
| 7H9 | IHSVH (SEQ ID NO: 4) | TIISSGTTTTYAQSFQD (SEQ ID NO: 16) | DGDS (SEQ ID NO: 27) |
| 3F12 | DYYWS (SEQ ID NO: 5) | YIHSSGSTDYNPSLKS (SEQ ID NO: 17) | AQGGSRRTLDY (SEQ ID NO: 28) |
| 1D10 | SDYWS (SEQ ID NO: 6) | YISDSGSTDYNPSLKS (SEQ ID NO: 18) | ATVTTYSFDY (SEQ ID NO: 29) |
| 3G8 | STSYW (SEQ ID NO: 7) | TIYYDGYTFYNPSLKS (SEQ ID NO: 14) | HDSGQQLINNWFDP (SEQ ID NO: 25) |
| 4D1 | SGYYWS (SEQ ID NO: 8) | SIHHSGSTYYNPSLQS (SEQ ID NO: 19) | AEYYYESSGPLFDY (SEQ ID NO: 30) |
| 8D10 | SDSYWG (SEQ ID NO: 3) | TIYYDGTTFYNPSLRS (SEQ ID NO: 15) | HESGQQLVNNWFDP (SEQ ID NO: 26) |
| 8H5 | SGSYYWS (SEQ ID NO: 9) | FIHNNGYTNYNPSLKS (SEQ ID NO: 20) | GETYESSGYYDY (SEQ ID NO: 31) |
| 4C1 | SSDYYWG (SEQ ID NO: 10) | SINYAGSTYYNPSLKS (SEQ ID NO: 21) | QNTARGISTDF (SEQ ID NO: 32) |
| 9C2 | SSSSYWG (SEQ ID NO: 11) | SIYDDGTTFYNPSFKS (SEQ ID NO: 22) | TPYGDYASYFFDY (SEQ ID NO: 33) |
| P25 | GTYVH (SEQ ID NO: 12) | WIDRNRGGTNYAQKFQG (SEQ ID NO: 23) | DPG (SEQ ID NO: 34) |
| Name | CDR L1 | CDR L2 | CDR L3 |
| P59 | RSSQSLLHSNGYNYLD (SEQ ID NO: 37) | LGSNRAS (SEQ ID NO: 51) | MQALQTPYT (SEQ ID NO: 62) |
| 2A2 | RASQSIGYYLN (SEQ ID NO: 38) | AASSLQS (SEQ ID NO: 52) | QQSYTIPYT (SEQ ID NO: 63) |
| 6G7 | RASQSVSSNLA (SEQ ID NO: 39) | GASTRAT (SEQ ID NO: 53) | QQSGDSLVT (SEQ ID NO: 64) |
| 7H9 | RASQGISSWLA (SEQ ID NO: 40) | HASTLES (SEQ ID NO: 54) | LQANSLPHT (SEQ ID NO: 65) |
| 3F12 | RASQTISSYLN (SEQ ID NO: 41) | AASSLQS (SEQ ID NO: 52) | QQSYSTPYT (SEQ ID NO: 66) |
| 1D10 | RASQGINRWLA (SEQ ID NO: 42) | ATSTLQS (SEQ ID NO: 55) | QQGYTLPPT (SEQ ID NO: 67) |

TABLE 2-continued

| Exemplary anti-Psl antibody CDR sequences. | | |
|---|---|---|
| 3G8 | RASQGISSYLA<br>(SEQ ID NO: 43) | AASRLQS<br>(SEQ ID NO: 56) | QQSFSVPIT<br>(SEQ ID NO: 68) |
| 4D1 | QASQDISNSLN<br>(SEQ ID NO: 44) | DASNLET<br>(SEQ ID NO: 57) | QQSYTAPYT<br>(SEQ ID NO: 70) |
| 8D10 | RASQSISSYLN<br>(SEQ ID NO: 45) | TASNLQT<br>(SEQ ID NO: 58) | QQSYDSPLT<br>(SEQ ID NO: 71) |
| 8H5 | RASQSIGRYLN<br>(SEQ ID NO: 46) | AASSLQS<br>(SEQ ID NO: 52) | QQANSLPFT<br>(SEQ ID NO: 72) |
| 4C1 | RASQSVSSSYLA<br>(SEQ ID NO: 47) | GASSRAT<br>(SEQ ID NO: 59) | QHYDNSLT<br>(SEQ ID NO: 73) |
| 9C2 | KSSQSLLHSDGKTYLY<br>(SEQ ID NO: 48) | EVSNRFS<br>(SEQ ID NO: 60) | MQSLQLPLT<br>(SEQ ID NO: 74) |
| P25 | RSSQSLLHSNGNNYLD<br>(SEQ ID NO: 49) | MGSNRAS<br>(SEQ ID NO: 61) | MQGLQTPLT<br>(SEQ ID NO: 75) |

TABLE 3

| Exemplary anti-Psl antibody mutations CDR sequences. | | | |
|---|---|---|---|
| Mutations | CDR H1 | CDR H2 | CDR H3 |
| 7H9-m01 | IHSVH<br>(SEQ ID NO: 4) | TIISSGTTTTYAQSFQD<br>(SEQ ID NO: 16) | DGDA<br>(SEQ ID NO: 165) |
| 7H9-m02 | IHSVH<br>(SEQ ID NO: 4) | TIISSGTTTTYAQSFQD<br>(SEQ ID NO: 16) | DGDT<br>(SEQ ID NO: 166) |
| 7H9-m03 | IHSVH<br>(SEQ ID NO: 4) | TIISSGTTTTYAQSFQD<br>(SEQ ID NO: 16) | DGTS<br>(SEQ ID NO: 35) |
| 7H9-m04 | IHSVH<br>(SEQ ID NO: 4) | TIISSGTTTTYAQSFQD<br>(SEQ ID NO: 16) | YGDS<br>(SEQ ID NO: 167) |
| 7H9-m05 | IHSVH<br>(SEQ ID NO: 4) | TIISSGTTTTYAQSFQD<br>(SEQ ID NO: 16) | NGDS<br>(SEQ ID NO: 168) |
| 7H9-m06 | IHSVH<br>(SEQ ID NO: 4) | TIISSGTTTTYAQSFQD<br>(SEQ ID NO: 16) | DGDS<br>(SEQ ID NO: 27) |
| 7H9-m07 | IHSVH<br>(SEQ ID NO: 4) | TIISSGTTTTYAQSFQD<br>(SEQ ID NO: 16) | DGDS<br>(SEQ ID NO: 27) |
| 7H9-m08 | IHSVH<br>(SEQ ID NO: 4) | TIISSGTTTTYAQSFQD<br>(SEQ ID NO: 16) | DGDS<br>(SEQ ID NO: 27) |
| 7H9-m09 | IHSVH<br>(SEQ ID NO: 4) | TIISSGTTTTYAQSFQD<br>(SEQ ID NO: 16) | DGDS<br>(SEQ ID NO: 27) |
| 7H9-m10 | IHSVH<br>(SEQ ID NO: 4) | TIISSGTTTTYAQSFQD<br>(SEQ ID NO: 16) | DGDS<br>(SEQ ID NO: 27) |
| 7H9-m11 | IHSVH<br>(SEQ ID NO: 4) | TIISSGTTTTYAQSFQD<br>(SEQ ID NO: 16) | DGDS<br>(SEQ ID NO: 27) |
| 7H9-m12 | IHSVH<br>(SEQ ID NO: 4) | TIISSGTTTTYAQSFQD<br>(SEQ ID NO: 16) | DGDS<br>(SEQ ID NO: 27) |
| 7H9-m13 | IHSVH<br>(SEQ ID NO: 4) | TIISSGTTTTYAQSFQD<br>(SEQ ID NO: 16) | DGDS<br>(SEQ ID NO: 27) |
| 7H9-m14 | IHSVH<br>(SEQ ID NO: 4) | TIISSGTTTTYAQSFQD<br>(SEQ ID NO: 16) | DGDS<br>(SEQ ID NO: 27) |
| 7H9-m15 | IHSVH<br>(SEQ ID NO: 4) | TIISSGTTTTYAQSFQD<br>(SEQ ID NO: 16) | DGDS<br>(SEQ ID NO: 27) |
| 7H9-m16 | IHSVH<br>(SEQ ID NO: 4) | TIISSGTTTTYAQSFQD<br>(SEQ ID NO: 16) | DGDS<br>(SEQ ID NO: 27) |

TABLE 3-continued

Exemplary anti-Psl antibody mutations CDR sequences.

| 7H9-m17 | IHSVH (SEQ ID NO: 4) | TIISSGTTTTYAQSFQD (SEQ ID NO: 16) | DGDS (SEQ ID NO: 27) |
|---|---|---|---|
| 7H9-m18 | IHSVH (SEQ ID NO: 4) | TIISSGTTTTYAQSFQD (SEQ ID NO: 16) | DGDS (SEQ ID NO: 27) |
| 7H9-m19 | IHSVH (SEQ ID NO: 4) | TIISSGTTTTYAQSFQD (SEQ ID NO: 16) | DGDS (SEQ ID NO: 27) |
| 7H9-m20 | IHSVH (SEQ ID NO: 4) | TIISSGTTTTYAQSFQD (SEQ ID NO: 16) | DGDS (SEQ ID NO: 27) |
| 7H9-m21 | IHSVH (SEQ ID NO: 4) | TIISSGTTTTYAQSFQD (SEQ ID NO: 16) | DGDS (SEQ ID NO: 27) |
| 7H9-m22 | IHSVH (SEQ ID NO: 4) | TIISSGTTTTYAQSFQD (SEQ ID NO: 16) | DGDS (SEQ ID NO: 27) |
| 7H9-m23 | IHSVH (SEQ ID NO: 4) | TIISSGTTTTYAQSFQD (SEQ ID NO: 16) | DGTS (SEQ ID NO: 35) |
| 7H9-m24 | IHSVH (SEQ ID NO: 4) | TIISSGTTTTYAQSFQD (SEQ ID NO: 16) | DGTS (SEQ ID NO: 35) |
| 7H9-m25 | IHSVH (SEQ ID NO: 4) | TIISSGTTTTYAQSFQD (SEQ ID NO: 16) | DGTS (SEQ ID NO: 35) |
| 7H9-m26 | IHSVH (SEQ ID NO: 4) | TIISSGTTTTYAQSFQD (SEQ ID NO: 16) | DADS (SEQ ID NO: 169) |
| Consensus sequence of 7H9 variants V$_H$CDRS | IHSVH (SEQ ID NO: 4) | TIISSGTTTTYAQSFQD (SEQ ID NO: 16) | X$_1$X$_2$X$_3$X$_4$ (SEQ ID NO: 189), wherein X$_1$ is D, Y, or N X$_2$ is G or A X$_3$ is D or T X$_4$ is S, A or T |

| Mutations | CDR L1 | CDR L2 | CDRL3 |
|---|---|---|---|
| 7H9-m01 | RASQGISSWLA (SEQ ID NO: 40) | HASTLES (SEQ ID NO: 54) | LQANSLPHT (SEQ ID NO: 65) |
| 7H9-m02 | RASQGISSWLA (SEQ ID NO: 40) | HASTLES (SEQ ID NO: 54) | LQANSLPHT (SEQ ID NO: 65) |
| 7H9-m03 | RASQGISSWLA (SEQ ID NO: 40) | HASTLES (SEQ ID NO: 54) | LQANSLPHT (SEQ ID NO: 65) |
| 7H9-m04 | RASQGISSWLA (SEQ ID NO: 40) | HASTLES (SEQ ID NO: 54) | LQANSLPHT (SEQ ID NO: 65) |
| 7H9-m05 | RASQGISSWLA (SEQ ID NO: 40) | HASTLES (SEQ ID NO: 54) | LQANSLPHT (SEQ ID NO: 65) |
| 7H9-m06 | RASQGISSWLA (SEQ ID NO: 40) | HASTLES (SEQ ID NO: 54) | LQADSLPHT (SEQ ID NO: 199) |
| 7H9-m07 | RASQGISSWLA (SEQ ID NO: 40) | HASTLES (SEQ ID NO: 54) | LQAYSLPHT (SEQ ID NO: 200) |
| 7H9-m08 | RASQGISSWLA (SEQ ID NO: 40) | HASTLES (SEQ ID NO: 54) | LQAFSLPHT (SEQ ID NO: 76) |
| 7H9-m09 | RASQGISSWLA (SEQ ID NO: 40) | HASTLES (SEQ ID NO: 54) | LQALSLPHT (SEQ ID NO: 201) |
| 7H9-m10 | RASQGISSWLA (SEQ ID NO: 40) | HASTLES (SEQ ID NO: 54) | LQAGSLPHT (SEQ ID NO: 202) |
| 7H9-m11 | RASQGISSWLA (SEQ ID NO: 40) | HASTLES (SEQ ID NO: 54) | LQAKSLPHT (SEQ ID NO: 78) |
| 7H9-m12 | RASQGISSWLA (SEQ ID NO: 40) | HASTLES (SEQ ID NO: 54) | LQAHSLPHT (SEQ ID NO: 203) |
| 7H9-m13 | RASQGISSWLA (SEQ ID NO: 40) | HASTLES (SEQ ID NO: 54) | LQAASLPHT (SEQ ID NO: 204) |

TABLE 3-continued

Exemplary anti-Psl antibody mutations CDR sequences.

| 7H9-m14 | RASQGISSWLA (SEQ ID NO: 40) | HASTLES (SEQ ID NO: 54) | LQACSLPHT (SEQ ID NO: 205) |
| 7H9-m15 | RASQGISSWLA (SEQ ID NO: 40) | HASTLES (SEQ ID NO: 54) | LQAESLPHT (SEQ ID NO: 206) |
| 7H9-m16 | RASQGISSWLA (SEQ ID NO: 40) | HASTLES (SEQ ID NO: 54) | LQAQSLPHT (SEQ ID NO: 207) |
| 7H9-m17 | RASQGISSWLA (SEQ ID NO: 40) | HASTLES (SEQ ID NO: 54) | LQARSLPHT (SEQ ID NO: 208) |
| 7H9-m18 | RASQGISSWLA (SEQ ID NO: 40) | HASTLES (SEQ ID NO: 54) | LQASSLPHT (SEQ ID NO: 77) |
| 7H9-m19 | RASQGISSWLA (SEQ ID NO: 40) | HASTLES (SEQ ID NO: 54) | LQATSLPHT (SEQ ID NO: 209) |
| 7H9-m20 | RASQGISSWLA (SEQ ID NO: 40) | HASTLES (SEQ ID NO: 54) | LQAVSLPHT (SEQ ID NO: 210) |
| 7H9-m21 | RASQGISSWLA (SEQ ID NO: 40) | HASTLES (SEQ ID NO: 54) | LQAWSLPHT (SEQ ID NO: 211) |
| 7H9-m22 | RASQGISSWLA (SEQ ID NO: 40) | HASTLES (SEQ ID NO: 54) | LQAPSLPHT (SEQ ID NO: 212) |
| 7H9-m23 | RASQGISSWLA (SEQ ID NO: 40) | HASTLES (SEQ ID NO: 54) | LQAFSLPHT (SEQ ID NO: 76) |
| 7H9-m24 | RASQGISSWLA (SEQ ID NO: 40) | HASTLES (SEQ ID NO: 54) | LQASSLPHT (SEQ ID NO: 77) |
| 7H9-m25 | RASQGISSWLA (SEQ ID NO: 40) | HASTLES (SEQ ID NO: 54) | LQAKSLPHT (SEQ ID NO: 78) |
| 7H9-m26 | RASQGISSWLA (SEQ ID NO: 40) | HASTLES (SEQ ID NO: 54) | LOANSLPHT (SEQ ID NO: 65) |
| Consensus sequence of 7H9 variants V$_L$CDRS | RASQGISSWLA (SEQ ID NO: 40) | HASTLES (SEQ ID NO: 54) | LQAX$_1$SLPHT (SEQ ID NO: 158), wherein X$_1$ is N, D, Y, F, P, G, K, H, A, C, E, Q, R, S, T, V, W or L |

TABLE 4

Exemplary anti-Psl antibody mutations CDR sequences.

| Mutations | CDR H1 | CDR H2 | CDR H3 |
| --- | --- | --- | --- |
| P59-m01 | SSGDYWG (SEQ ID NO: 1) | SIHNSGSTYYNPSLKG (SEQ ID NO: 163) | QFGSETYYNGIYP (SEQ ID NO: 170) |
| P59-m02 | SSGDYWG (SEQ ID NO: 1) | SIHNSGSTYYNPSLKG (SEQ ID NO: 163) | QFGSETYYNGICP (SEQ ID NO: 171) |
| P59-m03 | SSGDYWG (SEQ ID NO: 1) | SIHNSGSTYYNPSLKG (SEQ ID NO: 163) | QFGSETYYNGIHP (SEQ ID NO: 172) |
| P59-m04 | SSGDYWG (SEQ ID NO: 1) | SIHNSGSTYYNPSLKG (SEQ ID NO: 163) | QFGSETYYNGISP (SEQ ID NO: 173) |
| P59-m05 | SSGDYWG (SEQ ID NO: 1) | SIHNSGSTYYNPSLKG (SEQ ID NO: 163) | QFGSETYYNGIQP (SEQ ID NO: 36) |
| P59-m06 | SSGDYWG (SEQ ID NO: 1) | SIHNSGSTYYNPSLKG (SEQ ID NO: 163) | QFGSETYYNGIRP (SEQ ID NO: 174) |
| P59-m07 | SSGDYWG (SEQ ID NO: 1) | SIHNSGSTYYNPSLKG (SEQ ID NO: 163) | QFGSETYYNGIAP (SEQ ID NO: 175) |
| P59-m08 | SSGDYWG (SEQ ID NO: 1) | SIHNSGSTYYNPSLKG (SEQ ID NO: 163) | QFGSETYYNGIEP (SEQ ID NO: 176) |

TABLE 4-continued

Exemplary anti-Psl antibody mutations CDR sequences.

| P59-m09 | SSGDYWG (SEQ ID NO: 1) | SIHNSGSTYYNPSLKG (SEQ ID NO: 163) | QFGSETYYNGIGP (SEQ ID NO: 177) |
|---|---|---|---|
| P59-m10 | SSGDYWG (SEQ ID NO: 1) | SIHNSGSTYYNPSLKG (SEQ ID NO: 163) | QFGSETYYNGIKP (SEQ ID NO: 178) |
| P59-m11 | SSGDYWG (SEQ ID NO: 1) | SIHNSGSTYYNPSLKG (SEQ ID NO: 163) | QFGSETYYNGIWP (SEQ ID NO: 179) |
| P59-m12 | SSGDYWG (SEQ ID NO: 1) | SIHNSGSTYYNPSLKG (SEQ ID NO: 163) | QFGSETYYNGIVP (SEQ ID NO: 180) |
| P59-m13 | SSGDYWG (SEQ ID NO: 1) | SIHNSGSTYYNPSLKG (SEQ ID NO: 163) | QFGSETYYNGIDP (SEQ ID NO: 182) |
| P59-m14 | SSGDYWG (SEQ ID NO: 1) | SIHNSGSTYYNPSLKG (SEQ ID NO: 163) | QFGSETYYNGIDP (SEQ ID NO: 182) |
| P59-m15 | SSGDYWG (SEQ ID NO: 1) | SIHNSGSTYYNPSLKG (SEQ ID NO: 163) | QFGSETYYNGIDP (SEQ ID NO: 182) |
| P59-m16 | SSGDYWG (SEQ ID NO: 1) | SIHNSGSTYYNPSLKG (SEQ ID NO: 163) | QFGSETYYNGIDP (SEQ ID NO: 182) |
| P59-m17 | SSGDYWG (SEQ ID NO: 1) | SIHNSGSTYYNPSLKG (SEQ ID NO: 163) | QFGSETYYNGIDP (SEQ ID NO: 182) |
| P59-m18 | SSGDYWG (SEQ ID NO: 1) | SIHNSGSTYYNPSLKG (SEQ ID NO: 163) | QFGSETYYNGIDP (SEQ ID NO: 182) |
| P59-m19 | SSGDYWG (SEQ ID NO: 1) | SIHNSGSTYYNPSLKG (SEQ ID NO: 163) | QFGSETYYNGIDP (SEQ ID NO: 182) |
| P59-m20 | SSGDYWG (SEQ ID NO: 1) | SIHNSGSTYYNPSLKG (SEQ ID NO: 163) | QFGSETYYNGIDP (SEQ ID NO: 182) |
| P59-m21 | SSGDYWG (SEQ ID NO: 1) | SIHNSGSTYYNPSLKG (SEQ ID NO: 163) | QFGSETYYNGIQP (SEQ ID NO: 36) |
| P59-m22 | SSGDYWG (SEQ ID NO: 1) | SIHNSGSTYYNPSLKG (SEQ ID NO: 163) | QFGSETYYNGIDP (SEQ ID NO: 182) |
| P59-m23 | SSGDYWG (SEQ ID NO: 1) | SIHNQGSTYYNPSLKG (SEQ ID NO: 13) | QFGSETYYPGIDP (SEQ ID NO: 181) |
| P59-m24 | SSGDYWG (SEQ ID NO: 1) | SIHNKGSTYYNPSLKG (SEQ ID NO: 164) | QFGSETYYTGIDP (SEQ ID NO: 24) |
| P59-m25 | SSGDYWG (SEQ ID NO: 1) | SIHNSGSTYYNPSLKG (SEQ ID NO: 163) | QFGSETYYNGIDP (SEQ ID NO: 182) |
| P59-m26 | SSGDYWG (SEQ ID NO: 1) | SIHNQGSTYYNPSLKG (SEQ ID NO: 13) | QFGSETYYTGIQP (SEQ ID NO: 183) |
| P59-m27 | SSGDYWG (SEQ ID NO: 1) | SIHNKGSTYYNPSLKG (SEQ ID NO: 164) | QFGSETYYTGIQP (SEQ ID NO: 183) |
| P59-m28 | SSGDYWG (SEQ ID NO: 1) | SIHNQGSTYYNPSLKG (SEQ ID NO: 13) | QFGSETYYPGIDP (SEQ ID NO: 181) |
| P59-m29 | SSGDYWG (SEQ ID NO: 1) | SIHNSGSTYYNPSLKG (SEQ ID NO: 163) | QFGSETYYSGIDP (SEQ ID NO: 185) |
| P59-m30 | SSGDYWG (SEQ ID NO: 1) | SIHNSGSTYYNPSLKG (SEQ ID NO: 163) | QFGSETYYVGIDP (SEQ ID NO: 186) |
| P59-m31 | SSGDYWG (SEQ ID NO: 1) | SIHNSGSTYYNPSLKG (SEQ ID NO: 163) | QFGSETYYVGIQP (SEQ ID NO: 187) |
| P59-m32 | SSGDYWG (SEQ ID NO: 1) | SIHNSGSTYYNPSLKG (SEQ ID NO: 163) | QFGSETYYSGIQP (SEQ ID NO: 188 |
| P59-m33 | SSGDYWG (SEQ ID NO: 1) | SIHNSGSTYYNPSLKG (SEQ ID NO: 163) | QFGSETYYNGIDP (SEQ ID NO: 182) |

TABLE 4-continued

| Exemplary anti-Psl antibody mutations CDR sequences. | | |
|---|---|---|
| Consensus sequence of P59 variants $V_H$CDRS | SSGDYWG (SEQ ID NO: 1) | SIHNX1GSTYYNPSLKG (SEQ ID NO: 213), wherein $X_1$ is S, K, or Q | QFGSETYYX$_1$GIX$_2$P (SEQ ID NO:190), wherein $X_1$ is N, S, V, T, or P; $X_2$ is D, Y, C, H, S, R, A, E, G, K, W, V, or Q |
| 3F12-m01 | DYYWS (SEQ ID NO: 5) | YIHSSGSTDYNPSLKS (SEQ ID NO: 17) | AQGGSRRTLDY (SEQ ID NO: 28) |

| Mutations | CDR L1 | CDR L2 | CDRL3 |
|---|---|---|---|
| P59-m01 | RSSQSLLHSNGYNYLD (SEQ ID NO: 37) | LGSNRAS (SEQ ID NO: 51) | MQALQTPYT (SEQ ID NO: 62) |
| P59-m02 | RSSQSLLHSNGYNYLD (SEQ ID NO: 37) | LGSNRAS (SEQ ID NO: 51) | MQALQTPYT (SEQ ID NO: 62) |
| P59-m03 | RSSQSLLHSNGYNYLD (SEQ ID NO: 37) | LGSNRAS (SEQ ID NO: 51) | MQALQTPYT (SEQ ID NO: 62) |
| P59-m04 | RSSQSLLHSNGYNYLD (SEQ ID NO: 37) | LGSNRAS (SEQ ID NO: 51) | MQALQTPYT (SEQ ID NO: 62) |
| P59-m05 | RSSQSLLHSNGYNYLD (SEQ ID NO: 37) | LGSNRAS (SEQ ID NO: 51) | MQALQTPYT (SEQ ID NO: 62) |
| P59-m06 | RSSQSLLHSNGYNYLD (SEQ ID NO: 37) | LGSNRAS (SEQ ID NO: 51) | MQALQTPYT (SEQ ID NO: 62) |
| P59-m07 | RSSQSLLHSNGYNYLD (SEQ ID NO: 37) | LGSNRAS (SEQ ID NO: 51) | MQALQTPYT (SEQ ID NO: 62) |
| P59-m08 | RSSQSLLHSNGYNYLD (SEQ ID NO: 37) | LGSNRAS (SEQ ID NO: 51) | MQALQTPYT (SEQ ID NO: 62) |
| P59-m09 | RSSQSLLHSNGYNYLD (SEQ ID NO: 37) | LGSNRAS (SEQ ID NO: 51) | MQALQTPYT (SEQ ID NO: 62) |
| P59-m10 | RSSQSLLHSNGYNYLD (SEQ ID NO: 37) | LGSNRAS (SEQ ID NO: 51) | MQALQTPYT (SEQ ID NO: 62) |
| P59-m11 | RSSQSLLHSNGYNYLD (SEQ ID NO: 37) | LGSNRAS (SEQ ID NO: 51) | MQALQTPYT (SEQ ID NO: 62) |
| P59-m12 | RSSQSLLHSNGYNYLD (SEQ ID NO: 37) | LGSNRAS (SEQ ID NO: 51) | MQALQTPYT (SEQ ID NO: 62) |
| P59-m13 | RSSQSLLHSAGYNYLD (SEQ ID NO: 191) | LGSNRAS (SEQ ID NO: 51) | MQALQTPYT (SEQ ID NO: 62) |
| P59-m14 | RSSQSLLHSVGYNYLD (SEQ ID NO: 192) | LGSNRAS (SEQ ID NO: 51) | MQALQTPYT (SEQ ID NO: 62) |
| P59-m15 | RSSQSLLHSFGYNYLD (SEQ ID NO: 193) | LGSNRAS (SEQ ID NO: 51) | MQALQTPYT (SEQ ID NO: 62) |
| P59-m16 | RSSQSLLHSRGYNYLD (SEQ ID NO: 50) | LGSNRAS (SEQ ID NO: 51) | MQALQTPYT (SEQ ID NO: 62) |
| P59-m17 | RSSQSLLHSGGYNYLD (SEQ ID NO: 194) | LGSNRAS (SEQ ID NO: 51) | MQALQTPYT (SEQ ID NO: 62) |
| P59-m18 | RSSQSLLHSHGYNYLD (SEQ ID NO: 195) | LGSNRAS (SEQ ID NO: 51) | MQALQTPYT (SEQ ID NO: 62) |
| P59-m19 | RSSQSLLHSQGYNYLD (SEQ ID NO: 196) | LGSNRAS (SEQ ID NO: 51) | MQALQTPYT (SEQ ID NO: 62) |
| P59-m20 | RSSQSLLHSWGYNYLD (SEQ ID NO: 197) | LGSNRAS (SEQ ID NO: 51) | MQALQTPYT (SEQ ID NO: 62) |
| P59-m21 | RSSQSLLHSRGYNYLD (SEQ ID NO: 50) | LGSNRAS (SEQ ID NO: 51) | MQALQTPYT (SEQ ID NO: 62) |
| P59-m22 | RSSQSLLHSPGYNYLD (SEQ ID NO: 198) | LGSNRAS (SEQ ID NO: 51) | MQALQTPYT (SEQ ID NO: 62) |

TABLE 4-continued

Exemplary anti-Psl antibody mutations CDR sequences.

| P59-m23 | RSSQSLLHSNGYNYLD (SEQ ID NO: 37) | LGSNRAS (SEQ ID NO: 51) | MQALQTPYT (SEQ ID NO: 62) |
|---|---|---|---|
| P59-m24 | RSSQSLLHSNGYNYLD (SEQ ID NO: 37) | LGSNRAS (SEQ ID NO: 51) | MQALQTPYT (SEQ ID NO: 62) |
| P59-m25 | RSSQSLLHSNGYNYLD (SEQ ID NO: 37) | LGSNRAS (SEQ ID NO: 51) | MQALQTPYT (SEQ ID NO: 62) |
| P59-m26 | RSSQSLLHSRGYNYLD (SEQ ID NO: 50) | LGSNRAS (SEQ ID NO: 51) | MQALQTPYT (SEQ ID NO: 62) |
| P59-m27 | RSSQSLLHSRGYNYLD (SEQ ID NO: 50) | LGSNRAS (SEQ ID NO: 51) | MQALQTPYT (SEQ ID NO: 62) |
| P59-m28 | RSSQSLLHSRGYNYLD (SEQ ID NO: 50) | LGSNRAS (SEQ ID NO: 51) | MQALQTPYT (SEQ ID NO: 62) |
| P59-m29 | RSSQSLLHSNGYNYLD (SEQ ID NO: 37) | LGSNRAS (SEQ ID NO: 51) | MQALQTPYT (SEQ ID NO: 62) |
| P59-m30 | RSSQSLLHSNGYNYLD (SEQ ID NO: 37) | LGSNRAS (SEQ ID NO: 51) | MQALQTPYT (SEQ ID NO: 62) |
| P59-m31 | RSSQSLLHSRGYNYLD (SEQ ID NO: 50) | LGSNRAS (SEQ ID NO: 51) | MQALQTPYT (SEQ ID NO: 62) |
| P59-m32 | RSSQSLLHSRGYNYLD (SEQ ID NO: 50) | LGSNRAS (SEQ ID NO: 51) | MQALQTPYT (SEQ ID NO: 62) |
| P59-m33 | RSSQSLLHSNGYNYLD (SEQ ID NO: 37) | LGSNRAS (SEQ ID NO: 51) | MQALQTPRT (SEQ ID NO: 69) |
| Consensus sequence of P59 variants $V_L$CDRS | RSSQSLLHSX1GYNYLD (SEQ ID NO: 184), wherein $X_1$ is N, A, V, F, R, G, H, Q, W or P | LGSNRAS (SEQ ID NO: 51) | MQALQTPX$_1$T (SEQ ID NO: 214), wherein $X_1$ is R or Y |
| 3F12-m01 | RASQTISSYLN (SEQ ID NO: 41) | AASSLQS (SEQ ID NO: 52) | QQSYSTPYT (SEQ ID NO: 66) |

TABLE 5

Exemplary anti-Psl antibody $V_H$ and $V_L$ sequences.

| SEQ ID NO | Description | Sequence |
|---|---|---|
| 79 | P59$V_H$ | QVQLQQSGPGLVKPSETLSLTCTVSGGPITSSGDYWGWIRQPPGKGLELIGSIHNQGSTY YNPSLKGRVTISGDTSKNQISLRLSSVTAADTAVYYCARQFGSETYYTGIDPWGQGTLVT VSS |
| 80 | 2A2 $V_H$ | QVQLQESGPGLVKPSETLSLTCTVSGGSISSTSYWAWIRQPPGKGLEWIGTIYYDGYTFY NPSLKSRVTISGDTSKRQYFLRLSSVTAADTAVYYCARHDSGQQLINNWFDPWGQGTVV TVSS |
| 81 | 6G7, 8D10 $V_H$ | QVQLQESGPGLVKSSETLSLTCTVSGDSISSDSYWGWIRQPPGKGLEWLATIYYDGTTFY NPSLRSRLIISGDASKKQFSLRLSSVTAADTAIYYCARHESGQQLVNNWFDPWGQGTVV TVSS |
| 82 | 7H9 $V_H$ | QVQLVQSGAEVKKPGASVKVSCKASGDTSTIHSVHWVRQAPGQGLEWMGTIISSGTTT TYAQSFQDRVSMTIDRSTSTGYMELSSLRFEDTAVYYCTTDGDSWGQGTLVTVSS |
| 83 | 3F12 $V_H$ | QVQLQQSGPGLVKTSETLSLTCTVSGGSVSDYYWSWIRQPPGKGLEWIGYIHSSGSTDY NPSLKSRLTISGDAAKKQFSLNLSSVTAADTALYYCARAQGGSRRTLDYWGQGTLVTVSS |
| 84 | 1D10 $V_H$ | QVQLVESGPGLVKPSETLSLTCTVSVDSTSSDYWSWIRQSPGRGLEWIGYISDSGSTDYN PSLKSRVTISGDRSTKQFSLKLTSVTAADTAVYYCARATVTTYSFDYWGQGALVTVSS |
| 85 | 3G8 $V_H$ | QVQLQQSGPGLVKPSETLSLTCTVSGGSISSTSYWAWIRQPPGKGLEWIGTIYYDGYTFY NPSLKSRVTISGDTSKRQYFLRLSSVTAADTAVYYCARHDSGQQLINNWFDPWGQGTVV TVSS |

TABLE 5-continued

Exemplary anti-Psl antibody V<sub>H</sub> and V<sub>L</sub> sequences.

| SEQ ID NO | Description | Sequence |
|---|---|---|
| 86 | 4D1 V<sub>H</sub> | QVQLQQSGPGLVKPSETLSLTCTVSGYSISSGYYWSWVRQPPGKGLEWIGSIHHSGSTY YNPSLQSRVTISGDTSKKEFSLQLSSVTAADTAVYYCARAEYYYESSGPLFDYWGQGTL VTVSS |
| 87 | 8H5 V<sub>H</sub> | QVQLQESGPGLVKPSETLSLTCTVSDGSVSSGSYYWSWIRQPPGKGLEWIGFIHNNGYT NYNPSLKSRVTISGDTSKKQFSLKVTSVTAADTAVYYCARGETYESSGYYDYWGQGTL VTVSS |
| 88 | 4C1 V<sub>H</sub> | EVQLLESGPGLMKPSETLSLTCSVSGDSISSSDYYWGWIRQPPGKGLEWIASINYAGSTY YNPSLKSRVTISGDTSKKQLYLKLTSVTAADTARYYCTRQNTARGISTDFWGLGTLVTVSS |
| 89 | 9C2 V<sub>H</sub> | EVQLVESGPGLVKPSETLSLTCTVSGDSIRSSSSYWGWIRQPPGKGLEWIGSIYDDGTTFY NPSFKSRVTISGDRSQMQFSLKMTSVTAADTAVYYCARTPYGDYASYFFDYWGQGTLVT VSS |
| 90 | P25 V<sub>H</sub> | EVQLVQSGAEVKNPGASVKVSCKASGHAFAGTYVHWVRQAPGQGFEWIGWIDRNRGG TNYAQKFQGRVTMTRDTSISTVYMELSSLRSDDTAVYYCASDPGLGQGTLVTVSS |
| 91 | P59 V<sub>L</sub> | DIVMTQTPLSLPVTPGEPASISCRSSQSLLHSNGYNYLDWYLQKPGQSPQLLIYLGSNRA SGVPDRFSGSGSGTDFTLKISRVEAEDVGVYYCMQALQTPYTFGQGTKLEIK |
| 92 | 2A2 V<sub>L</sub> | EIVLTQSPSSLSASVGDRVTITCRASQSIGYYLNWYQQKPGEAPKLLIYAASSLQSGVPSR FSGSGSGTDFTLTISSLQPEDFATYYCQQSYTIPYTFGQGTKLEIK |
| 93 | 6G7 V<sub>L</sub> | ETTLTQSPATLSVSPGERATLSCRASQSVSSNLAWYQQKPGQAPRLLIYGASTRATGIPAR FSGSGSGTEFTLTISRLEPEDFAVYYCQQSGDSLVTFGQGTRLEIK |
| 94 | 7H9 V<sub>L</sub> | DIQLTQSPSSVSASVGDRVTIACRASQGISSWLAWYQQKPGKAPKLLIYHASTLESGVPS RFSGSGSGTDFTLTISSLQPEDFATYYCLQANSLPHTFGQGTKLEIK |
| 95 | 3F12 V<sub>L</sub> | EIVMTQSPSTLSASVGDRVAITCRASQTISSYLNWYQLKPGKAPKLLIYAASSLQSGVPSR FSGSGSGTDFTLTISSLQPEDFATYYCQQSYSTPYTFGQGTKVDIK |
| 96 | 1D10 V<sub>L</sub> | DIQLTQSPSSVSASVGDTVTITCRASQGINRWLAWYQQKPGKAPNLLIYATSTLQSGVPS RFSGRGSGTDFTLTISSLQPEDSATYYCQQGYTLPPTLGQGTRLEIK |
| 97 | 3G8 V<sub>L</sub> | DIVMTQTPSSLSASVGDRVTITCRASQGISSYLAWYQQKPGKVPKLLIYAASRLQSGVPS RFSGSGSGTDFTLTIDSLQPEDFATYFCQQSFSVPITFGQGTRLEIK |
| 99 | 4D1 V<sub>L</sub> | DIQMTQSPSSLSASVGDRVTITCQASQDISNSLNWYQQRPGKAPKLLIYDASNLETGVPS RFSGSGSGTEFTLTISSLQPEDFATYYCQQSYTAPYTFGQGTKLEIK |
| 100 | 8D10 V<sub>L</sub> | DIVMTQTPSSLSASVGDRVTITCRASQSISSYLNWYQQKPGKAPELLIYTASNLQTGVPA RFSGSGSGTVFTLTISSLQPEDFATYYCQQSYDSPLTFGGGTKVDIK |
| 101 | 8H5 V<sub>L</sub> | VIRMTQSPSSLSASLGDRVTITCRASQSIGRYLNWYQHKAGKAPKLLIYAASSLQSGVPS RFSGSGSGTDFTLTISSLQPEDFATYYCQQANSLPFTFGQGTRLEIK |
| 102 | 4C1 V<sub>L</sub> | EIVLTQSPGTLSLSPGERATLSCRASQSVSSSYLAWYQQKPGQAPRLLIFGASSRATGIPD RFSGSGSGTDFILTISRLEPEDFAVYYCQHYDNSLTFGGGTKLEIK |
| 103 | 9C2 V<sub>L</sub> | DIVMTQTPLSLSVTPGQPASISCKSSQSLLHSDGKTYLYWYLQKPGQSPPQLLIYEVSNRFS EVPDRFSGSGSGTDFTLKISRVEAEDVGVYYCMQSLQLPLTFGGGTKLEIK |
| 104 | P25 V<sub>L</sub> | EIVLTQSPLSLSVTPGEPASISCRSSQSLLHSNGNNYLDWYLQKPGQSPQLLIYMGSNRAS GVSDRFNGSGSGRDFTLKISRVEAEDVGVYYCMQGLQTPLTFGGGTKLEIK |

TABLE 6

Exemplary anti-Psl antibody variants V<sub>H</sub> and V<sub>L</sub> sequences.

| Antibody variants | V<sub>H</sub> SEQ ID NO | V<sub>L</sub> SEQ ID NO | Antibody variants | V<sub>H</sub> SEQ ID NO | V<sub>L</sub> SEQ ID NO |
|---|---|---|---|---|---|
| 7H9-m01 | 105 | 94 | 7H9-m14 | 82 | 119 |
| 7H9-m02 | 106 | 94 | 7H9-m15 | 82 | 120 |
| 7H9-m03 | 107 | 94 | 7H9-m16 | 82 | 121 |
| 7H9-m04 | 108 | 94 | 7H9-m17 | 82 | 122 |
| 7H9-m05 | 109 | 94 | 7H9-m18 | 82 | 123 |
| 7H9-m06 | 82 | 111 | 7H9-m19 | 82 | 124 |
| 7H9-m07 | 82 | 112 | 7H9-m20 | 82 | 125 |

TABLE 6-continued

Exemplary anti-Psl antibody variants V<sub>H</sub> and V<sub>L</sub> sequences.

| Antibody variants | V<sub>H</sub> SEQ ID NO | V<sub>L</sub> SEQ ID NO | Antibody variants | V<sub>H</sub> SEQ ID NO | V<sub>L</sub> SEQ ID NO |
|---|---|---|---|---|---|
| 7H9-m08 | 82 | 113 | 7H9-m21 | 82 | 126 |
| 7H9-m09 | 82 | 114 | 7H9-m22 | 82 | 127 |
| 7H9-m10 | 82 | 115 | 7H9-m23 | 107 | 113 |
| 7H9-m11 | 82 | 116 | 7H9-m24 | 107 | 123 |
| 7H9-m12 | 82 | 117 | 7H9-m25 | 107 | 116 |
| 7H9-m13 | 82 | 118 | 7H9-m26 | 110 | 94 |
| P59-m01 | 128 | 91 | P59-m17 | 151 | 144 |

TABLE 6-continued

Exemplary anti-Psl antibody variants $V_H$ and $V_L$ sequences.

| Antibody variants | $V_H$ SEQ ID NO | $V_L$ SEQ ID NO | Antibody variants | $V_H$ SEQ ID NO | $V_L$ SEQ ID NO |
|---|---|---|---|---|---|
| P59-m02 | 129 | 91 | P59-m18 | 151 | 145 |
| P59-m03 | 130 | 91 | P59-m19 | 151 | 146 |
| P59-m04 | 131 | 91 | P59-m20 | 151 | 147 |
| P59-m05 | 132 | 91 | P59-m21 | 132 | 143 |
| P59-m06 | 133 | 91 | P59-m22 | 151 | 148 |
| P59-m07 | 134 | 91 | P59-m23 | 149 | 91 |
| P59-m08 | 135 | 91 | P59-m24 | 150 | 91 |
| P59-m09 | 136 | 91 | P59-m25 | 151 | 91 |
| P59-m10 | 137 | 91 | P59-m26 | 152 | 143 |
| P59-m11 | 138 | 91 | P59-m27 | 153 | 143 |
| P59-m12 | 139 | 91 | P59-m28 | 149 | 143 |
| P59-m13 | 151 | 140 | P59-m29 | 154 | 91 |
| P59-m14 | 151 | 141 | P59-m30 | 155 | 91 |
| P59-m15 | 151 | 142 | P59-m31 | 156 | 143 |
| P59-m16 | 151 | 143 | P59-m32 | 157 | 143 |
| | | | P59-m33 | 151 | 98 |
| 3F12-m01 | 159 | 95 | | | |

TABLE 7

Exemplary sequences.

| SEQ ID NO | Description | Sequence |
|---|---|---|
| 160 | IgG1 heavy chain constant region | ASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCDKTHTCPPCPA PELLGGPSVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 161 | IgG4 heavy chain constant region | ASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPSCPAPEF LGGPSVFLFPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTISKAKGQPRE PQVYTLPPSQEEMTKNQVSLTCLVKGFYPSDIAVEWESNGQPENNYKTTPPVLDSD GSFFLYSRLTVDKSRWQEGNVFSCSVMHEALHNHYTQKSLSLSLGK |
| 162 | Light chain constant region | RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |

Binding Affinity

Binding affinity can be indicated by Kd, Koff, Kon, or Ka. The term "Koff", as used herein, is intended to refer to the off-rate constant for dissociation of an antibody from the antibody/antigen complex, as determined from a kinetic selection set up. The term "Kon", as used herein, is intended to refer to the on-rate constant for association of an antibody to the antigen to form the antibody/antigen complex. The term dissociation constant "Kd", as used herein, refers to the dissociation constant of a particular antibody-antigen interaction, and describes the concentration of antigen required to occupy one half of all of the antibody-binding domains present in a solution of antibody molecules at equilibrium, and is equal to Koff/Kon. The measurement of Kd presupposes that all binding agents are in solution. In the case where the antibody is tethered to a cell wall, e.g., in a yeast expression system, the corresponding equilibrium rate constant is expressed as EC50, which gives a good approximation of Kd. The affinity constant, Ka, is the inverse of the dissociation constant, Kd.

The dissociation constant (Kd) is used as an indicator showing affinity of antibody moieties to antigens. For example, easy analysis is possible by the Scatchard method using antibodies marked with a variety of marker agents, as well as by using Biacore (made by Amersham Biosciences), analysis of biomolecular interactions by surface plasmon resonance, according to the user's manual and attached kit. The Kd value that can be derived using these methods is expressed in units of M. An antibody that specifically binds to a target may have a Kd of, for example, $\leq 10^{-7}$ M, $\leq 10^{-8}$ M, $\leq 10^{-9}$ M, $\leq 10^{-10}$ M, $\leq 10^{-11}$ M, $\leq 10^{-12}$ M, or $\leq 10^{-13}$ M.

Binding specificity of the antibody can be determined experimentally by methods known in the art. Such methods comprise, but are not limited to, Western blots, ELISA-, RIA-, ECL-, IRMA-, EIA-, BIAcore-tests and peptide scans.

In some embodiments, the anti-Psl antibody specifically binds to a target Psl with a Kd of about $10^{-7}$ M to about $10^{-13}$ M (such as about $10^{-7}$ M to about $10^{-13}$ M, about $10^{-8}$ M to about $10^{-13}$ M, about $10^{-9}$ M to about $10^{-13}$ M, or about $10^{-10}$ M to about $10^{-12}$ M). Thus in some embodiments, the Kd of the binding between the anti-Psl antibody and Psl, is about $10^{-7}$ M to about $10^{-13}$ M, about $1\times10^{-7}$ M to about $5\times10^{-13}$ M, about $10^{-7}$ M to about $10^{-12}$ M, about $10^{-7}$ M to about $10^{-1}$ M, about $10^{-7}$ M to about $10^{-10}$ M, about $10^{-7}$ M to about $10^{-9}$ M, about $10^{-8}$ M to about $10^{-13}$ M, about $1\times10^{-8}$ M to about $5\times10^{-13}$ M, about $10^{-8}$ M to about $10^{-12}$ M, about $10^{-8}$ M to about $10^{-11}$ M, about $10^{-8}$ M to about $10^{-10}$ M, about $10^{-8}$ M to about $10^{-9}$ M, about $5\times10^{-9}$ M to about $1\times10^{-13}$ M, about $5\times10^{-9}$ M to about $1\times10^{-12}$ M, about $5\times10^{-9}$ M to about $1\times10^{-1}$ M, about $5\times10^{-9}$ M to about $1\times10^{-10}$ M, about $10^{-9}$ M to about $10^{-13}$ M, about $10^{-9}$ M to about $10^{-12}$ M, about $10^{-9}$ M to about $10^{-11}$ M, about $10^{-9}$ M to about $10^{-10}$ M, about $5\times10^{-10}$ M to about $1\times10^{-13}$ M, about $5\times10^{-10}$ M to about $1\times10^{-12}$ M, about $5\times10^{-10}$ M to about $1\times10^{-11}$ M, about $10^{-10}$ M to about $10^{-13}$ M, about $1\times10^{-10}$ M to about $5\times10^{-13}$ M, about $1\times10^{-10}$ M to about $1\times10^{-12}$ M, about $1\times10^{-10}$ M to about $5\times10^{-12}$ M, about $1\times10^{-10}$ M to about $1\times10^{-11}$ M, about $10^{11}$ M to about $10^{13}$ M, about $1\times10^{11}$ M to about $5\times10^{-13}$ M, about $10^{-11}$ M to about $10^{-12}$ M, or about $10^{-12}$ M to about $10^{-13}$ M. In some embodiments, the Kd of the binding between the anti-Psl antibody and a Psl is about $10^{-7}$ M to about $10^{-13}$ M.

In some embodiments, the Kd of the binding between the anti-Psl antibody and a non-target is higher than the Kd of the binding between the anti-Psl antibody and the target, and is herein referred to in some embodiments as the binding affinity of the anti-Psl antibody to the target (e.g., Psl) is higher than that to a non-target. In some embodiments, the non-target is an antigen that is not Psl. In some embodiments, the Kd of the binding between the anti-Psl antibody (against Psl) and a non-Psl target can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the Kd of the binding between the anti-Psl antibody and a target Psl.

Nucleic Acids

Nucleic acid molecules encoding the anti-Psl antibodies are also contemplated. In some embodiments, there is provided a nucleic acid (or a set of nucleic acids) encoding a full-length anti-Psl antibody, including any of the full-length anti-Psl antibodies described herein. In some embodiments, the nucleic acid (or a set of nucleic acids) encoding the anti-Psl antibody described herein may further comprises a nucleic acid sequence encoding a peptide tag (such as protein purification tag, e.g., His-tag, HA tag).

Also contemplated here are isolated host cells comprising an anti-Psl antibody, an isolated nucleic acid encoding the polypeptide components of the anti-Psl antibody, or a vector comprising a nucleic acid encoding the polypeptide components of the anti-Psl antibody described herein.

The present application also includes variants to these nucleic acid sequences. For example, the variants include nucleotide sequences that hybridize to the nucleic acid sequences encoding the anti-Psl antibodies of the present application under at least moderately stringent hybridization conditions.

The present application also provides vectors in which a nucleic acid of the present application is inserted.

In brief summary, the expression of an anti-Psl antibody (e.g., full-length anti-Psl antibody) by a natural or synthetic nucleic acid encoding the anti-Psl antibody can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present application may also be used for nucleic acid immunization and gene therapy, using standard gene delivery protocols. Methods for gene delivery are known in the art. See, e.g., U.S. Pat. Nos. 5,399,346; 5,580,859; 5,589,466, incorporated by reference herein in their entireties. In some embodiments, the application provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green and Sambrook (2013, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the application should not be limited to the use of constitutive promoters. Inducible promoters are also contemplated as part of the application. The use of an inducible promoter provides a molecular switch capable of turning on expression of the polynucleotide sequence to which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the anti-Psl antibody is inducible. In some embodiments, a nucleic acid sequence encoding the anti-Psl antibody is operably linked to an inducible promoter, including any inducible promoter described herein.

Inducible Promoters

The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262: 1019-1024) and ionizing radiation-regulated elements (e.g., see Manome, Y. et al. (1993) Biochemistry 32: 10607-10613; Datta, R. et al. (1992) Proc. Natl. Acad. Sci. USA 89: 1014-10153). Further exemplary inducible promoter systems for use in in vitro or in vivo mammalian systems are reviewed in Gingrich et al. (1998) Annual Rev. Neurosci 21:377-405. In some embodiments, the inducible promoter system for use to express the anti-Psl antibody is the Tet system. In some embodiments, the inducible promoter system for use to express the anti-Psl antibody is the lac repressor system from E. coli.

An exemplary inducible promoter system for use in the present application is the Tet system. Such systems are based on the Tet system described by Gossen et al. (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12a-hexahydro-tetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetracycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from E. coli (See Brown et al., Cell 49:603-612 (1987)). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding a full-length anti-Psl antibody according to any of the full-length anti-Psl antibodies described herein. In some embodiments, the nucleic acid comprises one or more nucleic acid sequences encoding the heavy and light chains of the full-length anti-Psl antibody. In some embodiments, each of the one or more nucleic acid sequences is contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Green and Sambrook (2013, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present application, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the application.

Preparation of Anti-Psl Antibodies

In some embodiments, the anti-Psl antibody is a monoclonal antibody or derived from a monoclonal antibody. In some embodiments, the anti-Psl antibody comprises $V_H$ and $V_L$ domains, or variants thereof, from the monoclonal antibody. In some embodiments, the anti-Psl antibody further comprises CH1 and CL domains, or variants thereof, from the monoclonal antibody. Monoclonal antibodies can be prepared, e.g., using known methods in the art, including hybridoma methods, yeast display, phage display methods, or using recombinant DNA methods. Additionally, exemplary yeast display and phage display methods are described herein and in the Examples below.

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxy-lapatite chromatography, gel electrophoresis, dialysis, or affinity chromatography.

In some embodiments, according to any of the anti-Psl antibodies described herein, the anti-Psl antibody comprises sequences from a clone selected from an antibody library (such as a phage library presenting scFv or Fab fragments). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phages typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The anti-Psl antibodies can be prepared using phage display to screen libraries for anti-Psl antibody moieties specific to the target Psl. The library can be a human scFv phage display library having a diversity of at least $1 \times 10^9$ (such as at least about any of $1 \times 10^9$, $2.5 \times 10^9$, $5 \times 10^9$, $7.5 \times 10^9$, $1 \times 10^{10}$, $2.5 \times 10^{10}$, $5 \times 10^{10}$, $7.5 \times 10^{10}$, or $1 \times^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target Psl with high affinity can be selected by iterative binding of phage to the target Psl, which is bound to a solid support (such as, for example, beads for solution panning or mammalian cells for cell panning), followed by removal of non-bound phage and by elution of specifically bound phage. The bound phage clones are then eluted and used to infect an appropriate host cell, such as *E. coli* XL1-Blue, for expression and purification. The panning can be performed for multiple (such as about any of 2, 3, 4, 5, 6 or more) rounds with solution panning, cell panning, or a combination of both, to enrich for phage clones binding specifically to the target Psl. Enriched phage clones can be tested for specific binding to the target Psl by any methods known in the art, including for example ELISA and FACS.

An alternative method for screening antibody libraries is to display the protein on the surface of yeast cells. Wittrup et al. (U.S. Pat. Nos. 6,699,658 and 6,696,25 1) have developed a method for a yeast cell display library. In this yeast display system, a component involves the yeast agglutinin protein (Aga1), which is anchored to the yeast cell wall. Another component involves a second subunit of the agglutinin protein Aga2, which can display on the surface yeast cells through disulfide bonds to Aga1 protein. The protein Aga1 is expressed from a yeast chromosome after the Aga1 gene integration. A library of single chain variable fragments (scFv) is fused genetically to Aga2 sequence in the yeast display plasmid, which, after transformation, is maintained in yeast episomally with a nutritional marker. Both Aga1 and Aga2 proteins were expressed under the control of the galactose-inducible promoter.

Human antibody V gene repertoire ($V_H$ and $V_K$ fragments) are obtained by PCR method using a pool of degenerate primers (Sblattero, D. & Bradbury, A. Immunotechnology 3, 271-278 1998). The PCR templates are from the commercially available RNAs or cDNAs, including PBMC, spleen, lymph nodes, bone marrow and tonsils. Separate VH and VK PCR libraries were combined, then assembled together in the scFv format by overlap extension PCR (Sheets, M. D. et al. Proc. Natl. Acad. Sci. USA 95, 6157-6162 1998.). To construct the yeast scFv display library, the resultant scFv PCR products are cloned into the yeast display plasmid in the yeasts by homologous recombination. (Chao, G, et al, Nat Protoc. 2006; 1(2):755-68. Miller K D, et al. Current Protocols in Cytometry 4.7.1-4.7.30, 2008).

The anti-Psl antibodies can be discovered using mammalian cell display systems in which antibody moieties are displayed on the cell surface and those specific to the target Psl are isolated by the antigen-guided screening method, as described in U.S. Pat. No. 7,732,195B2. A Chinese hamster ovary (CHO) cell library representing a large set of human IgG antibody genes can be established and used to discover the clones expressing high-affinity antibody genes. Another display system has been developed to enable simultaneous high-level cell surface display and secretion of the same protein through alternate splicing, where the displayed protein phenotype remains linked to genotype, allowing soluble secreted antibody to be simultaneously characterized in biophysical and cell-based functional assays. This approach overcomes many limitations of previous mammalian cell display, enabling direct selection and maturation of antibodies in the form of full-length, glycosylated IgGs (Peter M. Bowers, et al, Methods 2014,65:44-56). Transient expression systems are suitable for a single round of antigen selection before recovery of the antibody genes and therefore most useful for the selection of antibodies from smaller libraries. Stable episomal vectors offer an attractive alternative. Episomal vectors can be transfected at high efficiency and stably maintained at low copy number, permitting multiple rounds of panning and the resolution of more complex antibody libraries.

The IgG library is based on germline sequence V-gene segments joined to rearranged (D)J regions isolated from a panel of human donors. RNA collected from 2000 human blood samples was reverse-transcribed into cDNA, and the $V_H$ and $V_K$ fragments were amplified using $V_{H^-}$ and $V_{K^-}$ specific primers and purified by gel extraction. IgG libraries were generated by sub-cloning the $V_H$ and $V_K$ fragments into the display vectors containing IgG1 or K constant regions respectively and then electroporating into or transducing 293T cells. To generate the scFv antibody display library, scFvs were generated by linking $V_H$ and $V_K$, and then sub-cloned into the display vector, which were then electroporated into or transduce 293T cells. As we known, the IgG library is based on germline sequence V-gene segments joined to rearranged (D)J regions isolated from a panel of donors, the donor can be a mouse, rat, rabbit, or monkey.

Monoclonal antibodies can also be made by recombinant DNA methods, such as those described in U.S. Pat. No. 4,816,567. DNA encoding the monoclonal antibodies of the application can be readily isolated and sequenced using conventional procedures (e.g., by using oligonucleotide probes that are capable of binding specifically to genes encoding the heavy and light chains of murine antibodies). Hybridoma cells as described above or Psl-specific phage clones of the application can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the application, or can be substituted for the variable domains of one antigen-combining site of an antibody of the application to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region to prevent heavy-chain crosslinking. Alternatively, the relevant cysteine residues are substituted with another amino acid residue or are deleted to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism.

Human and Humanized Antibodies

The anti-Psl antibodies (e.g., full-length anti-Psl antibodies) can be humanized antibodies or human antibodies. Humanized forms of non-human (e.g., murine) antibody moieties are chimeric immunoglobulins, immunoglobulin chains, or fragments thereof (such as Fv, Fab, Fab', F(ab')$_2$, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody nor in the imported CDR or framework sequences. In general, the humanized antibody can comprise substantially at least one, and typically two, variable domains, in which all or substantially all of the CDR regions correspond to those of a non-human immunoglobulin, and all or substantially all of the FR regions are those of a human immunoglobulin consensus sequence.

Generally, a humanized antibody has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature,* 321: 522-525 (1986); Riechmann et al., *Nature,* 332: 323-327 (1988); Verhoeyen et al., *Science,* 239: 1534-1536 (1988)), by substituting rodent CDRs or CDR sequences for the corresponding sequences of a human antibody. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA,* 90:2551 (1993); Jakobovits et al., *Nature,* 362:255-258 (1993); Bruggemann et al., *Year in Immunol.,* 7:33 (1993); U.S. Pat. Nos. 5,545, 806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661,016, and Marks et al., *Bio Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); *Neuberger, Nature Biotechnology,* 14: 826 (1996); Lonberg and Huszar, *Intern. Rev. Immunol.,* 13: 65-93 (1995).

Human antibodies may also be generated by in vitro activated B cells (see U.S. Pat. Nos. 5,567,610 and 5,229, 275) or by using various techniques known in the art, including phage display libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy,* Alan R. Liss, p. 77 (1985) and Boerner et al., *J. Immunol.,* 147(1): 86-95 (1991).

Anti-Psl Antibody Variants

In some embodiments, amino acid sequences of the anti-Psl antibody variants (e.g., full-length anti-Psl antibody) provided herein are contemplated. For example, it may be desirable to improve the binding affinity and/or other biological properties of the antibody. Amino acid sequence of an antibody variant may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, anti-Psl antibody variants having one or more amino acid substitutions are provided. Sites of interest for substitutional mutagenesis include the HVRs and FRs. Amino acid substitutions may be introduced into an antibody of interest and the products screened for a desired activity, e.g., improved bioactivity, retained/improved antigen binding, decreased immunogenicity, or improved opsonophagocytic killing (OPK) of pathogens, such as *P. aeruginosa.*

Conservative Substitutions are Shown in Table 8 Below.

TABLE 8

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:
   a. hydrophobic: Norleucine, Met, Ala, Val, Leu, Ile;
   b. neutral hydrophilic: Cys, Ser, Thr, Asn, Gln;
   c. acidic: Asp, Glu;
   d. basic: His, Lys, Arg;
   e. residues that influence chain orientation: Gly, Pro;
   f. aromatic: Trp, Tyr, Phe.

Non-conservative substitutions will entail exchanging a member of one of these classes for another class.

An exemplary substitutional variant is an affinity matured antibody, which may be conveniently generated, e.g., using phage display-based affinity maturation techniques. Briefly, one or more CDR residues are mutated and the variant antibody moieties displayed on phage and screened for a particular biological activity (e.g., bioactivity based on RBC lysis inhibition assay or binding affinity). Alterations (e.g., substitutions) may be made in HVRs, e.g., to improve bioactivity based on RBC lysis inhibition assay or antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ and $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant $V_H$ and $V_L$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., ala or glu) to determine whether the interaction of the antibody with antigen is affected. Further substitutions may be introduced at the amino acid locations to demonstrate functional sensitivity to the initial substitutions. Alternatively, or additionally, a crystal structure of an antigen-antibody complex can be determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Fc Region Variants

In some embodiments, one or more amino acid modifications may be introduced into the Fc region of an antibody (e.g., a full-length anti-Psl antibody or anti-Psl Fc fusion protein) provided herein, thereby generating an Fc region variant. In some embodiments, the Fc region variant has enhanced ADCC effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J Biol. Chem.* 9(2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., an infected cell), whose membrane-surface antigens have been bound by specific antibodies (e.g., an anti-Psl antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis.

In some embodiments, the application contemplates an anti-Psl antibody variant (such as a full-length anti-Psl antibody variant) comprising an Fc region that possesses one or more effector functions, for example, ADCC or CDC. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, alterations are made in the Fc region that result in altered (i.e., either improved or diminished) opsonization, e.g. such as described in Moore et al., *MAbs.* 2(2): 181-189 (2010).

In some embodiments, there is provided an anti-Psl antibody (such as a full-length anti-Psl antibody) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-Psl antibodies (such as full-length anti-Psl antibodies) comprising any of the Fc variants described herein, or combinations thereof, are contemplated.

Glycosylation Variants

In some embodiments, an anti-Psl antibody (such as a full-length anti-Psl antibody) provided herein is altered to increase or decrease the extent to which the anti-Psl antibody is glycosylated. Addition or deletion of glycosylation sites to an anti-Psl antibody may be conveniently accomplished by altering the amino acid sequence of the anti-Psl antibody or polypeptide portion thereof such that one or more glycosylation sites are created or removed.

Where the anti-Psl antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al, *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-Psl antibody of the application may be made in order to create anti-Psl antibody variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., J. Biochem. 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-Psl antibody (such as a full-length anti-Psl antibody) variants are provided comprising an Fc region wherein a carbohydrate structure attached to the Fc region has reduced fucose or lacks fucose, which may improve ADCC function. Specifically, anti-Psl antibodies are contemplated herein that have reduced fucose relative to the amount of fucose on the same anti-Psl antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-Psl antibody is one wherein less than about 50%, 40%, 30%, 20%, 10%, or 5% of the N-linked glycans thereon comprise fucose. For example, the amount of fucose in such an anti-Psl antibody may be from 1% to 80%, from 1% to 65%, from 5% to 65% or from 20% to 40%. In some embodiments, the anti-Psl antibody is one wherein none of the N-linked glycans thereon comprise fucose, i.e., wherein the anti-Psl antibody is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. Arch. *Biochem. Biophys.* 249:533-545 (1986); US Pat Appl No US 2003/0157108 A1, Presta, L; and WO 2004/056312 A1, Adams et al., especially at Example 11), and knockout cell lines, such asα-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Anti-Psl antibody (such as a full-length anti-Psl antibody) variants are further provided with bisected oligosaccharides, e.g., in which a biantennary oligosaccharide attached to the Fc region of the anti-Psl antibody is bisected by GlcNAc. Such anti-Psl antibody (such as a full-length anti-Psl antibody) variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering,* 93(5): 851-861 (2006). Anti-Psl antibody (such as full-length anti-Psl antibody) variants with at least one galactose residue in the oligosaccharide attached to the Fc region are also provided. Such anti-Psl antibody variants may have improved CDC function. Such antibody variants are described, e.g., in WO 1997/30087 (Patel et al.); WO 1998/58964 (Raju, S.); and WO 1999/22764 (Raju, S.).

In some embodiments, the anti-Psl antibody (such as a full-length anti-Psl antibody) variants comprising an Fc region are capable of binding to an FcγRIII. In some embodiments, the anti-Psl antibody (such as a full-length anti-Psl antibody) variants comprising an Fc region have ADCC activity in the presence of human effector cells (e.g., T cell) or have increased ADCC activity in the presence of human effector cells compared to the otherwise same anti-Psl antibody (such as a full-length anti-Psl antibody) comprising a human wild-type Fc region.

Cysteine Engineered Variants

In some embodiments, it may be desirable to create cysteine engineered anti-Psl antibodies (such as a full-length anti-Psl antibody) in which one or more amino acid residues are substituted with cysteine residues. In some embodiments, the substituted residues occur at accessible sites of the anti-Psl antibody. By substituting those residues with cysteine, reactive thiol groups are thereby positioned at accessible sites of the anti-Psl antibody and may be used to conjugate the anti-Psl antibody to other moieties, such as drug moieties or linker-drug moieties, to create an anti-Psl immunoconjugate, as described further herein. Cysteine engineered anti-Psl antibodies (e.g., full-length anti-Psl antibodies) may be generated as described, e.g., in U.S. Pat. No. 7,521,541.

Derivatives

In some embodiments, an anti-Psl antibody (such as a full-length anti-Psl antibody) provided herein may be further modified to contain additional non-proteinaceous moieties that are known in the art and readily available. The moieties suitable for derivatization of the anti-Psl antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-Psl antibody may vary, and if more than one polymer are attached, they can be the same or different molecules. In general, the number and/or type of polymers used for derivatization can be determined based on considerations including, but not limited to, the particular properties or functions of anti-Psl antibody to be improved, whether the anti-Psl antibody derivative will be used in a therapy under defined conditions, etc.

In some embodiments, conjugates of an anti-Psl antibody (such as a full-length anti-Psl antibody) and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the anti-Psl antibody-nonproteinaceous moiety are killed.

Pharmaceutical Compositions

Also provided herein are compositions (such as pharmaceutical compositions, also referred to herein as formulations) comprising any of the anti-Psl antibodies (such as a full-length anti-Psl antibody), nucleic acids encoding the antibodies, vectors comprising the nucleic acids encoding the antibodies, or host cells comprising the nucleic acids or vectors described herein. In some embodiments, there is provided a pharmaceutical composition comprising any one of the anti-Psl antibodies described herein and a pharmaceutically acceptable carrier.

Suitable formulations of the anti-Psl antibodies are obtained by mixing an anti-Psl antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-Psl antibodies of this application into cells.

The formulation herein may also contain one or more active compounds in addition to the anti-Psl antibody (such as a full-length anti-Psl antibody) as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent in addition to the anti-Psl antibody. Such molecules are suitably present in combination in amounts that are effective for the purpose intended. The effective amount of such other agents depends on the amount of anti-Psl antibody present in the formulation, the type of disease or disorder or treatment, and other factors discussed above. These are generally used in the same dosages and with administration routes as described herein or about from 1 to 99% of the heretofore employed dosages.

The anti-Psl antibodies (e.g., full-length anti-Psl antibodies) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Sustained-release preparations may be prepared.

Sustained-release preparations of the anti-Psl antibodies (e.g., full-length anti-Psl antibodies) can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D (–)-3-hydroxybutyric acid. While polymers such as ethylene-vinyl acetate and lactic acid-glycolic acid enable release of molecules for over 100 days, certain hydro gels release proteins for shorter time periods. When encapsulated antibody remain in the body for a long time, they can denature or aggregate as a result of exposure to moisture at 37° C., resulting in a loss of biological activity and possible changes in immunogenicity. Rational strategies can be devised for stabilization of anti-Psl antibodies depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-Psl antibody (such as a full-length anti-Psl antibody) is formulated in a buffer comprising a citrate, NaCl, acetate, succinate, glycine, polysorbate 80 (Tween 80), or any combination of the foregoing. In some embodiments, the anti-Psl antibody is formulated in a buffer comprising about 100 mM to about 150 mM glycine. In some embodiments, the anti-Psl antibody is formulated in a buffer comprising about 50 mM to about 100 mM NaCl. In some embodiments, the anti-Psl antibody is formulated in a buffer comprising about 10 mM to about 50 mM acetate. In some embodiments, the anti-Psl antibody is formulated in a buffer comprising about 10 mM to about 50 mM succinate. In some embodiments, the anti-Psl antibody is formulated in a buffer comprising about 0.005% to about 0.02% polysorbate 80. In some embodiments, the anti-Psl antibody is formulated in a buffer having a pH between about 5.1 and 5.6. In some embodiments, the anti-Psl antibody is formulated in a buffer comprising 10 mM citrate, 100 mM NaCl, 100 mM glycine, and 0.01% polysorbate 80, wherein the formulation is at pH 5.5.

The formulations to be used for in vivo administration must be sterile. This is readily accomplished by, e.g., filtration through sterile filtration membranes.

Methods of Treatment or Prevention Using Anti-Psl Antibodies

In certain aspects, there is provided a method of treating a *Pseudomonas* infection in an individual comprising administering to the individual an effective amount of a composition comprising any of the anti-Psl antibodies described herein. In some embodiments, the method of treating a *Pseudomonas* infection further provides therapeutic or prophylactic effect on diseases and/or conditions associated with *Pseudomonas* infection. In some aspects, there is provided a method of preventing a *Pseudomonas* infection in an individual comprising administering to the individual an effective amount of a composition comprising any of the anti-Psl antibodies described herein. In some embodiments, use of the anti-Psl antibody according to any one of the anti-Psl antibodies described above, or a pharmaceutical composition comprising an anti-Psl antibody according to any one of the pharmaceutical compositions described above in the manufacture of a medicament for treating a disease or condition.

Diseases and/or conditions associated with *Pseudomonas* infection include, but are not limited to fever, chills, fatigues, muscle, and joint pain, swelling of joints, headache, diarrhea, skin rashes, pus in wounds, bacteremia, acute pneumonia, intraperitoneal infection. Further exemplary diseases include, but are not limited to, respiratory tract infections, bacteremia, septic shock, suppurative arthritis, enteritis, skin, and soft tissue infections (such as burn wound infections), urinary tract infections, intestinal infections, ulcerative keratitis, chronic suppurative otitis media, mastoiditis, sinusitis, and endocarditis. In some embodiments, the method of treating or preventing a *Pseudomonas* infection reduces rate of mortality resulting from the *Pseudomonas* infection.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising an HC-CDR1 comprising the amino acid sequence of any one of SEQ ID NOs: 2-3, and 5-12, an HC-CDR2 comprising the amino acid sequence of any one of SEQ ID NOs: 14-15, and 17-23, and an HC-CDR3 comprising the amino acid sequence of any one of SEQ ID NOs: 25-26, and 28-34; and a $V_L$ comprising an LC-CDR1 comprising the amino acid sequence of any one of SEQ ID NOs: 38-39, and 41-49, an LC-CDR2 comprising the amino acid sequence of any one of SEQ ID NOs: 52-53, and 55-61, and an LC-CDR3 comprising the amino acid sequence of any one of SEQ ID NOs: 63-64, 66-68, and 70-75. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising an HC-CDR1 comprising the amino acid sequence of any one of SEQ ID NOs: 2-3, and 5-12, an HC-CDR2 comprising the amino acid sequence of any one of SEQ ID NOs: 14-15, and 17-23, and an HC-CDR3 comprising the amino acid sequence of any one of SEQ ID NOs: 25-26, and 28-34; and a $V_L$ comprising an LC-CDR1 comprising the amino acid sequence of any one of SEQ ID NOs: 38-39, and 41-49, an LC-CDR2 comprising the amino acid sequence of any one of SEQ ID NOs: 52-53, and 55-61, and an LC-CDR3 comprising the amino acid sequence of any one of SEQ ID NOs: 63-64, 66-68, and 70-75. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising an HC-CDR1 comprising the amino acid sequence of any one of SEQ ID NOs: 2-3, and 5-12, an HC-CDR2 comprising the amino acid sequence of any one of SEQ ID NOs: 14-15, and 17-23, and an HC-CDR3 comprising the amino acid sequence of any one of SEQ ID NOs: 25-26, and 28-34; and a $V_L$ comprising an LC-CDR1 comprising the amino acid sequence of any one of SEQ ID NOs: 38-39, and 41-49, an LC-CDR2 comprising the amino acid sequence of any one of SEQ ID NOs: 52-53, and 55-61, and an LC-CDR3 comprising the amino acid sequence of any one of SEQ ID NOs: 63-64, 66-68, and 70-75.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of any one of SEQ ID NOs: 80-81, 83-90, and 159 and a $V_L$ comprising the amino acid sequence of any one of SEQ ID NOs: 92-93, 95-97, and 99-104. In some embodiments, there is provided a method of treating or preventing a *Pseudomonas* infection in an individual comprising administering to the individual an effective amount of a composition comprising an anti-Psl anti-body, wherein the anti-Psl antibody competes with an antibody comprising: a V$_H$ comprising the amino acid sequence of any one of SEQ ID NOs: 80-81, 83-90, and 159 and a V$_L$ comprising the amino acid sequence of any one of SEQ ID NOs: 92-93, 95-97, and 99-104. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a V$_H$ comprising the amino acid sequence of any one of SEQ ID NOs: 80-81, 83-90, and 159 and a V$_L$ comprising the amino acid sequence of any one of SEQ ID NOs: 92-93, 95-97, and 99-104.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a V$_H$ comprising an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25; and a V$_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a V$_H$ comprising an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25; and a V$_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a V$_H$ comprising the amino acid sequence of SEQ ID NO: 80 and a V$_L$ comprising the amino acid sequence of SEQ ID NO: 92. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a V$_H$ comprising the amino acid sequence of SEQ ID NO: 80 and a V$_L$ comprising the amino acid sequence of SEQ ID NO: 92.

In some embodiments, there is provided a method of treating or preventing a *Pseudomonas* infection in an individual comprising administering to the individual an effective amount of a composition comprising an anti-Psl antibody comprising: a V$_H$ comprising an HC-CDR1 comprising the amino acid sequence of SEQ ID NO: 2, an HC-CDR2 comprising the amino acid sequence of SEQ ID NO: 14, and an HC-CDR3 comprising the amino acid sequence of SEQ ID NO: 25, or a variant thereof comprising up to 5 amino acid substitutions; and a V$_L$ comprising an LC-CDR1 comprising the amino acid sequence of SEQ ID NO: 38, an LC-CDR2 comprising the amino acid sequence of SEQ ID NO: 52, and an LC-CDR3 comprising the amino acid sequence of SEQ ID NO: 63, or a variant thereof comprising up to 5 amino acid substitutions. In some embodiments, the anti-Psl antibody comprises a V$_H$ comprising the amino acid sequence of SEQ ID NO: 80, or a variant thereof having at least 90% (for example at least about any of 91%, 92%, 93%, 94%, 95%, 96%, 97%, 98%, or 99%) sequence identity to the amino acid sequence of SEQ ID NO: 80; and a V$_L$ comprising the amino acid sequence of SEQ ID NO: 92, or a variant thereof having at least 90% (for example at least about any of 91%, 92%, 93%, 94%, 95%, 96%, 97%, 98%, or 99%) sequence identity to the amino acid sequence of SEQ ID NO: 92.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a V$_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a V$_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a V$_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a V$_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a V$_H$ comprising the amino acid sequence of SEQ ID NO: 81 and a V$_L$ comprising the amino acid sequence of SEQ ID NO: 93. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a V$_H$ comprising the amino acid sequence of SEQ ID NO: 81 and a V$_L$ comprising the amino acid sequence of SEQ ID NO: 93.

In some embodiments, there is provided a method of treating or preventing a *Pseudomonas* infection in an individual comprising administering to the individual an effective amount of a composition comprising an anti-Psl antibody comprising: a V$_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to 5 amino acid substitutions; and a $V_L$ comprising an LC-CDR1 comprising the amino acid sequence of SEQ ID NO: 39, an LC-CDR2 comprising the amino acid sequence of SEQ ID NO: 53, and an LC-CDR3 comprising the amino acid sequence of SEQ ID NO: 64, or a variant thereof comprising up to 5 amino acid substitutions. In some embodiments, the anti-Psl antibody comprises a $V_H$ comprising the amino acid sequence of SEQ ID NO: 81, or a variant thereof having at least 90% (for example at least about any of 91%, 92%, 93%, 94%, 95%, 96%, 97%, 98%, or 99%) sequence identity to the amino acid sequence of SEQ ID NO: 81, and a $V_L$ comprising the amino acid sequence of SEQ ID NO: 93, or a variant thereof having at least 90% (for example at least about any of 91%, 92%, 93%, 94%, 95%, 96%, 97%, 98%, or 99%) sequence identity to the amino acid sequence of SEQ ID NO: 93.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28; and a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28; and a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 83 and a $V_L$ comprising the amino acid sequence of SEQ ID NO: 95. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 83 and a $V_L$ comprising the amino acid sequence of SEQ ID NO: 95.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 159 and a $V_L$ comprising the amino acid sequence of SEQ ID NO: 95. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 159 and a $V_L$ comprising the amino acid sequence of SEQ ID NO: 95.

In some embodiments, there is provided a method of treating or preventing a *Pseudomonas* infection in an individual comprising administering to the individual an effective amount of a composition comprising an anti-Psl antibody comprising: a $V_H$ comprising an HC-CDR1 comprising the amino acid sequence of SEQ ID NO: 5, an HC-CDR2 comprising the amino acid sequence of SEQ ID NO: 17, and an HC-CDR3 comprising the amino acid sequence of SEQ ID NO: 28, or a variant thereof comprising up to 5 amino acid substitutions; and a $V_L$ comprising an LC-CDR1 comprising the amino acid sequence of SEQ ID NO: 41, an LC-CDR2 comprising the amino acid sequence of SEQ ID NO: 52, and an LC-CDR3 comprising the amino acid sequence of SEQ ID NO: 66, or a variant thereof comprising up to 5 amino acid substitutions. In some embodiments, the anti-Psl antibody comprises a $V_H$ comprising the amino acid sequence of SEQ ID NO: 83, or a variant thereof having at least 90% (for example at least about any of 91%, 92%, 93%, 94%, 95%, 96%, 97%, 98%, or 99%) sequence identity to the amino acid sequence of SEQ ID NO: 83; and a $V_L$ comprising the amino acid sequence of SEQ ID NO: 95, or a variant thereof having at least 90% (for example at least about any of 91%, 92%, 93%, 94%, 95%, 96%, 97%, 98%, or 99%) sequence identity to the amino acid sequence of SEQ ID NO: 95. In some embodiments, the anti-Psl antibody comprises a $V_H$ comprising the amino acid sequence of SEQ ID NO: 159, or a variant thereof having at least 90% (for example at least about any of 91%, 92%, 93%, 94%, 95%, 96%, 97%, 98%, or 99%) sequence identity to the amino acid sequence of SEQ ID NO: 159; and a $V_L$ comprising the amino acid sequence of SEQ ID NO: 95, or a variant thereof having at least 90% (for example at least about any of 91%, 92%, 93%, 94%, 95%, 96%, 97%, 98%, or 99%) sequence identity to the amino acid sequence of SEQ ID NO: 95.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29; and a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29; and a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 84 and a $V_L$ comprising the amino acid sequence of SEQ ID NO: 96. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 84 and a $V_L$ comprising the amino acid sequence of SEQ ID NO: 96.

In some embodiments, there is provided a method of treating or preventing a *Pseudomonas* infection in an individual comprising administering to the individual an effective amount of a composition comprising an anti-Psl antibody comprising: a $V_H$ comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 29, or a variant thereof comprising up to 5 amino acid substitutions; and a $V_L$ comprising an LC-CDR1 comprising the amino acid sequence of SEQ ID NO: 42, an LC-CDR2 comprising the amino acid sequence of SEQ ID NO: 55, and an LC-CDR3 comprising the amino acid sequence of SEQ ID NO: 67, or a variant thereof comprising up to 5 amino acid substitutions. In some embodiments, the anti-Psl antibody comprises a $V_H$ comprising the amino acid sequence of SEQ ID NO: 84, or a variant thereof having at least 90% (for example at least about any of 91%, 92%, 93%, 94%, 95%, 96%, 97%, 98%, or 99%) sequence identity to the amino acid sequence of SEQ ID NO: 84; and a $V_L$ comprising the amino acid sequence of SEQ ID NO: 96, or a variant thereof having at least 90% (for example at least about any of 91%, 92%, 93%, 94%, 95%, 96%, 97%, 98%, or 99%) sequence identity to the amino acid sequence of SEQ ID NO: 96.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25; and a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68. In some embodiments, there is provided a method of treating or preventing a *Pseudomonas* infection in an individual comprising administering to the individual an effective amount of a compo-sition comprising an anti-Psl antibody, wherein the anti-Psl antibody binds to the same epitope as an antibody comprising: a $V_H$ comprising an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25; and a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 85 and a $V_L$ comprising the amino acid sequence of SEQ ID NO: 97. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 85 and a $V_L$ comprising the amino acid sequence of SEQ ID NO: 97.

In some embodiments, there is provided a method of treating or preventing a *Pseudomonas* infection in an individual comprising administering to the individual an effective amount of a composition comprising an anti-Psl antibody comprising: a $V_H$ comprising an HC-CDR1 comprising the amino acid sequence of SEQ ID NO: 7, an HC-CDR2 comprising the amino acid sequence of SEQ ID NO: 14, and an HC-CDR3 comprising the amino acid sequence of SEQ ID NO: 25, or a variant thereof comprising up to 5 amino acid substitutions; and a $V_L$ comprising an LC-CDR1 comprising the amino acid sequence of SEQ ID NO: 43, an LC-CDR2 comprising the amino acid sequence of SEQ ID NO: 56, and an LC-CDR3 comprising the amino acid sequence of SEQ ID NO: 68, or a variant thereof comprising up to 5 amino acid substitutions. In some embodiments, the anti-Psl antibody comprises a $V_H$ comprising the amino acid sequence of SEQ ID NO: 85, or a variant thereof having at least 90% (for example at least about any of 91%, 92%, 93%, 94%, 95%, 96%, 97%, 98%, or 99%) sequence identity to the amino acid sequence of SEQ ID NO: 85; and a $V_L$ comprising the amino acid sequence of SEQ ID NO: 97, or a variant thereof having at least 90% (for example at least about any of 91%, 92%, 93%, 94%, 95%, 96%, 97%, 98%, or 99%) sequence identity to the amino acid sequence of SEQ ID NO: 97.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70. In some embodiments, there is provided a method of treating or preventing a *Pseudomonas* infection in an individual comprising administering to the individual an effective amount of a compo-sition comprising an anti-Psl antibody, wherein the anti-Psl antibody binds to the same epitope as an antibody compris-ing: a $V_H$ comprising an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70.

In some embodiments, there is provided a method of treating or preventing a *Pseudomonas* infection in an indi-vidual comprising administering to the individual an effec-tive amount of a composition comprising an anti-Psl anti-body, wherein the anti-Psl antibody competes with an antibody comprising: a $V_H$ comprising the amino acid sequence of SEQ ID NO: 86 and a $V_L$ comprising the amino acid sequence of SEQ ID NO: 99. In some embodiments, there is provided a method of treating or preventing a *Pseudomonas* infection in an individual comprising admin-istering to the individual an effective amount of a compo-sition comprising an anti-Psl antibody, wherein the anti-Psl antibody binds to the same epitope as an antibody compris-ing: a $V_H$ comprising the amino acid sequence of SEQ ID NO: 86 and a $V_L$ comprising the amino acid sequence of SEQ ID NO: 99.

In some embodiments, there is provided a method of treating or preventing a *Pseudomonas* infection in an indi-vidual comprising administering to the individual an effec-tive amount of a composition comprising an anti-Psl anti-body comprising: a $V_H$ comprising an HC-CDR1 comprising the amino acid sequence of SEQ ID NO: 8, an HC-CDR2 comprising the amino acid sequence of SEQ ID NO: 19, and an HC-CDR3 comprising the amino acid sequence of SEQ ID NO: 30, or a variant thereof comprising up to 5 amino acid substitutions; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 70, or a variant thereof comprising up to 5 amino acid substitutions. In some embodiments, the anti-Psl antibody comprises a $V_H$ com-prising the amino acid sequence of SEQ ID NO: 86, or a variant thereof having at least 90% (for example at least about any of 91%, 92%, 93%, 94%, 95%, 96%, 97%, 98%, or 99%) sequence identity to the amino acid sequence of SEQ ID NO: 86; and a $V_L$ comprising the amino acid sequence of SEQ ID NO: 99, or a variant thereof having at least 90% (for example at least about any of 91%, 92%, 93%, 94%, 95%, 96%, 97%, 98%, or 99%) sequence iden-tity to the amino acid sequence of SEQ ID NO: 99.

In some embodiments, there is provided a method of treating or preventing a *Pseudomonas* infection in an indi-vidual comprising administering to the individual an effec-tive amount of a composition comprising an anti-Psl anti-body, wherein the anti-Psl antibody competes with an antibody comprising: a $V_H$ comprising an HC-CDR1 com-prising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71. In some embodiments, there is provided a method of treating or preventing a *Pseudomonas* infection in an individual comprising admin-istering to the individual an effective amount of a compo-sition comprising an anti-Psl antibody, wherein the anti-Psl antibody binds to the same epitope as an antibody compris-ing: a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26; and a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71.

In some embodiments, there is provided a method of treating or preventing a *Pseudomonas* infection in an indi-vidual comprising administering to the individual an effec-tive amount of a composition comprising an anti-Psl anti-body, wherein the anti-Psl antibody competes with an antibody comprising: a $V_H$ comprising the amino acid sequence of SEQ ID NO: 81 and a $V_L$ comprising the amino acid sequence of SEQ ID NO: 100. In some embodiments, there is provided a method of treating or preventing a *Pseudomonas* infection in an individual comprising admin-istering to the individual an effective amount of a compo-sition comprising an anti-Psl antibody, wherein the anti-Psl antibody binds to the same epitope as an antibody compris-ing: a $V_H$ comprising the amino acid sequence of SEQ ID NO: 81 and a $V_L$ comprising the amino acid sequence of SEQ ID NO: 100.

In some embodiments, there is provided a method of treating or preventing a *Pseudomonas* infection in an indi-vidual comprising administering to the individual an effec-tive amount of a composition comprising an anti-Psl anti-body comprising: a $V_H$ comprising an HC-CDR1 comprising the amino acid sequence of SEQ ID NO: 3, an HC-CDR2 comprising the amino acid sequence of SEQ ID NO: 15, and an HC-CDR3 comprising the amino acid sequence of SEQ ID NO: 26, or a variant thereof comprising up to 5 amino acid substitutions; and a $V_L$ comprising an LC-CDR1 comprising the amino acid sequence of SEQ ID NO: 45, an LC-CDR2 comprising the amino acid sequence of SEQ ID NO: 58, and an LC-CDR3 comprising the amino acid sequence of SEQ ID NO: 71, or a variant thereof comprising up to 5 amino acid substitutions. In some embodiments, the anti-Psl antibody comprises a $V_H$ com-prising the amino acid sequence of SEQ ID NO: 81, or a variant thereof having at least 90% (for example at least about any of 91%, 92%, 93%, 94%, 95%, 96%, 97%, 98%, or 99%) sequence identity to the amino acid sequence of SEQ ID NO: 81; and a $V_L$ comprising the amino acid sequence of SEQ ID NO: 100, or a variant thereof having at least 90% (for example at least about any of 91%, 92%, 93%, 94%, 95%, 96%, 97%, 98%, or 99%) sequence iden-tity to the amino acid sequence of SEQ ID NO: 100.

In some embodiments, there is provided a method of treating or preventing a *Pseudomonas* infection in an indi-vidual comprising administering to the individual an effec-tive amount of a composition comprising an anti-Psl anti-body, wherein the anti-Psl antibody competes with an antibody comprising: a $V_H$ comprising an HC-CDR1 com-prising the amino acid sequence of SEQ ID NO: 9, an HC-CDR2 comprising the amino acid sequence of SEQ ID NO: 20, and an HC-CDR3 comprising the amino acid sequence of SEQ ID NO: 31; and a $V_L$ comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a V_H comprising an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31; and a V_L comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a V_H comprising the amino acid sequence of SEQ ID NO: 87 and a V_L comprising the amino acid sequence of SEQ ID NO: 101. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a V_H comprising the amino acid sequence of SEQ ID NO: 87 and a V_L comprising the amino acid sequence of SEQ ID NO: 101.

In some embodiments, there is provided a method of treating or preventing a *Pseudomonas* infection in an individual comprising administering to the individual an effective amount of a composition comprising an anti-Psl antibody comprising: a V_H comprising an HC-CDR1 comprising the amino acid sequence of SEQ ID NO: 9, an HC-CDR2 comprising the amino acid sequence of SEQ ID NO: 20, and an HC-CDR3 comprising the amino acid sequence of SEQ ID NO: 31, or a variant thereof comprising up to 5 amino acid substitutions; and a V_L comprising an LC-CDR1 comprising the amino acid sequence of SEQ ID NO: 46, an LC-CDR2 comprising the amino acid sequence of SEQ ID NO: 52, and an LC-CDR3 comprising the amino acid sequence of SEQ ID NO: 72, or a variant thereof comprising up to 5 amino acid substitutions. In some embodiments, the anti-Psl antibody comprises a V_H comprising the amino acid sequence of SEQ ID NO: 87, or a variant thereof having at least 90% (for example at least about any of 91%, 92%, 93%, 94%, 95%, 96%, 97%, 98%, or 99%) sequence identity to the amino acid sequence of SEQ ID NO: 87; and a V_L comprising the amino acid sequence of SEQ ID NO: 101, or a variant thereof having at least 90% (for example at least about any of 91%, 92%, 93%, 94%, 95%, 96%, 97%, 98%, or 99%) sequence identity to the amino acid sequence of SEQ ID NO: 101.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a V_H comprising an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32; and a V_L comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a V_H comprising an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32; and a V_L comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a V_H comprising the amino acid sequence of SEQ ID NO: 88 and a V_L comprising the amino acid sequence of SEQ ID NO: 102. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a V_H comprising the amino acid sequence of SEQ ID NO: 88 and a V_L comprising the amino acid sequence of SEQ ID NO: 102.

In some embodiments, there is provided a method of treating or preventing a *Pseudomonas* infection in an individual comprising administering to the individual an effective amount of a composition comprising an anti-Psl antibody comprising: a V_H comprising an HC-CDR1 comprising the amino acid sequence of SEQ ID NO: 10, an HC-CDR2 comprising the amino acid sequence of SEQ ID NO: 21, and an HC-CDR3 comprising the amino acid sequence of SEQ ID NO: 32, or a variant thereof comprising up to 5 amino acid substitutions; and a V_L comprising an LC-CDR1 comprising the amino acid sequence of SEQ ID NO: 47, an LC-CDR2 comprising the amino acid sequence of SEQ ID NO: 59, and an LC-CDR3 comprising the amino acid sequence of SEQ ID NO: 73, or a variant thereof comprising up to 5 amino acid substitutions. In some embodiments, the anti-Psl antibody comprises a V_H comprising the amino acid sequence of SEQ ID NO: 88, or a variant thereof having at least 90% (for example at least about any of 91%, 92%, 93%, 94%, 95%, 96%, 97%, 98%, or 99%) sequence identity to the amino acid sequence of SEQ ID NO: 88; and a V_L comprising the amino acid sequence of SEQ ID NO: 102, or a variant thereof having at least 90% (for example at least about any of 91%, 92%, 93%, 94%, 95%, 96%, 97%, 98%, or 99%) sequence identity to the amino acid sequence of SEQ ID NO: 102.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a V_H comprising an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33; and a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33; and a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 89 and a $V_L$ comprising the amino acid sequence of SEQ ID NO: 103. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 89 and a $V_L$ comprising the amino acid sequence of SEQ ID NO: 103.

In some embodiments, there is provided a method of treating or preventing a *Pseudomonas* infection in an individual comprising administering to the individual an effective amount of a composition comprising an anti-Psl antibody comprising: a $V_H$ comprising an HC-CDR1 comprising the amino acid sequence of SEQ ID NO: 11, an HC-CDR2 comprising the amino acid sequence of SEQ ID NO: 22, and an HC-CDR3 comprising the amino acid sequence of SEQ ID NO: 33, or a variant thereof comprising up to 5 amino acid substitutions; and a $V_L$ comprising an LC-CDR1 comprising the amino acid sequence of SEQ ID NO: 48, an LC-CDR2 comprising the amino acid sequence of SEQ ID NO: 60, and an LC-CDR3 comprising the amino acid sequence of SEQ ID NO: 74, or a variant thereof comprising up to 5 amino acid substitutions. In some embodiments, the anti-Psl antibody comprises a $V_H$ comprising the amino acid sequence of SEQ ID NO: 89, or a variant thereof having at least 90% (for example at least about any of 91%, 92%, 93%, 94%, 95%, 96%, 97%, 98%, or 99%) sequence identity to the amino acid sequence of SEQ ID NO: 89; and a $V_L$ comprising the amino acid sequence of SEQ ID NO: 103, or a variant thereof having at least 90% (for example at least about any of 91%, 92%, 93%, 94%, 95%, 96%, 97%, 98%, or 99%) sequence identity to the amino acid sequence of SEQ ID NO: 103.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34; and a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34; and a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75.

In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 90 and a $V_L$ comprising the amino acid sequence of SEQ ID NO: 104. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 90 and a $V_L$ comprising the amino acid sequence of SEQ ID NO: 104.

In some embodiments, there is provided a method of treating or preventing a *Pseudomonas* infection in an individual comprising administering to the individual an effective amount of a composition comprising an anti-Psl antibody comprising: a $V_H$ comprising an HC-CDR1 comprising the amino acid sequence of SEQ ID NO: 12, an HC-CDR2 comprising the amino acid sequence of SEQ ID NO: 23, and an HC-CDR3 comprising the amino acid sequence of SEQ ID NO: 34, or a variant thereof comprising up to 5 amino acid substitutions; and a $V_L$ comprising an LC-CDR1 comprising the amino acid sequence of SEQ ID NO: 49, an LC-CDR2 comprising the amino acid sequence of SEQ ID NO: 61, and an LC-CDR3 comprising the amino acid sequence of SEQ ID NO: 75, or a variant thereof comprising up to 5 amino acid substitutions. In some embodiments, the anti-Psl antibody provided herein comprises a $V_H$ comprising the amino acid sequence of SEQ ID NO: 90, or a variant thereof having at least 90% (for example at least about any of 91%, 92%, 93%, 94%, 95%, 96%, 97%, 98%, or 99%) sequence identity to the amino acid sequence of SEQ ID NO: 90; and a $V_L$ comprising the amino acid sequence of SEQ ID NO: 104, or a variant thereof having at least 90% (for example at least about any of 91%, 92%, 93%, 94%, 95%, 96%, 97%, 98%, or 99%) sequence identity to the amino acid sequence of SEQ ID NO: 104.

In some embodiments, there is provided a method of treating or preventing a *Pseudomonas* infection in an individual comprising administering to the individual an effective amount of a composition comprising an anti-Psl antibody comprising: a heavy chain variable domain ($V_H$) comprising a heavy chain complementarity determining region (HC-CDR) 1 comprising IHSVH (SEQ ID NO: 4), or a variant thereof comprising up to about 3 amino acid substitutions; an HC-CDR2 comprising TIISSGTTT-TYAQSFQD (SEQ ID NO: 16), or a variant thereof comprising up to about 3 amino acid substitutions; and an HC-CDR3 comprising $X_1X_2X_3X_4$ (SEQ ID NO: 189), or a variant thereof comprising up to about 3 amino acid substitutions, wherein $X_1$ is D, Y or N, $X_2$ is G, or A, $X_3$ is D, or T, $X_4$ is S, A, or T; and a light chain variable domain ($V_L$) comprising a light chain complementarity determining region (LC-CDR) 1 comprising RASQGISSWLA (SEQ ID NO: 40), or a variant thereof comprising up to about 3 amino acid substitutions; an LC-CDR2 comprising HASTLES (SEQ ID NO: 54), or a variant thereof comprising up to about 3 amino acid substitutions; and an LC-CDR3 comprising LQAX$_1$SLPHT (SEQ ID NO: 158), or a variant thereof comprising up to about 3 amino acid substitutions, wherein $X_1$ is N, D, Y, F, P, G, K, H, A, C, E, Q, R, S, T, V, W or L.

In some embodiments, there is provided a method of treating or preventing a *Pseudomonas* infection in an individual comprising administering to the individual an effective amount of a composition comprising an anti-Psl antibody, wherein the anti-Psl antibody comprises: a heavy chain variable domain ($V_H$) comprising a heavy chain complementarity determining region (HC-CDR) 1 comprising IHSVH (SEQ ID NO: 4); an HC-CDR2 comprising TIISSGTTTTYAQSFQD (SEQ ID NO: 16); and an HC-CDR3 comprising an amino acid sequence selected from a group of SEQ ID NO: 27, SEQ ID NO: 35, and SEQ ID NOs: 165-169; and a light chain variable domain ($V_L$) comprising a light chain complementarity determining region (LC-CDR) 1 comprising RASQGISSWLA (SEQ ID NO: 40); an LC-CDR2 comprising HASTLES (SEQ ID NO: 54); and an LC-CDR3 comprising an amino acid sequence selected from a group of SEQ ID NO: 65, SEQ ID NOs: 76-78, and SEQ ID NOs: 199-212.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of SEQ ID NO: 82 and a $V_L$ comprising the amino acid sequence of SEQ ID NO: 94. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 82 and a $V_L$ comprising the amino acid sequence of SEQ ID NO: 94. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 82 and a $V_L$ comprising the amino acid sequence of SEQ ID NO: 94.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of any one of SEQ ID NOs: 105-110 and a $V_L$ comprising the amino acid sequence of SEQ ID NO: 94. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of any one of SEQ ID NOs: 105-110 and a $V_L$ comprising the amino acid sequence of SEQ ID NO: 94. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of any one of SEQ ID NOs: 105-110 and a $V_L$ comprising the amino acid sequence of SEQ ID NO: 94.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of SEQ ID NO: 82 and a $V_L$ comprising the amino acid sequence of any one of SEQ ID NOs: 111-127. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 82 and a $V_L$ comprising the amino acid sequence of any one of SEQ ID NOs: 111-127. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 82 and a $V_L$ comprising the amino acid sequence of any one of SEQ ID NOs: 111-127.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of SEQ ID NO: 107 and a $V_L$ comprising the amino acid sequence of SEQ ID NO: 113. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 107 and a $V_L$ comprising the amino acid sequence of SEQ ID NO: 113. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 107 and a $V_L$ comprising the amino acid sequence of SEQ ID NO: 113.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of SEQ ID NO: 107 and a $V_L$ comprising the amino acid sequence of SEQ ID NO: 123. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 107 and a $V_L$ comprising the amino acid sequence of SEQ ID NO: 123. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 107 and a $V_L$ comprising the amino acid sequence of SEQ ID NO: 123.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of SEQ ID NO: 107 and a $V_L$ comprising the amino acid sequence of SEQ ID NO: 116. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 107 and a $V_L$ comprising the amino acid sequence of SEQ ID NO: 116. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 107 and a $V_L$ comprising the amino acid sequence of SEQ ID NO: 116.

In some embodiments, there is provided a method of treating or preventing a *Pseudomonas* infection in an individual comprising administering to the individual an effective amount of a composition comprising an anti-Psl antibody comprising: a heavy chain variable domain $(V_H)$ comprising a heavy chain complementarity determining region (HC-CDR) 1 comprising SSGDYWG (SEQ ID NO: 1), or a variant thereof comprising up to about 3 amino acid substitutions; an HC-CDR2 comprising SINX₁GSTYYNPSLKG (SEQ ID NO: 213), or a variant thereof comprising up to about 3 amino acid substitutions, wherein $X_1$ is S, K, or Q; and an HC-CDR3 comprising QFGSETYYX₁GIX₂P (SEQ ID NO: 190), or a variant thereof comprising up to about 3 amino acid substitutions, wherein $X_1$ is N, S, V, T, or P, $X_2$ is D, Y, C, H, S, R, A, E, G, K, W, V, or Q; and a light chain variable domain $(V_L)$ comprising a light chain complementarity determining region (LC-CDR) 1 comprising RSSQSLLHSX₁GYNYLD (SEQ ID NO: 184), or a variant thereof comprising up to about 3 amino acid substitutions, wherein $X_1$ is N, A, V, F, R, G, H, Q, W, or P; an LC-CDR2 comprising LGSNRAS (SEQ ID NO: 51), or a variant thereof comprising up to about 3 amino acid substitutions; and an LC-CDR3 comprising MQALQTPX₁T (SEQ ID NO: 214), wherein $X_1$ is R or Y, or a variant thereof comprising up to about 3 amino acid substitutions.

In some embodiments, there is provided a method of treating or preventing a *Pseudomonas* infection in an individual comprising administering to the individual an effective amount of a composition comprising an anti-Psl antibody, wherein the anti-Psl antibody comprises a heavy chain variable domain $(V_H)$ comprising a heavy chain complementarity determining region (HC-CDR) 1 comprising SSGDYWG (SEQ ID NO: 1); an HC-CDR2 comprising an amino acid sequence selected from the group of SEQ ID NO:13, and SEQ ID NOs:163-164; and an HC-CDR3 comprising an amino acid sequence selected from the group of SEQ ID NO: 24, SEQ ID NO: 36, SEQ ID NOs: 170-183, and SEQ ID NOs: 185-188; and a light chain variable domain $(V_L)$ comprising a light chain complementarity determining region (LC-CDR) 1 comprising an amino acid sequence selected from the group of SEQ ID NO: 37, SEQ ID NO: 50, and SEQ ID NOs: 191-198; an LC-CDR2 comprising LGSNRAS (SEQ ID NO: 51); and an LC-CDR3 comprising an amino acid sequence selected from the group of SEQ ID NO: 62 and SEQ ID NO: 69.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of SEQ ID NO: 79 and a $V_L$ comprising the amino acid sequence of SEQ ID NO: 91. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 79 and a $V_L$ comprising the amino acid sequence of SEQ ID NO: 91. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 79 and a $V_L$ comprising the amino acid sequence of SEQ ID NO: 91.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of any one of SEQ ID NOs: 128-139, 149-151, and 154-155 and a $V_L$ comprising the amino acid sequence of SEQ ID NO: 91. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of any one of SEQ ID NOs: 128-139, 149-151, and 154-155 and a $V_L$ comprising the amino acid sequence of SEQ ID NO: 91. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of any one of SEQ ID NOs: 128-139, 149-151, and 154-155 and a $V_L$ comprising the amino acid sequence of SEQ ID NO: 91.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of SEQ ID NO: 151 and a $V_L$ comprising the amino acid sequence of any one of SEQ ID NOs: 140-148. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 151 and a $V_L$ comprising the amino acid sequence of any one of SEQ ID NOs: 140-148. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 151 and a $V_L$ comprising the amino acid sequence of any one of SEQ ID NOs: 140-148.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of any one of SEQ ID NOs: 132, 149, 152-153, and 156-157 and a $V_L$ comprising the amino acid sequence of SEQ ID NO: 143. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of any one of SEQ ID NOs: 132, 149, 152-153, and 156-157 and a $V_L$ comprising the amino acid sequence of SEQ ID NO: 143. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of any one of SEQ ID NOs: 132, 149, 152-153, and 156-157 and a $V_L$ comprising the amino acid sequence of SEQ ID NO: 143.

In some embodiments, there is provided a method of treating or preventing a *Pseudomonas* infection in an individual comprising administering to the individual an effective amount of a composition comprising an anti-Psl antibody, wherein the anti-Psl antibody comprises a $V_H$ comprising the amino acid sequence of SEQ ID NO: 151 and a $V_L$ comprising the amino acid sequence of SEQ ID NO: 98. In some embodiments, there is provided a method of treating or preventing a *Pseudomonas* infection in an individual comprising administering to the individual an effective amount of a composition comprising an anti-Psl antibody, wherein the anti-Psl antibody competes with an antibody comprising: a $V_H$ comprising the amino acid sequence of SEQ ID NO: 151 and a $V_L$ comprising the amino acid sequence of SEQ ID NO: 98. In some embodiments, there is provided a method of treating or preventing a *Pseudomonas* infection in an individual comprising administering to the individual an effective amount of a composition comprising an anti-Psl antibody, wherein the anti-Psl antibody binds to the same epitope as an antibody comprising: a $V_H$ comprising the amino acid sequence of SEQ ID NO: 151 and a $V_L$ comprising the amino acid sequence of SEQ ID NO: 98.

In some embodiments according to any of the methods of treatment or prevention described herein, the anti-Psl antibody comprises an antibody heavy chain constant region and an antibody light chain constant region. In some embodiments, the anti-Psl antibody comprises an IgG1 heavy chain constant region. In some embodiments, the anti-Psl antibody comprises an IgG2 heavy chain constant region. In some embodiments, the anti-Psl antibody comprises an IgG3 heavy chain constant region. In some embodiments, the anti-Psl antibody comprises an IgG4 heavy chain constant region. In some embodiments, the IgG is a human IgG. In some embodiments, the heavy chain constant region comprises or consists of the amino acid sequence of SEQ ID NO: 160. In some embodiments, the heavy chain constant region comprises or consists of the amino acid sequence of SEQ ID NO: 161. In some embodiments, the anti-Psl comprises a lambda light chain constant region. In some embodiments, the anti-Psl antibody comprises a kappa light chain constant region. In some embodiments, the light chain constant region comprises or consists of the amino acid sequence of SEQ ID NO: 162. In some embodiments, the anti-Psl antibody comprises an antibody heavy chain variable domain and an antibody light chain variable domain.

In some embodiments according to any of the methods of treatment or prevention described herein, the method further provides therapeutic or prophylactic effect on diseases and/or conditions associated with *Pseudomonas* infection. In some embodiments, the method prevents a *Pseudomonas* infection in an individual.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old).

In some embodiments, the individual has one or more risk factors associated with *P. aeruginosa* infection. For example, in some embodiments, the individual has exposed or breached skin mucuous layer. In some embodiments, the individual has one or more burn wounds. In some embodiments, the individual has one or more surgery wounds. In some embodiments, the individual has skin disease. In some embodiments, the individual is inserted with a foreign body, such as, but not limited to a mechanical ventilator or catheter. In some embodiments, the individual is diagnosed with or genetically prone to immunodeficiency diseases, including but not limited to HIV infection, AIDS and/or neutrophil deficiency. In some embodiments, the individual has received one or more forms of chemotherapy. In some embodiments, the individual has received one or more forms of glucocorticoid treatment. In some embodiments, the individual has received one or more forms of chemotherapy. In some embodiments, the individual is diagnosed with or genetically prone to cancer, diabetes, and/or chronic structural lung diseases (such as cystic fibrosis or COPD). In some embodiments, the individual is diagnosed with or genetically prone to flora imbalance in digestive system and/or in other organs. In some embodiments, the individual has one or more risk factors associated with one or more diseases or disorders described herein.

The present application in some embodiments provides a method of delivering an anti-Psl antibody (such as any one of the anti-Psl antibodies described herein, e.g., an isolated anti-Psl antibody) to a cell infected by a pathogen in an individual, the method comprising administering to the individual a composition comprising the anti-PSl antibody.

In some embodiments according to any one of the methods described herein, the method further comprises administering one or more additional therapeutic agents. In some embodiments, at least one of the therapeutic agents is an antibiotic. In some embodiments, the antibiotic is a penicillin, a cephalosporin, a carbapenem, a fluoroquinolone, an aminoglycoside, a monobactam, a polymyxin, an antibiotic combination containing 3-lactamase inhibitor, or any combinations thereof. In some embodiments, the antibiotic is Cefepim, Ceftazidime, Cefpirome, Imipenem, Meropenem, Ticarcillin, Piperacillin, Azlocillin, Carbenicillin, Mezlocillin, Aztreonam, Tobramycin, Gentamicin, Amikacin, Ciprofloxacin, Levofloxacin, Cefoperazon-Sulbactam, Piperacillin-Tazobactam, Fosfomycin, or any combinations thereof. In some embodiments, the antibiotic is one or more of Imipenem, Tobramycin, Ciprofloxacin, Meropenem or Aztreonam. In some embodiments, the antibiotic is one or more of Gentamycin, Ampicillin or Kanamycin.

Many diagnostic methods for infectious agents exhibiting Psl expression and the clinical delineation of those diseases are known in the art. Such methods include, but are not limited to, e.g., immunohistochemistry, PCR, and fluorescent in situ hybridization (FISH).

In some embodiments, the anti-Psl antibodies (e.g., full-length anti-Psl antibodies) and/or compositions of the application are administered in combination with a second, third, or fourth agent (including, e.g., an antibiotic) to treat or prevent diseases or disorders involving Psl-expressing pathogens.

Dosing and Method of Administering the Anti-PSL Antibodies

The dose of the anti-PSL antibody (such as isolated anti-PSL antibody) compositions administered to an individual (such as a human) may vary with the particular composition, the mode of administration, and the type of disease being treated. In some embodiments, the amount of the composition (such as composition comprising isolated anti-PSL antibody) is effective to result in an objective response (such as a partial response or a complete response) in the treatment or prevention of *Pseudomonas* infections. In some embodiments, the amount of the anti-Psl antibody composition is sufficient to result in a complete response in the individual. In some embodiments, the amount of the anti-Psl antibody composition is sufficient to result in a partial response in the individual. In some embodiments, the amount of the anti-Psl antibody composition administered (for example when administered alone) is sufficient to produce an overall response rate of more than about any of 20%, 25%, 30%, 35%, 40%, 45%, 50%5, 55% 60%, 64%, 65%, 70%, 75%, 80%, 85%, or 90% among a population of individuals treated with the anti-PSL antibody composition. Responses of an individual to the treatment or prevention by the methods described herein can be determined, for example, based on detection of Pseudomonas by methods such as by Gram stains or other phenotypic tests.

In some embodiments, the amount of the composition (such as composition comprising isolated anti-Psl antibody) is sufficient to prolong progress-free survival of the individual. In some embodiments, the amount of the composition is sufficient to prolong overall survival of the individual. In some embodiments, the amount of the composition (for example when administered along) is sufficient to produce clinical benefit of more than about any of 50%, 60%, 70%, or 77% among a population of individuals treated with the anti-Psl antibody composition.

In some embodiments, the amount of the composition (such as composition comprising isolated anti-Psl antibody), alone or in combination with a second, third, and/or fourth agent, is an amount sufficient to decrease the number of *Pseudomonas* organ burden by at least about any of 10%, 20%, 30%, 40%, 50%, 60%, 70%, 80%, 90%, 95% or 100% compared to the corresponding organ burden in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the anti-Psl antibody (such as a full-length anti-Psl antibody) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regimen. In some embodiments, the amount of the composition is more than about any of 80%, 90%, 95%, or 98% of the MTD.

In some embodiments, the amount of an anti-Psl antibody (such as a full-length anti-Psl antibody) in the composition is included in a range of about 0.001 μg to about 1000 μg.

In some embodiments, the composition or method further comprises one or more antibiotics. In some embodiments, the amount of an antibiotic (such as Imipenem, Tobramycin, Ciprofloxacin, Meropenem, Aztreonam, Ticarcillin, Piperacillin, Azlocillin, Carbenicillin, Mezlocillin, Gentamycin or Amikacin) in the composition is included in a range of about 0.001 g to about 1000 μg.

In some embodiments of any of the above aspects, the effective amount of anti-Psl antibody (such as a full-length anti-Psl antibody) in the composition is in the range of about 0.1 μg/kg to about 100 mg/kg of total body weight.

In some embodiments of any of the above aspects, the effective amount of antibiotic (such as Imipenem, Tobramycin, Ciprofloxacin, Meropenem, Aztreonam, Ticarcillin, Piperacillin, Azlocillin, Carbenicillin, Mezlocillin, Gentamycin or Amikacin) in the composition is in the range of about 0.1 μg/kg to about 100 mg/kg of total body weight.

The anti-Psl antibody compositions can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, or transdermal. In some embodiments, sustained continuous release formulation of the composition may be used. In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrahepatically. In some embodiments, the composition is administered by hepatic arterial infusion. In some embodiments, the administration is to an injection site distal to a first disease site.

Articles of Manufacture and Kits

In some embodiments of the application, there is provided an article of manufacture containing materials useful for treating or preventing a *Pseudomonas* infection in an individual, or for delivering an anti-Psl antibody (such as a full-length anti-Psl antibody) to a cell attached by a pathogen expressing Psl. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an anti-Psl antibody of the application. The label or package insert indicates that the composition is used for treating the particular condition. The label or package insert will further comprise instructions for administering the anti-Psl antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating bacterial infections. In some embodiments, the package insert indicates that the composition is used for treating *Pseudomonas* infections.

Additionally, the article of manufacture may further comprise a second container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

Kits are also provided that are useful for various purposes, e.g., useful for treating or preventing a *Pseudomonas* infection in an individual, or for delivering an anti-Psl antibody (such as a full-length anti-Psl antibody) to a cell attached by a pathogen expressing Psl, optionally in combination with the articles of manufacture. Kits of the application include one or more containers comprising anti-Psl antibody composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the application are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-Psl antibody (such as a full-length anti-Psl antibody). In some embodiments, the kit comprises a) a composition comprising any one of the anti-Psl antibodies described herein, and b) an effective amount of at least one other agent, wherein the other agent enhances the effect (e.g., treatment effect, detecting effect) of the anti-Psl antibody. In some embodiments, the kit comprises a) a composition comprising any one of the anti-Psl antibodies described herein, and b) instructions for administering the anti-Psl antibody composition to an individual for treating a *Pseudomonas* infection in an individual. In some embodiments, the kit comprises a) a composition comprising any one of the anti-Psl antibodies described herein, b) an effective amount of at least one other agent, wherein the other agent enhances the effect (e.g., treatment effect, detecting effect) of the anti-Psl antibody, and c) instructions for administering the anti-Psl antibody composition and the other agent(s) to an individual for useful for treating a *Pseudomonas* infection in an individual. The anti-Psl antibody and the other agent(s) can be present in separate containers or in a single container. For example, the kit may comprise one distinct composition or two or more compositions wherein one composition comprises an anti-Psl antibody and another composition comprises another agent.

In some embodiments, the kit comprises a nucleic acid (or a set of nucleic acids) encoding an anti-Psl antibody (such as a full-length anti-Psl antibody). In some embodiments, the kit comprises a) a nucleic acid (or a set of nucleic acids) encoding an anti-Psl antibody, and b) a host cell for expressing the nucleic acid (or a set of nucleic acids). In some embodiments, the kit comprises a) a nucleic acid (or a set of nucleic acids) encoding an anti-Psl antibody, and b) instructions for i) expressing the anti-Psl antibody in a host cell, ii) preparing a composition comprising the anti-Psl antibody, and iii) administering the composition comprising the anti-Psl antibody to an individual for treating or preventing a *Pseudomonas* infection in an individual. In some embodiments, the kit comprises a) a nucleic acid (or a set of nucleic acids) encoding an anti-Psl antibody, b) a host cell for expressing the nucleic acid (or a set of nucleic acids), and c) instructions for i) expressing the anti-Psl antibody in the host cell, ii) preparing a composition comprising the anti-Psl antibody, and iii) administering the composition comprising the anti-Psl antibody to an individual for treating or preventing a *Pseudomonas* infection in an individual.

The kits of the application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-Psl antibody compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of an anti-Psl antibody (such as a full-length anti-Psl antibody) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-Psl antibody and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this application. The application will now be described in greater detail by reference to the following non-limiting examples. The following examples further illustrate the application but, of course, should not be construed as in any way limiting its scope.

EXAMPLES

Example 1: Generation of Psl Polysaccharide and Selection of Anti-Psl scFv Antibodies Generation of Psl Polysaccharide The method of generating Psl polysaccharide comprises the following steps: P. aeruginosa PAO1 bacteria (CNCTC PAO1) were inoculated into LBNS (LB culture medium without NaCl), cultured for 18 hours at 37° C. The bacteria were collected and centrifuged, and the supernatant was discarded. After resuspending the bacteria precipitate, the bacteria biofilms were separated from the thallus by shaking or ultrasound. After centrifugation, ethanol was added to the supernatant to precipitate the polysaccharide. After high-speed centrifugation, the precipitate was resuspended, after which DNase I and proteinase K were added for treatment. Subsequently, proteins were extracted and removed using phenol/chloroform, then the Psl polysaccharide was precipitated with ethanol, and dissolved with water.

Generation of Biotinylated Psl Polysaccharide

Biotinylation of the Psl polysaccharide was carried out using EZ-Link™ Alkoxyamine-PEG-Biotin Reagents (Thermo Scientific) according to the manufacturer's protocol. Briefly, polysaccharide was oxidized by sodium periodate. After the reaction, sodium periodate was removed by a dialysis method. Alkoxyamine-biotin was added to oxidized Psl polysaccharide at the mole ratio of 1:9, followed by 2 hours of incubation at room temperature; and finally, the biotinylated Psl polysaccharide was separated from unreacted substances by using a dialysis or desalination method.

Selection of Anti-Psl scFv Antibodies

Generation of yeast scFv antibody display library: RNA collected from 2000 human blood samples was reverse-transcribed into cDNA, and the $V_H$ and $V_K$ fragments were amplified using $V_H$- and $V_K$-specific primers. Upon gel extraction and purification, scFvs were generated by linking $V_H$ and $V_K$ via a linker. The scFvs were cloned into the yeast display plasmid PYD1, which were then electroporated into yeast to generate the yeast scFv antibody display library.

Selection of anti-Psl scFv antibodies: The scFvs which recognized Psl were enriched and selected from the yeast display library after several rounds of panning. Briefly, magnetic-activated cell sorting (MACS) was used to enrich cells expressing anti-Psl scFv antibodies. Biotinylated Psl was mixed with magnetic beads (Dynabeads™ MyOne™ Streptavidin T1) overnight to coat magnetic beads with the biotinylated Psl, according to the manufacturer's protocol. The scFv antibody yeast library was then mixed with the Psl-coated beads for enriching yeasts that display Psl-recognizing antibodies, whereas the non-binders were washed away in washing steps. Subsequently, the yeast samples enriched in the previous MACS panning were subjected to fluorescence-activated cell sorting (FACS). The FACS-guided selection was repeated for 2-3 cycles. The selected yeast library cells were plated on agar, and single colonies were picked and assayed by further FACS analysis. From yeast clones that exhibited positive binding to Psl, each scFv gene was subcloned into a prokaryotic expression vector and fused with a 6-His tag. The His-labeled scFvs were then purified using Ni Sepharose purification according to the manufacturer's protocol. A panel of positive scFv antibodies were obtained at the end of the selection process and subjected to functional testing for the ability to inhibit attachment (ATT) of P. aeruginosa to A549 cell, and to promote opsonophagocytic killing (OPK).

Example 2: Generation of Full-Length Human Anti-Psl Antibodies and Determination of their Biological Activity Generation of Full-Length Anti-Psl Antibodies The most potent scFv antibodies were reformatted as human IgG1 antibody molecules with a human IgG1 heavy chain constant domain, and a human kappa light chain constant domain. $V_L$ and $V_H$ were amplified from the pro-karyotic expression vector and introduced into eukaryotic expression vectors pTT5-L (containing kappa constant domain) and pTT5-H1 (containing IgG1 heavy chain constant domain), respectively. Plasmids expressing the light or heavy chains were extracted and used to co-transfect 293F cells. After the cells were cultured at 37° C., 8% $CO_2$ and 120 rpm for 5 days, the antibodies in the culture media were purified using Protein A affinity chromatography.

Briefly, Protein A column was first equilibrated with a PBS buffer containing 50 mM PBS and 0.15M NaCl (pH7.2), at a flow rate of 150 cm/h and with a volume that is six times the volume of the column. The supernatant of the culture media (pH was adjusted to 7.2) was passed through the column at the flow rate of 150 cm/h. Upon further equilibration, the column was washed using 50 mM sodium citrate (pH3.5) and the elution containing anti-Psl antibodies was collected. The full-length IgG1 antibodies were subjected to in vivo and in vitro biological activity evaluation. Assays for in vitro functional screening included opsonophagocytic killing (OPK) assay and cell attachment assay using the epithelial cell line A549. The antibodies used in the in-vivo experiment were subjected to endotoxin removal to reduce the influence of endotoxin on the experimental results.

Anti-Psl Antibodies Inhibit Attachment of P. aeruginosa to A549 Human Pulmonary Epithelial Cells This experiment shows that anti-Psl antibodies inhibit P. aeruginosa from binding to epithelial cells. The luminescent P. aeruginosa PAO1(O5)-LUX bacteria was constructed by a PTN 7 transposon system as described in (Choi K H, et al. mini-Tn7 insertion in bacteria with single attTn7 sites: example Pseudomonas aeruginosa[J]. Nature Protocols, 2006, 1(1):153-161). The blocking activity of candidate antibodies was determined by detecting the luminescence signal value of the luminescent P. aeruginosa. Anti-Psl antibodies were added to a confluent monolayer of A549 cells (an adenocarcinoma human alveolar basal epithelial cell line) seeded in white 96-well plates (Nunclon Delta) in DMEM plus 10% fetal bovine serum. Log-phase luminescent P. aeruginosa PAO1(O5)-LUX was then added into the cells at a multiplicity of infection (MOI) of 10 and incubated for 1 h at 37° C. and 5% $CO_2$. The A549 cells were then washed to remove the un-attached bacteria, followed by the addition of 2YT culture medium. Bacteria were quantified following a brief incubation at 37° C. Cam-003 and Wapr-001 were used as the reference antibodies. The intensity value of luminescence for the entire plate was read in the self-luminous module. The value obtained from the assay with reference antibody Cam-003 of saturated dose (300

μg/ml) was designated as 100% inhibition, and that from the assay without adding the anti-Psl antibody was designated as 0% inhibition, with which the relative inhibition effect of the anti-Psl was calculated. IC50 values for the inhibition of the antibodies were calculated using the 4-parameter method of GraphPad Prism version6.

Figure 1B:
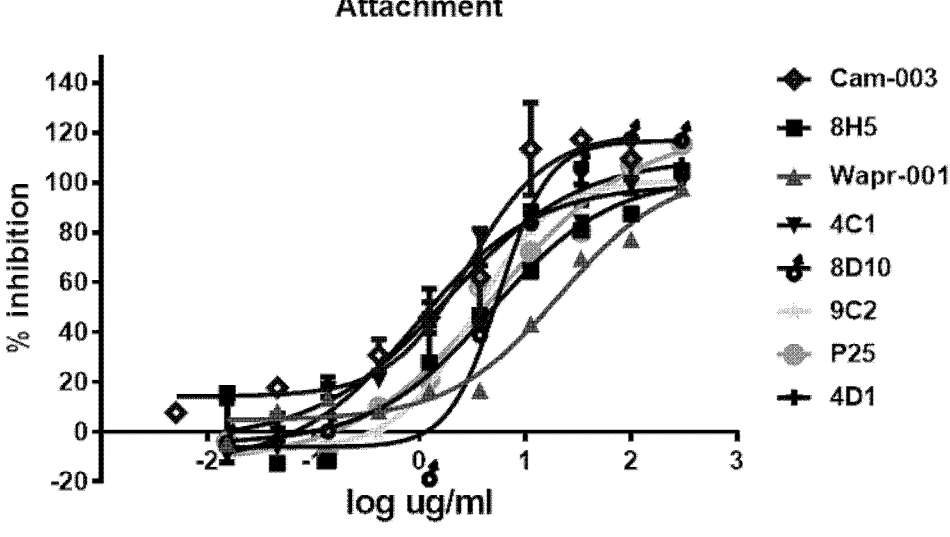

As shown in FIGS. 1A-1B and Table 9, all the anti-Psl antibodies exhibited significantly better efficacies in blocking the attachment of *P. aeruginosa* to A549 cells as compared to the reference antibody Wapr-001, and exhibited better or comparable efficacies in blocking the attachment of *P. aeruginosa* to A549 cells as compared to the reference antibody Cam-003.

TABLE 9

Efficacy of the anti-Psl antibodies in blocking attachment of *P. aeruginosa* strains to A549 cells

| Antibody | ATT(IC50 μg/ml) | Antibody | ATT(IC50 μg/ml) |
|---|---|---|---|
| Cam-003 | 3.39 | 3G8 | 2.81 |
| Wapr-001 | 21.83 | 4D1 | 1.80 |
| P59 | 2.29 | 8D10 | 3.67 |
| 2A2 | 2.21 | 8H5 | 4.17 |
| 6G7 | 2.43 | 4C1 | 1.03 |
| 7H9 | 1.20 | 9C2 | 3.04 |
| 3F12 | 2.12 | P25 | 4.05 |
| 1D10 | 1.02 | | |

Evaluation of Anti-Psl Antibodies in Promoting OPK of *P. aeruginosa*

This experiment shows the ani-Psl antibodies that mediate opsonophagocytic killing (OPK) of *P. aeruginosa*. The luminescent *P. aeruginosa* PAO1(O5)-LUX bacteria were constructed by a PTN 7 transposon system. The activity of anti-Psl antibodies is determined by detecting the luminescence signal value of the luminescent *P. aeruginosa*. OPK assays were performed as described in (DiGiandomenico, A., et al., *Infect Immun* 72, 7012-7021(2004)). Briefly, the assays were performed in 96-well plates, with baby rabbit serum (CREATIVE DIAGNOSTICS, Cat #DAG136) using as a complement source, differentiated HL-60 cells, log-phase luminescent *P. aeruginosa* PAO1(O5)-LUX, and serially diluted anti-Psl antibodies. Specifically, HL-60 cells were differentiated into human polymorphonuclear leukocytes (PMNs) using the methods known in the art (Fleck R A, et al. Use of HL-60 Cell Line To Measure Opsonic Capacity of Pneumococcal Antibodies[J]. Clinical & Diagnostic Laboratory Immunology, 2005, 12(1):19). The 96-well plates were coated with the PMNs, 2 ml of the baby rabbit serum was diluted with the same volume of culture medium, and was added to the plate with 25 μL/well. The anti-Psl antibody was subjected to a 3-fold ratio dilution, and was added to the plates with 10 μL/well. Luminescent *P. aeruginosa* PAO1(O5)-LUX in log-phase were then added to the well at a multiplicity of infection (MOI) of 0.1. Bacteria were quantified following a 4 hours incubation at 37° C. and 5% $CO_2$, via reading luminescence intensity value. Cam-003 and Wapr-001 were used as the reference antibodies. The value obtained from the assay with the reference antibody Cam-003 of saturated dose (300 μg/ml) was designated as 100% OPK, and the value from the assay without adding the anti-Psl antibody was designated as 0% OPK, with which the percentage of the OPK of the anti-Psl antibodies was calculated. EC50 values for the antibodies were calculated using the 4-parameter method of GraphPad Prism version 6.

Figure 1C:
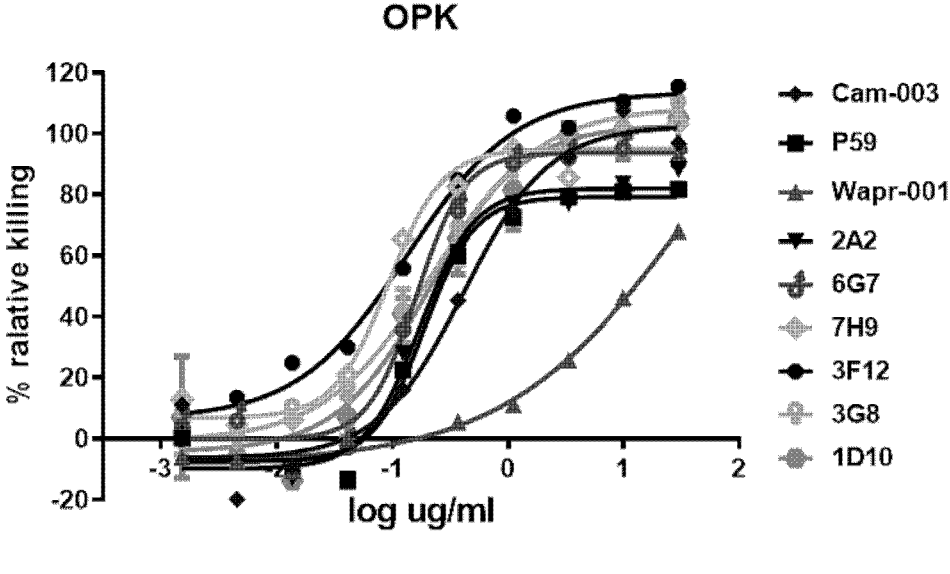
FIGS. 1C and 1D show the ability of the anti-Psl antibodies in promoting OPK of *P. aeruginosa* compared to the reference antibody Wapr-001 or Cam-003.
Figure 1D:
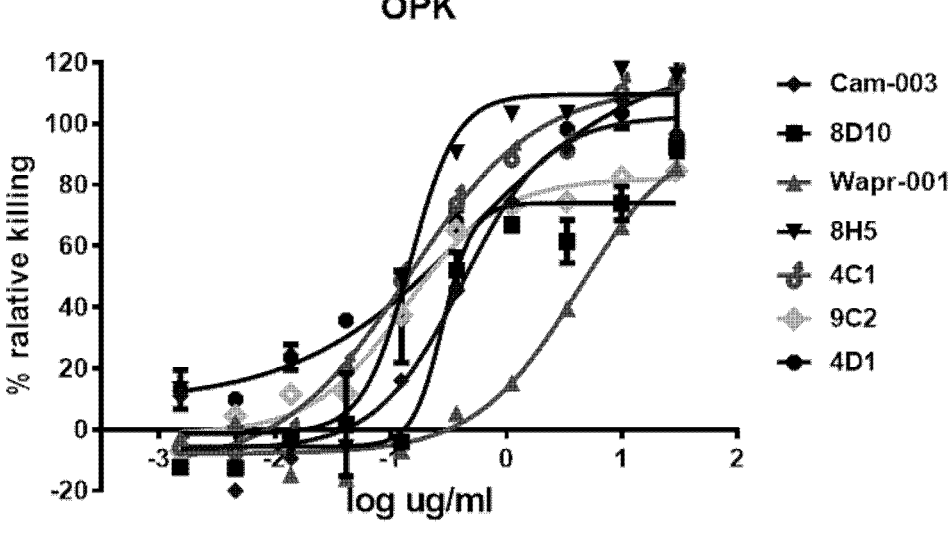
Figure 2A:
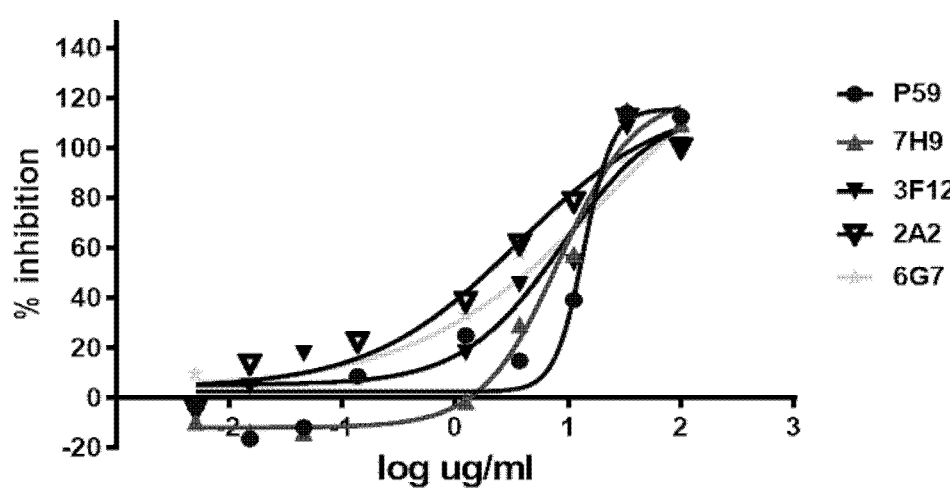
FIGS. 2A-2D show the ability of the anti-Psl antibodies P59, 7H9, 3F12, 2A2, and 6G7 in blocking the attachment of various *P. aeruginosa* strains O1-52/66, O6-57/66, O16-177/81, or O2-53/66 to A549 cells.
Figure 2B:
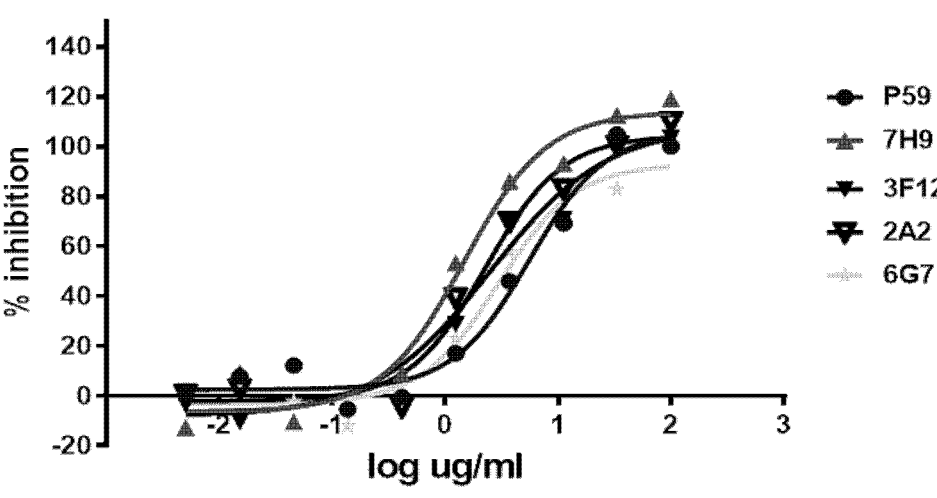
Figure 2C:
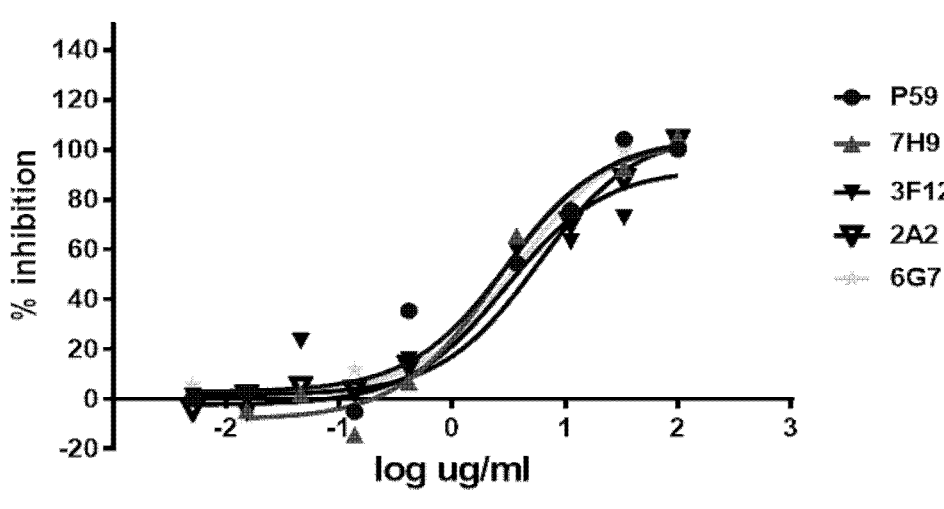
Figure 2D:
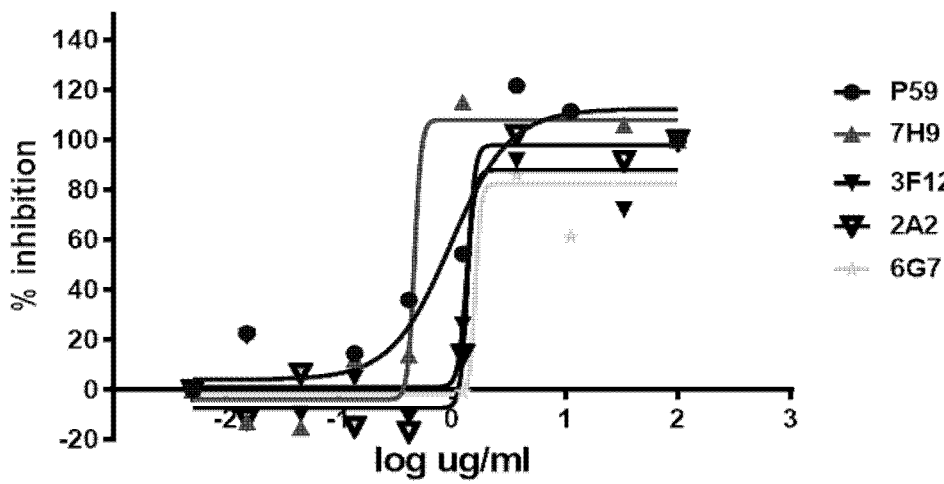
Figure 3A:
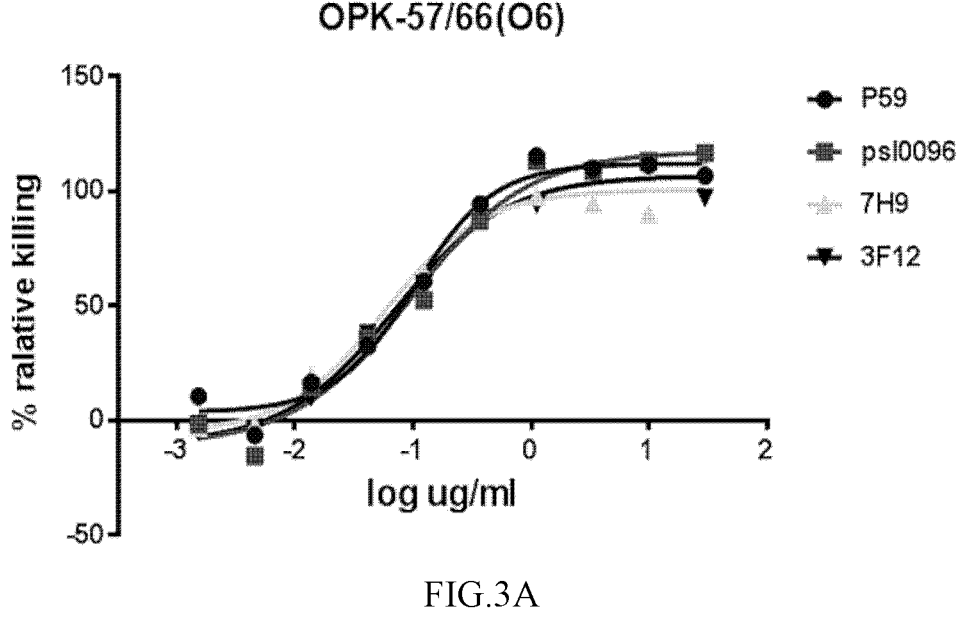
FIGS. 3A-3D show the ability of the anti-Psl antibodies P59, 7H9, and 3F12 in promoting OPK of various strains O6-57/66, O16-177/81, O1-52/66 or O2-53/66 as compared to the reference antibody psl0096.
Figure 3B:
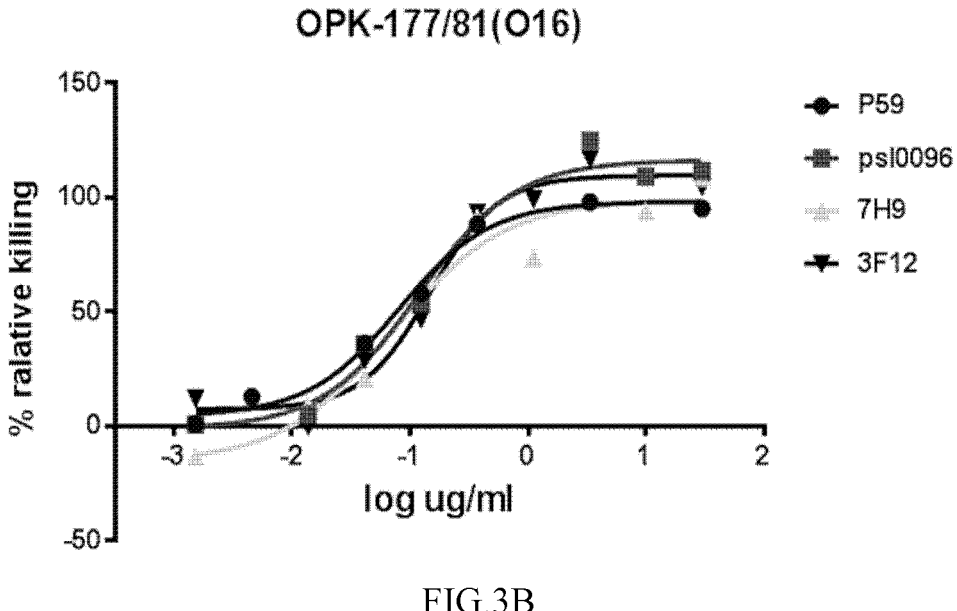
Figure 3C:
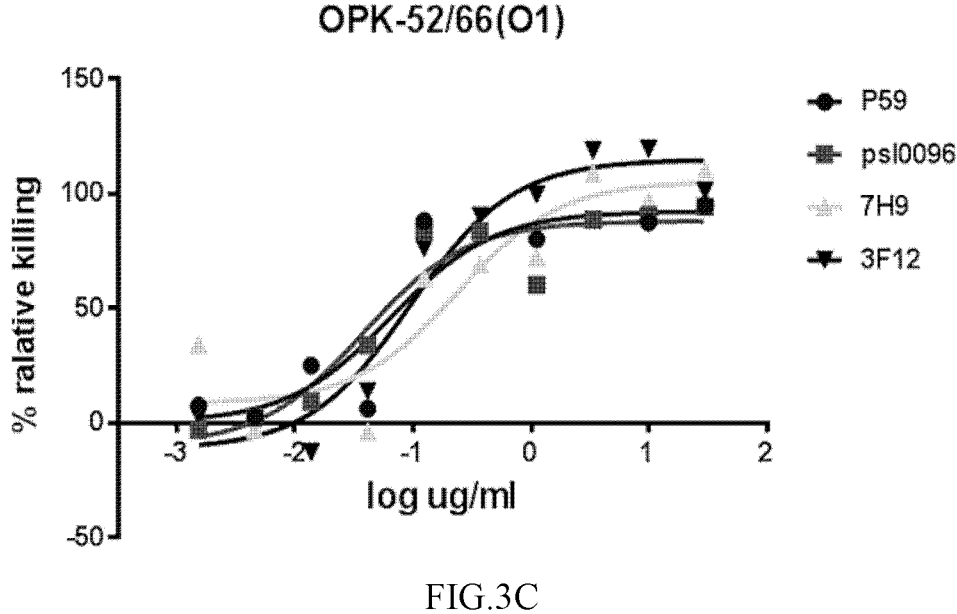
Figure 3D:
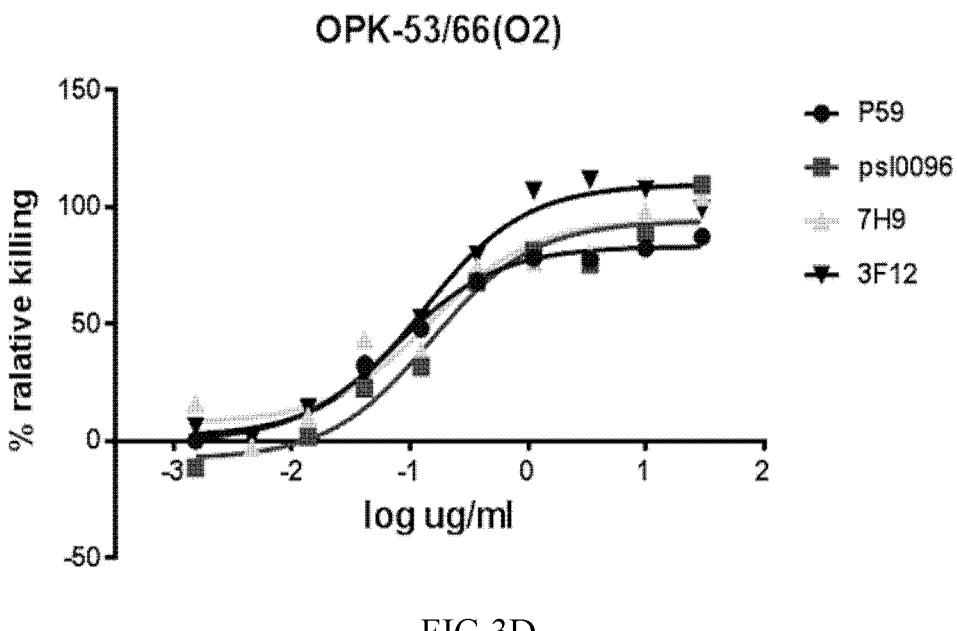
Figure 4A:
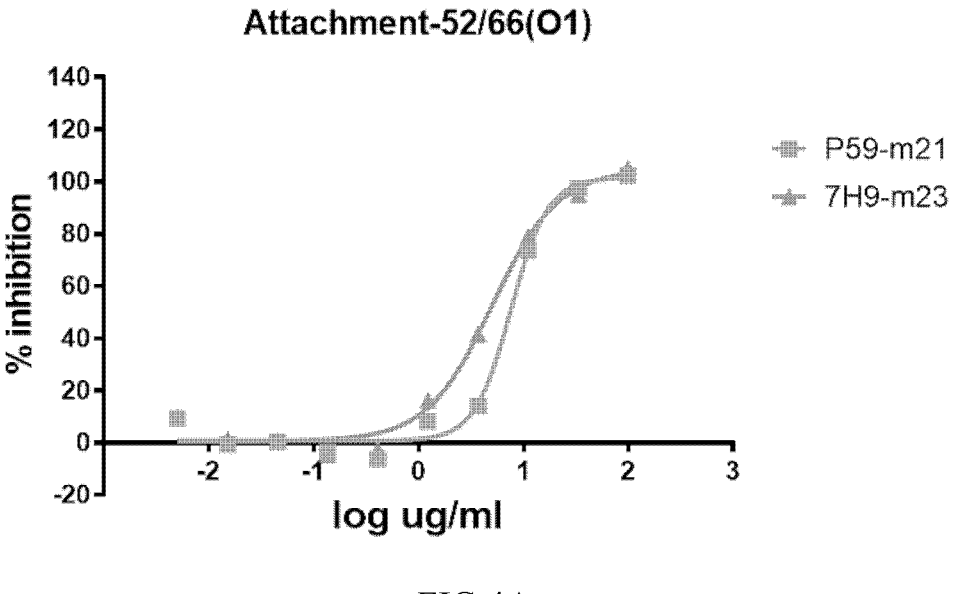
FIGS. 4A-4D show the ability of the anti-Psl antibody variant P59-m21, or 7H9-m23 in blocking the attachment of various *P. aeruginosa* strains O1-52/66, O2-53/66, O6-57/66, or O16-177/81 to A549 cells.
Figure 4B:
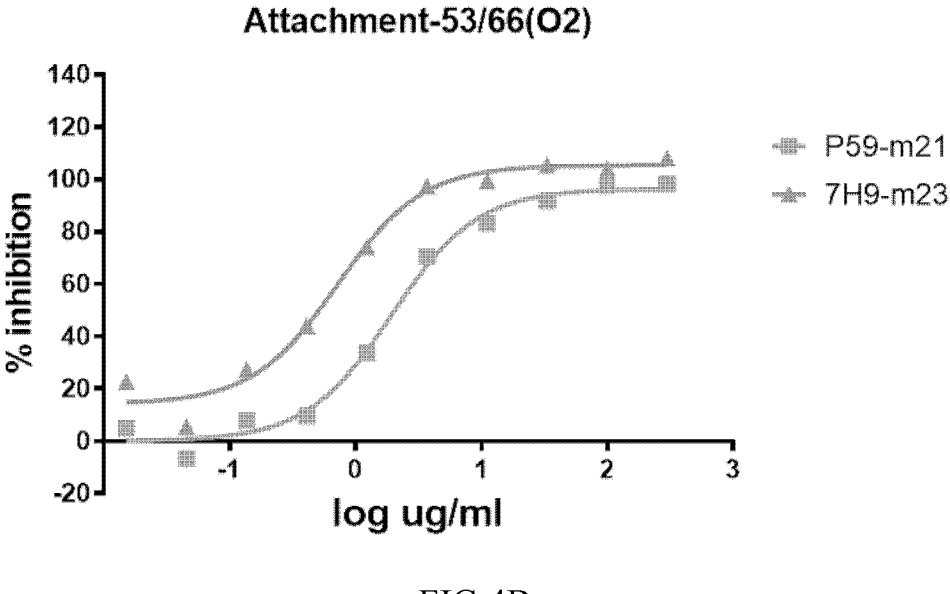
Figure 4C:
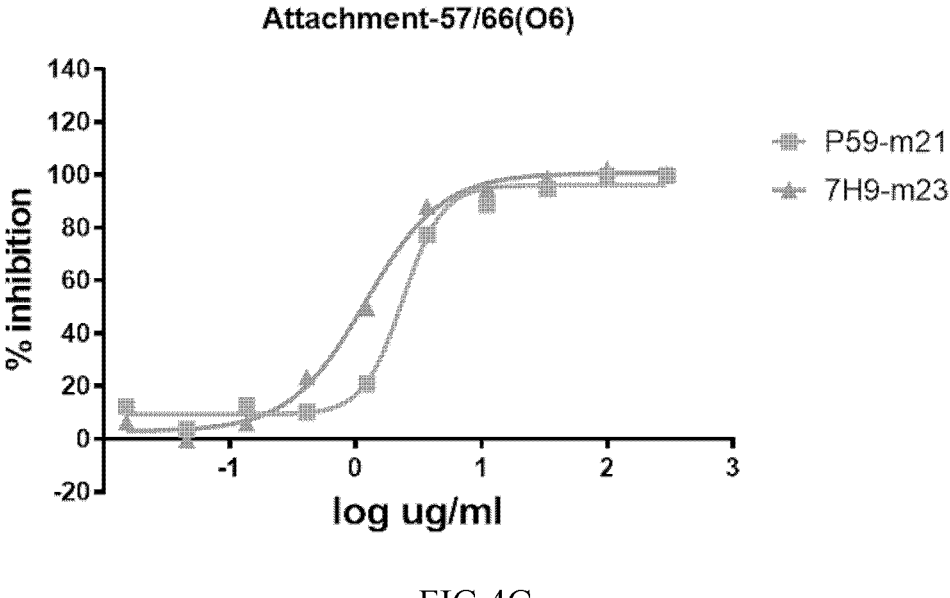
Figure 4D:
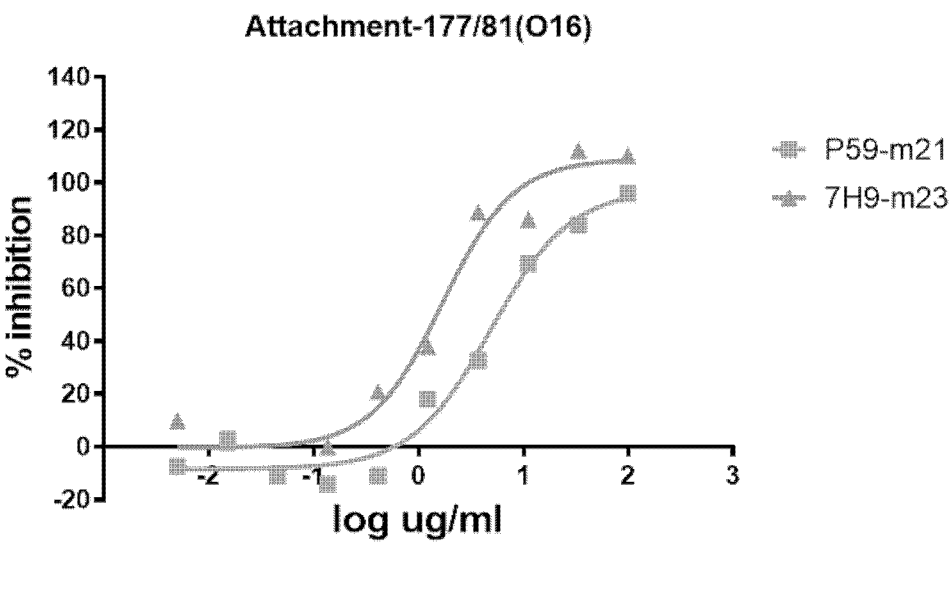
Figure 5A:
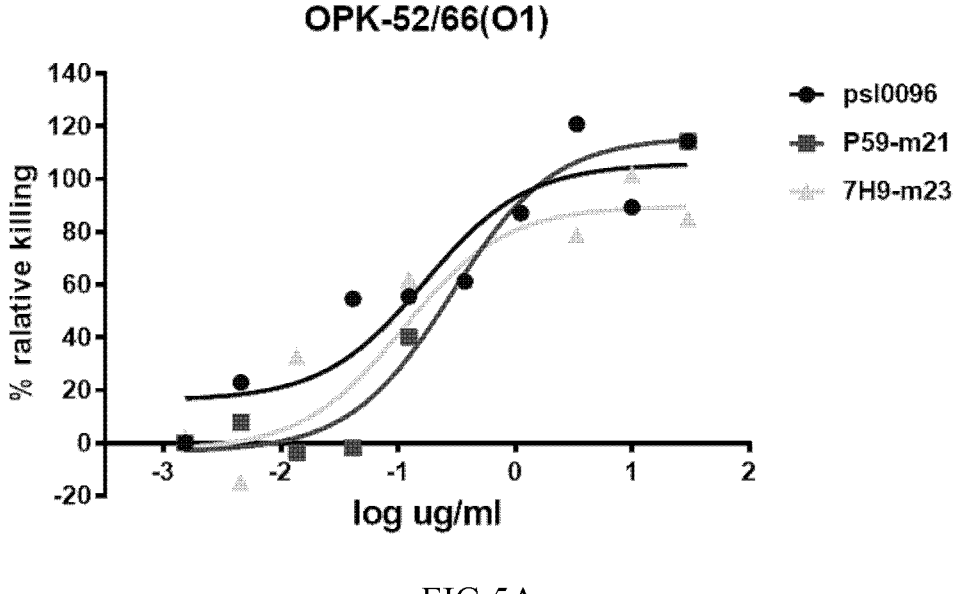
FIGS. 5A-5D show the ability of the anti-Psl antibody variant P59-m21, or 7H9-m23 in promoting OPK of various strains O1-52/66, O16-177/81, O6-57/66, or O2-53/66 as compared to the reference antibody psl0096.
Figure 5B:
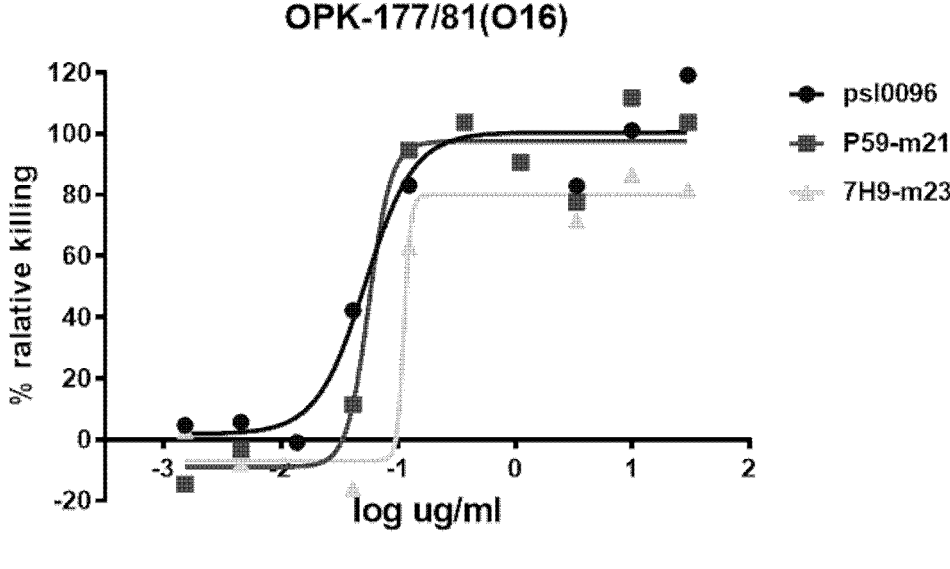
Figure 5C:
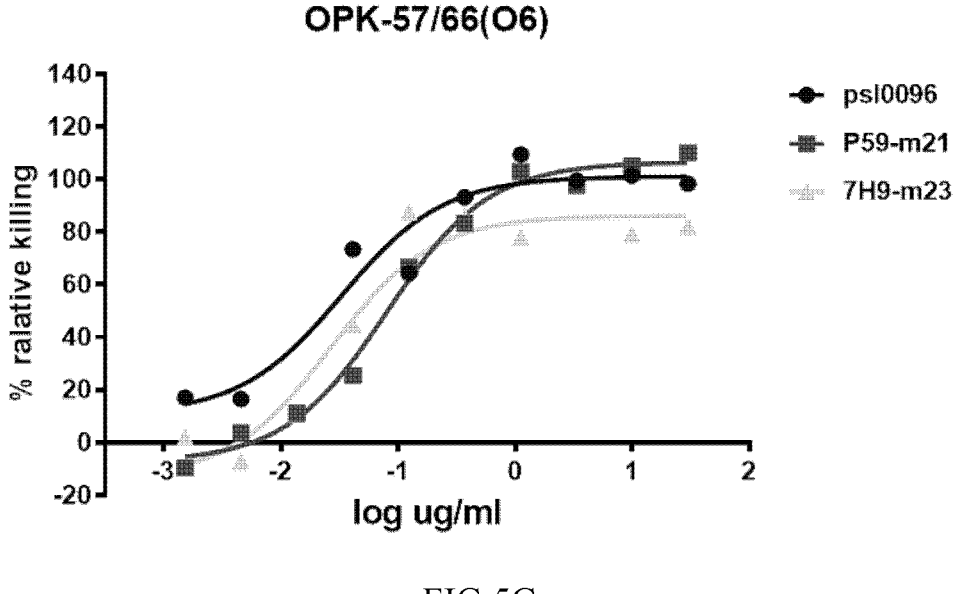
Figure 5D:
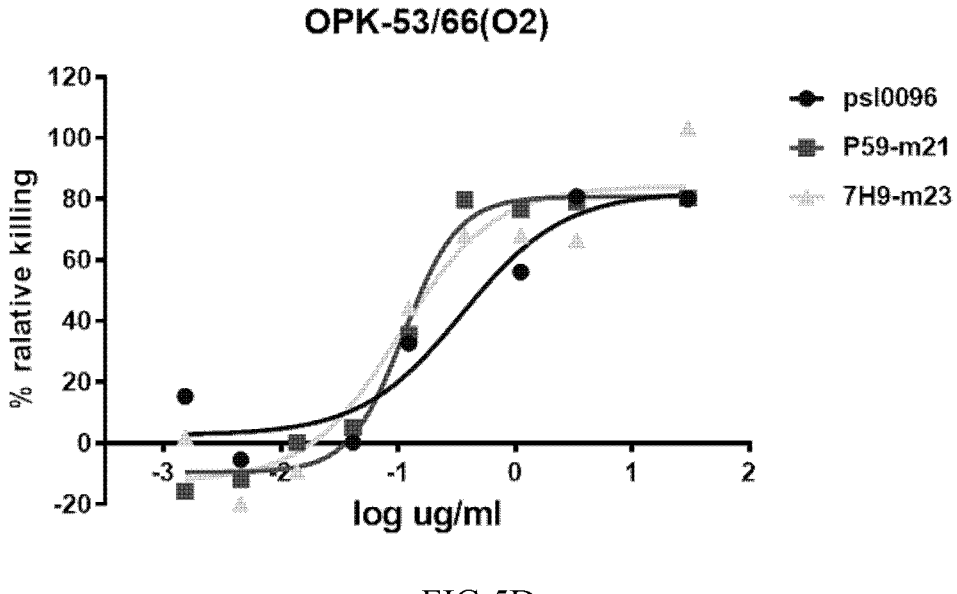

As shown in FIGS. 1C-1D and Table 10, all the anti-Psl antibodies exhibited significantly better efficacies in promoting OPK of *P. aeruginosa* as compared to the reference antibody Wapr-001, and exhibited better or comparable efficacies in promoting OPK of *P. aeruginosa* as compared to the reference antibody Cam-003.

TABLE 10

Efficacy of the anti-Psl antibodies in promoting OPK of *P. aeruginosa*

| Antibody | OPK (EC50 μg/ml) | Antibody | OPK (EC50 μg/ml) |
|---|---|---|---|
| Cam-003 | 0.3753 | 1D10 | 0.1830 |
| Wapr-001 | 5.5241 | 3G8 | 0.2218 |
| P59 | 0.1127 | 4D1 | 0.5088 |
| 2A2 | 0.1439 | 8D10 | 0.2515 |
| 6G7 | 0.0986 | 8H5 | 0.1038 |
| 7H9 | 0.0926 | 4C1 | 0.1696 |
| 3F12 | 0.1258 | 9C2 | 0.3599 |

Example 3: The Full-Length Anti-Psl Antibodies Broadly Neutralize *P. aeruginosa* Strains To examine whether the anti-Psl antibodies can neutralize a broad spectrum of *P. aeruginosa* strains, the ability of the anti-Psl antibodies to inhibit attachment of other clinically relevant *P. aeruginosa* strains to A549 cells and to promote OPK of other clinically relevant *P. aeruginosa* strains, for example, O1, O6, O16, or O2 *P. aeruginosa* strains, was evaluated.

Anti-Psl Antibodies Inhibit Attachment of Various Strains of *P. aeruginosa* to A549 Cells The anti-Psl mAbs P59, 7H9, 3F12, 2A2, and 6G7 were analyzed for their abilities to inhibit attachment of various strains of *P. aeruginosa* strains O1-52/66 (CNCTC 52/66), O6-57/66 (CNCTC 57/66), O16-177/81 (CNCTC 177/81), and O2-53/66 (CNCTC 53/66) to A549 cells. The luminescent *P. aeruginosa* 52/66 (O1)-LUX, 57/66 (O6)-LUX, 177/81 (O16)-LUX, and 53/66 (O2)-LUX bacteria were constructed by a PTN 7 transposon system as described in (Choi K H, et al. mini-Tn7 insertion in bacteria with single attTn7 sites: example *Pseudomonas aeruginosa*[J]. Nature Protocols, 2006, 1(1):153-161), and A549 cell attachment inhibition assay was performed as described in Example 2.

As shown in FIGS. 2A-2D and Table 11, the anti-Psl mAbs P59, 7H9, 3F12, 2A2, and 6G7 exhibited good efficacy in inhibiting attachment of *P. aeruginosa* strain O1-52/66, O6-57/66, O16-177/81, or O2-53/66 to A549 cells.

TABLE 11

Efficacy of the anti-Psl antibodies in blocking the attachment of various *P. aeruginosa* strains to A549 cells

| | Strain of *P. aeruginosa* | | | |
|---|---|---|---|---|
| Antibody | O1-52/66 IC50 (μg/mL) | O6-57/66 IC50 (μg/mL) | O16-177/81 IC50 (μg/mL) | O2-53/66 IC50 (μg/mL) |
| P59 | 13.58 | 5.50 | 3.07 | 0.96 |
| 7H9 | 6.10 | 1.46 | 2.44 | 0.46 |
| 3F12 | 8.73 | 2.49 | 2.97 | 1.33 |
| 2A2 | 4.28 | 2.25 | 5.71 | 1.36 |
| 6G7 | 6.89 | 2.94 | 3.89 | 1.60 |

Anti-Psl Antibodies Promote OPK of Various Strains of *P. aeruginosa*

The anti-Psl mAbs P59, 7H9, and 3F12 were analyzed for their abilities to promote OPK of various strains of *P. aeruginosa* (strains O6-57/66, O16-177/81, O1-52/66, and O2-53/66), as compared to the reference antibody psl0096. The luminescent *P. aeruginosa* 57/66 (O6)-LUX, 177/81 (O16)-LUX, 52/66 (O1)-LUX, and 53/66 (O2)-LUX bacteria were constructed by a PTN 7 transposon system, and OPK promotion assay was performed as described in Example 2.

As shown in FIGS. 3A-3D and Table 12, the anti-Psl mAbs P59, 7119, and 3F12, exhibited comparable or better efficacy in promoting OPK of the O6-57/66, O16-177/81, O1-52/66, or O2-53/66 strain, as compared to the reference antibody psl0096.

TABLE 12

Efficacy of the anti-Psl antibodies in promoting
OPK of various *P. aeruginosa* strains

| | Strain of *P. aeruginosa* | | | |
|---|---|---|---|---|
| Antibody | O6-57/66 EC50 (μg/mL) | O16-177/81 EC50 (μg/mL) | O1-52/66 EC50 (μg/mL) | O2-53/66 EC50 (μg/mL) |
| psl0096 | 0.1004 | 0.1179 | 0.0417 | 0.1510 |
| P59 | 0.1015 | 0.0805 | 0.0603 | 0.1343 |
| 7H9 | 0.0572 | 0.0717 | 0.1423 | 0.1505 |
| 3F12 | 0.0716 | 0.1473 | 0.1096 | 0.1287 |

Example 4: Identification of the Full-Length Variants of Anti-Psl Antibodies that Retain Biological Activity In order to reduce the isomerization and deamidation of the antibody, a panel of variants of full-length anti-Psl antibodies 7H9, P59, or 3F12 of IgG1 form containing single or combined mutations in the $V_H$ and $V_L$ domains were generated and purified by the methods known in the art, and subjected to A549 attachment blocking assay and OPK promoting assay as described in Example 2 to assess their biological activity. Cam-003 was used as the reference antibody. The IC50 values for inhibiting attachment of *P. aeruginosa* PAO1(O5) to A549 cells and EC50 values for promoting OPK of *P. aeruginosa* PAO1(O5) of the variants are shown in Table 13-18 below, demonstrating that all candidate antibody variants with the described mutations exhibit comparable or better functions as compared to the reference antibody Cam-003. The sequence numbering of the exemplary heavy chain and light chain variable domain of the anti-Psl antibody variants are shown in Table 6.

TABLE 13

Efficacy of the anti-Psl antibody 7H9 variants in blocking
attachment of *P. aeruginosa* to A549 cells

| Antibody Variants | ATT (IC50 μg/ml) |
|---|---|
| Cam-003 | 3.39 |
| 7H9 | 1.20 |
| 7H9-m01 | 1.78 |
| 7H9-m02 | 2.75 |
| 7H9-m03 | 2.21 |
| 7H9-m04 | 3.77 |
| 7H9-m05 | 3.48 |
| 7H9-m06 | 1.14 |

TABLE 13-continued

Efficacy of the anti-Psl antibody 7H9 variants in blocking
attachment of *P. aeruginosa* to A549 cells

| Antibody Variants | ATT (IC50 μg/ml) |
|---|---|
| 7H9-m07 | 0.92 |
| 7H9-m08 | 0.64 |
| 7H9-m09 | 0.95 |
| 7H9-m10 | 1.73 |
| 7H9-m11 | 1.42 |
| 7H9-m12 | 1.52 |
| 7H9-m13 | 2.11 |
| 7H9-m14 | 1.71 |
| 7H9-m15 | 1.83 |
| 7H9-m16 | 1.43 |
| 7H9-m17 | 1.72 |
| 7H9-m18 | 1.70 |
| 7H9-m19 | 2.04 |
| 7H9-m20 | 1.95 |
| 7H9-m21 | 1.05 |
| 7H9-m22 | 0.83 |
| 7H9-m23 | 1.25 |
| 7H9-m24 | 1.457 |
| 7H9-m25 | 1.53 |

TABLE 14

Efficacy of the anti-Psl antibody 7H9 variants
in promoting OPK of *P. aeruginosa*

| Antibody Variants | OPK (EC50 μg/ml) |
|---|---|
| Cam-003 | 0.3753 |
| 7H9 | 0.0926 |
| 7H9-m01 | 0.0869 |
| 7H9-m02 | 0.0758 |
| 7H9-m03 | 0.0536 |
| 7H9-m05 | 0.0420 |
| 7H9-m07 | 0.0662 |
| 7H9-m08 | 0.0383 |
| 7H9-m09 | 0.0534 |
| 7H9-m10 | 0.0512 |
| 7H9-m15 | 0.0490 |
| 7H9-m16 | 0.0650 |
| 7H9-m17 | 0.0410 |
| 7H9-m18 | 0.0266 |
| 7H9-m23 | 0.0284 |
| 7H9-m24 | 0.0846 |
| 7H9-m25 | 0.0812 |
| 7H9-m26 | 0.0491 |

TABLE 15

Efficacy of the anti-Psl antibody P59 variants in blocking
attachment of *P. aeruginosa* to A549 cells

| Antibody Variants | ATT (IC50 μg/ml) |
|---|---|
| Cam-003 | 3.39 |
| P59 | 2.29 |
| P59-m01 | 3.48 |
| P59-m02 | 2.51 |
| P59-m03 | 2.85 |
| P59-m04 | 2.32 |
| P59-m05 | 1.80 |
| P59-m06 | 2.57 |
| P59-m07 | 1.60 |
| P59-m08 | 2.02 |
| P59-m09 | 2.02 |
| P59-m10 | 2.26 |
| P59-m11 | 2.16 |
| P59-m12 | 3.09 |
| P59-m13 | 3.43 |
| P59-m14 | 3.33 |
| P59-m15 | 2.93 |

US 12,570,727 B2

163

TABLE 15-continued

Efficacy of the anti-Psl antibody P59 variants in blocking
attachment of *P. aeruginosa* to A549 cells

| Antibody Variants | ATT (IC50 μg/ml) |
|---|---|
| P59-m16 | 2.14 |
| P59-m17 | 1.53 |
| P59-m18 | 1.85 |
| P59-m19 | 2.47 |
| P59-m20 | 2.21 |
| P59-m21 | 2.52 |
| P59-m22 | 4.61 |
| P59-m23 | 2.53 |
| P59-m24 | 2.66 |
| P59-m25 | 2.01 |
| P59-m26 | 3.49 |
| P59-m27 | 2.67 |
| P59-m28 | 2.22 |
| P59-m29 | 3.11 |
| P59-m30 | 2.21 |
| P59-m31 | 3.19 |
| P59-m32 | 2.76 |
| P59-m33 | 2.75 |

TABLE 16

Efficacy of the anti-Psl antibody P59 variants
in promoting OPK of *P. aeruginosa*

| Antibody Variants | OPK (EC50 μg/ml) |
|---|---|
| Cam-003 | 0.3753 |
| P59 | 0.1127 |
| P59-m03 | 0.0542 |
| P59-m04 | 0.0503 |
| P59-m05 | 0.0454 |
| P59-m07 | 0.1151 |
| P59-m13 | 0.1319 |
| P59-m15 | 0.0649 |
| P59-m16 | 0.0530 |
| P59-m17 | 0.1110 |
| P59-m18 | 0.1063 |
| P59-m21 | 0.0839 |
| P59-m22 | 0.1062 |
| P59-m23 | 0.2215 |

TABLE 17

Efficacy of the anti-Psl antibody 3F12 variant in blocking
attachment of *P. aeruginosa* to A549 cells

| Antibody Variant | ATT (IC50 μg/ml) |
|---|---|
| Cam-003 | 3.39 |
| 3F12 | 2.12 |
| 3F12-m01 | 1.279 |

TABLE 18

Efficacy of the anti-Psl antibody 3F12 variant
in promoting OPK of *P. aeruginosa*

| Antibody Variant | OPK (EC50 μg/ml) |
|---|---|
| Cam-003 | 0.3753 |
| 3F12 | 0.1258 |
| 3F12-m01 | 0.1233 |

Variants of Anti-Psl Antibodies Broadly Neutralize *P. aeruginosa* Strains

To examine whether these variants can neutralize a broad spectrum of *P. aeruginosa* strains, the ability of these variants to block the attachment of *P. aeruginosa* to A549 cells and mediate OPK activity against other clinically relevant *P. aeruginosa* strains, for example, O1, O6, O16, or O2 *P. aeruginosa* strains, was evaluated.

Variants of Anti-Psl Antibodies Block Attachment of Various Strains of *P. aeruginosa* to A549 Cells The variants of anti-Psl antibodies P59-m21 and 7H9-m23 were further analyzed for their abilities to block the attachment of various strains of *P. aeruginosa*, namely strains O1-52/66, O2-53/66, O6-57/66, and O16-177/81 to A549 cells. The luminescent *P. aeruginosa* 52/66 (O1)-LUX, 53/66 (O2)-LUX, 57/66 (O6)-LUX, and 177/81 (O16)-LUX bacteria were constructed by a PTN 7 transposon system, and A549 cell attachment inhibition assay was performed as described in Example 2.

As shown in FIGS. 4A-4D and Table 19, the variants of anti-Psl antibodies P59-m21 and 7H9-m23 exhibited good efficacy in blocking the attachment of *P. aeruginosa* strain O1-52/66, O2-53/66, O6-57/66, or O16-177/81 to A549 cells.

TABLE 19

Efficacy of the anti-Psl variants in blocking the attachment
of various *P. aeruginosa* strains to A549 cells

| | Strain of *P. aeruginosa* | | | |
|---|---|---|---|---|
| Antibody Vriants | O1-52/66 IC50 (μg/mL) | O2-53/66 IC50 (μg/mL) | O6-57/66 IC50 (μg/mL) | O16-177/81 IC50 (μg/mL) |
| P59-m21 | 7.63 | 1.94 | 2.38 | 4.90 |
| 7H9-m23 | 5.04 | 0.72 | 1.20 | 1.69 |

Variants of anti-Psl antibodies promote OPK of various strains of *P. aeruginosa*

The variants of anti-Psl antibodies P59-m21 and 7H9-m23 were analyzed for their abilities to promote OPK of various strains of *P. aeruginosa*, namely strains O1-52/66, O16-177/81, O6-57/66, and O2-53/66, as compared to the reference antibody psl0096. The luminescent *P. aeruginosa* 52/66 (O1)-LUX, 177/81 (O16)-LUX, 57/66 (O6)-LUX, and 53/66 (O2)-LUX bacteria were constructed by a PTN 7 transposon system, and the OPK promotion assay was performed as described in Example 2.

As shown in FIGS. 5A-5D and Table 20, the variants of anti-Psl antibodies P59-m21 and 7H9-m23 exhibited comparable or better efficacy in promoting OPK of O1-52/66, O16-177/81, O6-57/66, or O2-53/66 strain as compared to the reference antibody psl0096.

TABLE 20

Efficacy of the anti-Psl variants in promoting
OPK of various *P. aeruginosa* strains

| | Strain of *P. aeruginosa* | | | |
|---|---|---|---|---|
| mAb clones | O1-52/66 EC50 (μg/mL) | O16-177/81 EC50 (μg/mL) | O6-57/66 EC50 (μg/mL) | O2-53/66 EC50 (μg/mL) |
| psl0096 | 0.1174 | 0.0526 | 0.0642 | 0.3055 |
| P59-m21 | 0.2435 | 0.0584 | 0.0713 | 0.1225 |
| 7H9-m23 | 0.3214 | 0.0912 | 0.0562 | 0.1787 |

Example 5: Characterizing the Binding Specificity of the Anti-Psl Antibodies

Binding Affinity of the Variants of Anti-Psl Antibodies

The binding kinetics and affinity of the variants of anti-Psl antibodies 3F12-m01, 7H9-m23, P59-m21, and the reference antibody psl0096 to Psl were tested by BLI (Bio-Layer Interferometry), as shown in Table 21.

TABLE 21

| Binding affinity of the variants of anti-Psl antibodies to Psl | | | |
|---|---|---|---|
| Antibody | Kon(1/Ms) | Kdis(1/s) | Kd (M) |
| 3F12-m01 | 1.81E+05 | 1.65E−03 | 9.10E−09 |
| 7H9-m24 | 3.90E+05 | 8.32E−04 | 2.13E−09 |
| P59-m21 | 2.36E+05 | 1.84E−03 | 7.80E−09 |
| psl0096 | 4.37E+05 | 1.42E−03 | 3.24E−09 |

Binding with the Recombinant *P. aeruginosa* WFPA801 or WFPA800 Strain

The binding specificity of anti-Psl antibodies and the reference antibody psl0096 to WFPA801 or WFPA800 strain were tested using ELISA according to the method described previously (See Ma, L., et al, 2006, *J Bacteriol* 188: 8213-8221). Briefly, WFPA800 (Δpsl), the psl promoter deletion mutant of *P. aeruginosa* PAO1, or WFPA801 ($p_{BAD}$-psl), the psl-inducible strain was used in this study. ELISA plates were coated with the strain WFPA801 or WFPA800 at 4° C. overnight. After blocking, serial dilutions of the antibodies were added and incubated at 37° C. for 1 hour. After washing, the alkaline phosphatase-labeled anti-human IgG antibody (Goat Anti-Human IgG (whole molecule)-HRP, Sigma, A8667) was added and incubated at 37° C. for 1 hour. PNPP was added to each well to develop color. 3M NaOH was used to terminate the reaction. The signals were read by a microplate reader at 410 nm.

Figure 6A:
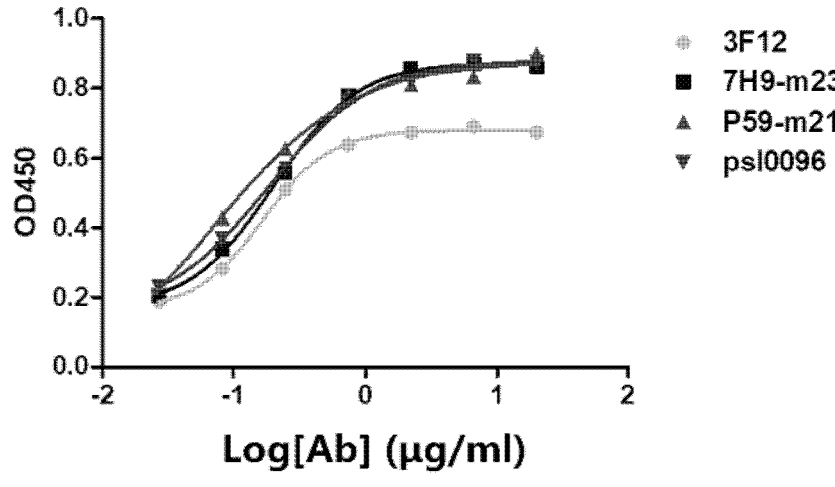
FIGS. 6A-6B show the binding specificity of the anti-Psl antibodies 3F12, 7H9-m23, and P59-m21 to WFPA800 strain or WFPA801 strain as measured by ELISA.
Figure 6B:
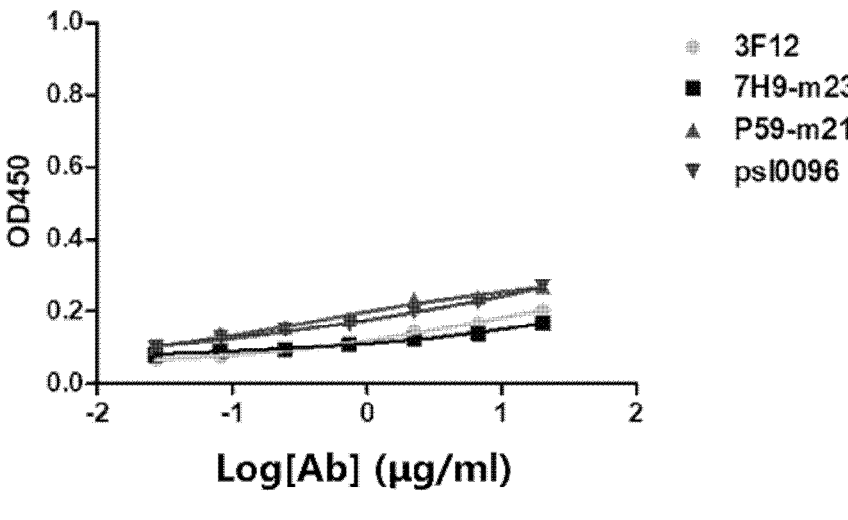

As shown in FIGS. 6A-6B and Table 22, the anti-Psl antibodies 3F12, 7H9-m23, P59-m21, and the reference antibody psl0096 all displayed low levels of binding to WFPA800 strain. In contrast, all tested antibodies exhibited high levels of specific-binding to WFPA801 strain.

TABLE 22

| Efficacy of anti-Psl antibodies Cross-reactivity to WFPA801 | | | | |
|---|---|---|---|---|
| Antibody | 3F12 | 7H9-m23 | P59-m21 | psl0096 |
| EC50(μg/mL) | 0.167 | 0.203 | 0.070 | 0.183 |

Non-Specificity of Anti-Psl Antibodies

The anti-Psl antibodies 3F12, 7H9-m23, and P59-m21 were further characterized for their non-specificity binding, as compared to the reference antibody psl0096.

Cross-reactivity to BV particles: Using ELISA, the anti-Psl antibodies and the reference antibody psl0096 were tested for the cross-reactivity to BV particles according to the method described previously (See Hötzel I, et al, 2012, mAbs 4:6, 753-760). Lenzilumab was used as the positive control, and Tildrakizumab was used as the negative control. The BV score is the ratio of the OD value of the assay with the antibody tested to the OD value of the assay without adding the antibody.

Figure 7:
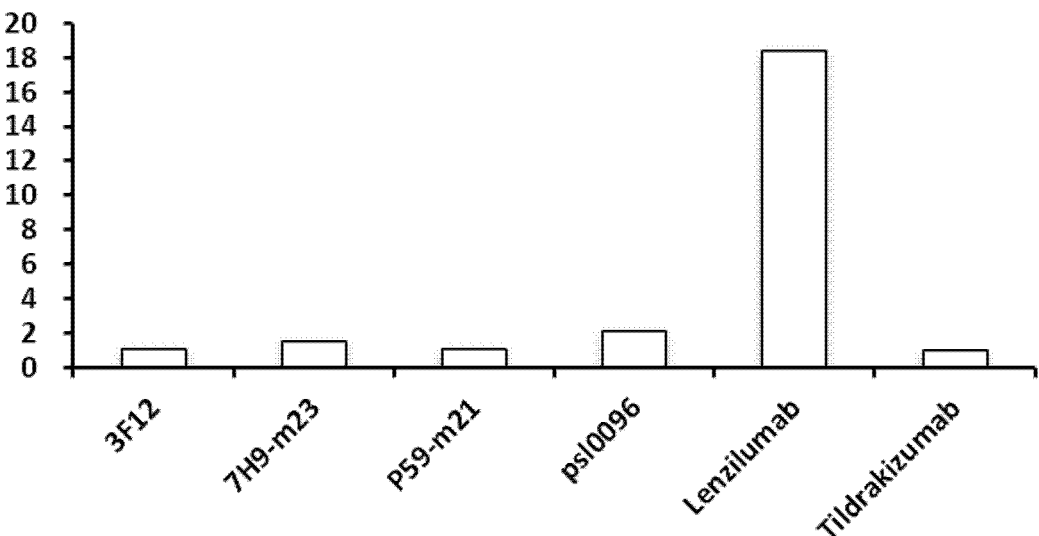
FIG. 7 shows the cross-reactivity of the anti-Psl antibodies 3F12, 7H9-m23, and P59-m21 to BV particles as compared to the reference antibody psl0096.

As shown in FIG. 7 and Table 23, the positive control displayed a high level of binding to BV particles. In contrast, the antibodies 3F12, 7H9-m23, or P59-m21 displayed very low level of binding to BV particles, which is lower than or comparable to the reference antibody psl0096, like the negative control.

TABLE 23

| Efficacy of anti-Psl antibodies Cross-reactivity to BV particles | | | | | | |
|---|---|---|---|---|---|---|
| Antibody | 3F12 | 7H9-m23 | P59-m21 | psl0096 | Lenzilumab | Tildrakizumab |
| BV Score | 1.1 | 1.5 | 1.1 | 2.1 | 18.4 | 1.0 |

Taken together, these results indicate that the anti-Psl antibodies 3F12, 7H9-m23, and P59-m21 displayed comparable or lower levels of non-specific binding when compared to the reference antibody psl0096.

Example 6: Anti-Psl Antibodies Inhibit Biofilm Formation of *P. aeruginosa* PAO1(O5) Strain

*P. aeruginosa* is the most common model organism for biofilm development as it has long been associated with biofilm formation in chronic cystic fibrosis lung infections. The formation of the biofilm is an important mechanism leading to colonization of chronic infection and antibiotic resistance. Psl polysaccharide is an important component of *Pseudomonas aeruginosa* to form biofilm, and effective anti-Psl antibodies should theoretically have the function of inhibiting biofilm formation. The ability of the anti-Psl antibodies 3F12, P59-m21, 7H9-m23 and the reference antibody psl0096 to inhibit biofilm formation of *P. aeruginosa* was demonstrated in the following experiment, wherein an HIV neutralizing antibody 10E8 (Huang J, et al., Broad and potent neutralization of HIV-1 by a gp41-specific human antibody. *Nature*. 2012 Nov. 15; 491(7424):406-12) was used as a negative control, herein named HIV-10E8. Briefly, the *P. aeruginosa* colony was picked into the liquid medium and cultured overnight at 37° C. The OD600 value of the medium containing *P. aeruginosa* was adjusted to 1.0 and was diluted $10^6$ times, and 100 μL of the diluted *P. aeruginosa* and the anti-Psl antibody were added into a 96-well plate and incubated for 24h at 30° C. Subsequently, the culture medium was gently removed, and the plate was washed 3 times with sterile water, thereby removing the bacteria which did not form the biofilm. 150 μL of 1% crystal violet was added to each well for 20 minutes to allow staining. The plate was washed with sterile water 3 times, and 150 μL of 33% acetic acid was added and incubated for 20 minutes to extract crystal violet. The acetic acid containing crystal violet was transferred to another well and the OD values were read at 490 nm. The OD490 value of the assay without adding the anti-Psl antibody was designated as 100% of the biofilm formation, and the value of the assay without adding *P. aeruginosa* was designated as 0% of the biofilm formation, with which the percentage of the biofilm formation was calculated.

Figure 8:
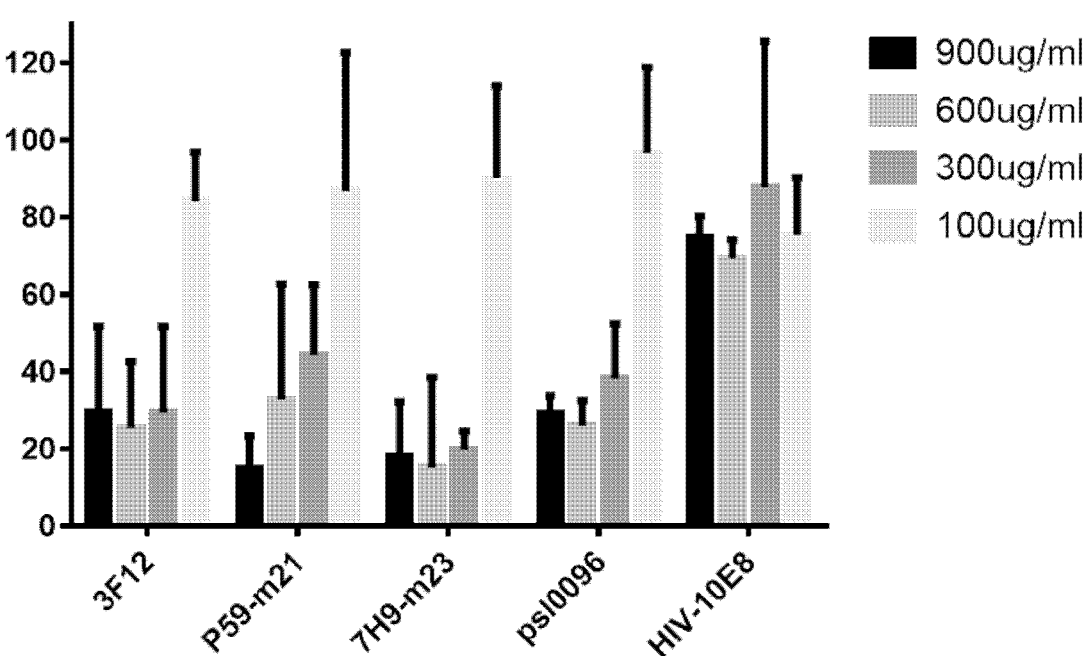
FIG. 8 shows the ability of the anti-Psl antibodies 3F12, 7H9-m23, and P59-m21 with different dosages in inhibiting *P. aeruginosa* biofilm formation as compared to the reference antibody psl0096.

As shown in FIG. 8, all the anti-Psl antibodies tested exhibited remarkable effects in inhibiting biofilm formation at a dosage ranging from 300 to 900 μg/ml as compared to the negative control (P<0.05). In particular, the anti-Psl antibodies 3F12, 7H9-m23, and P59-m21 exhibited better or comparable efficacy in inhibiting the biofilm formation as compared to the reference antibody psl0096.

Example 7: Survival Rates of Animals Treated with Anti-Psl Antibodies in a Mouse *P. aeruginosa* Bacteremia Model The ability of the anti-Psl antibodies to improve survival in a mouse bacteremia model was evaluated. HIV-10E8 was used as a negative control. The mouse bacteremia model caused by intraperitoneal infection was generated as described previously (See Warrener et al., 2014, *Antimicrob. Agents Chemother.*, 58, 4384-4391).

Survival Improvement in Mouse Bacteremia Model by Anti-Psl Antibody at a Higher Dosage The ability of the anti-Psl antibody P59 (at a higher dosage of 15 mg/kg mouse weight) to improve survival in a mouse bacteremia model was evaluated in comparison with the reference antibody Cam-003. HIV-10E8 was used as a negative control.

To induce mouse bacteremia model, 7-8 weeks old BALB/c mice (Vital River Laboratory) were randomly assigned into groups, with 8-10 mice for each group. Antibodies were administered by intraperitoneal (i.p.) injection 24 hours before infection at the dose of 15 mg/kg mouse weight. The mice were intraperitoneally inoculated with *P. aeruginosa* (O6-57/66 strain), which could represent the highly virulent cytotoxic *P. aeruginosa* serotype associated with clinical diseases, at twice the lethal dose ($2 \times LD_{90} = 5 \times 10^5$ CFU). Mice survival were recorded for up to 5 days post-infection.

Figure 9A:
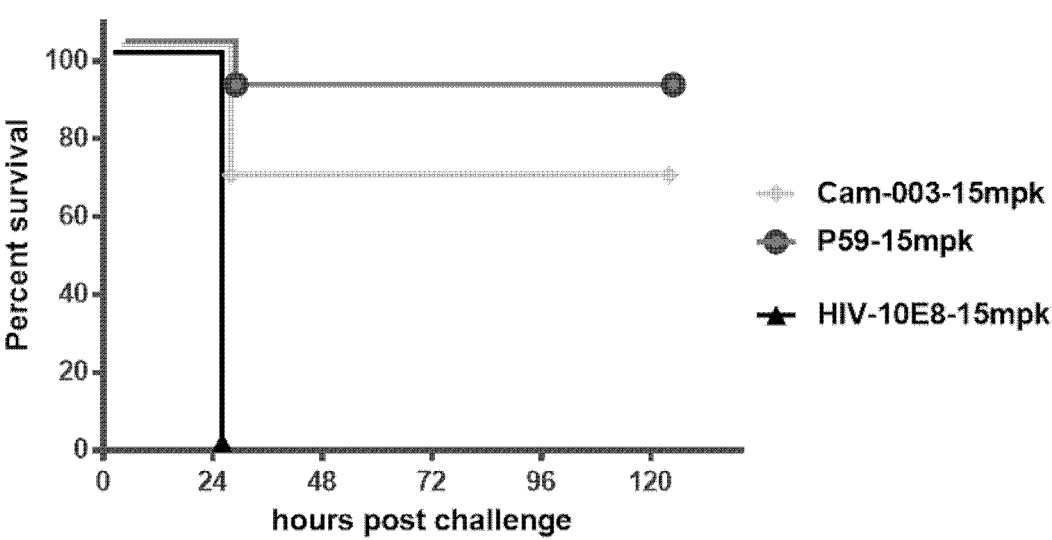
FIG. 9A shows the ability of the anti-Psl antibody P59 at dose of 15 mg/kg mouse weight to improve survival in a mouse bacteremia model at twice the lethal dose ($2 \times LD_{90}$) of *P. aeruginosa* inoculation compared to the reference antibody Cam-003.

As shown in FIG. 9A, at twice the lethal dose ($2 \times LD_{90}$) of *P. aeruginosa* inoculation, the anti-Psl antibody P59 exhibited significantly better protection than the reference antibody Cam-003 did at the same dose (P<0.05). Differences in survival rate were calculated by the log-rank test.

Survival Improvement in Mouse Bacteremia Model by Anti-Psl Antibody at a Lower Dosage The ability of the anti-Psl antibodies P59, 1D10, 7H9, 2A2, and 6G7 (at a lower antibody dosage of 10 mg/kg mouse weight) to improve survival in a mouse bacteremia model was evaluated in comparison with the reference antibody Cam-003. HIV-10E8 was used as a negative control.

7-8 weeks old BALB/c mice (Vital River Laboratory) were randomly assigned into groups, with 8-10 mice for each group. Antibodies were administered by intraperitoneal (i.p.) injection 24 hours before infection at doses of 10 mg/kg mouse weight. The mice were intraperitoneally inoculated with *P. aeruginosa* (O6-57/66 strain) at triple the lethal dose ($3 \times LD90 = 7 \times 10^5$ CFU). Mice survival was recorded for up to 6 days post-infection.

Figure 9B:
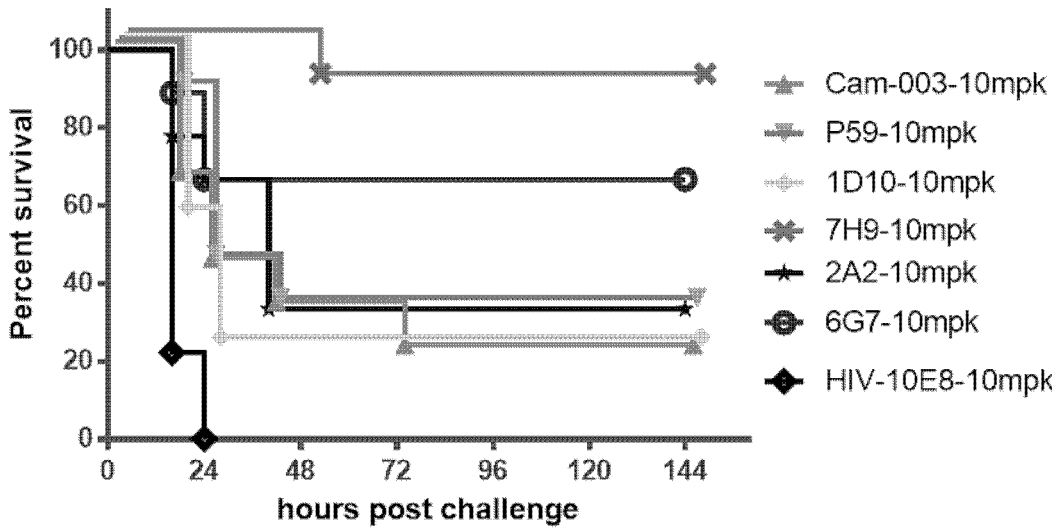
FIG. 9B shows the ability of the anti-Psl antibody P59, 1D10, 7H9, 2A2, or 6G7 at dose of 10 mg/kg mouse weight to improve survival in a mouse bacteremia model at triple the lethal dose ($3 \times LD_{90}$) of *P. aeruginosa* inoculation compared to the reference antibody Cam-003.

As shown in FIG. 9B, at triple the lethal dose ($3 \times LD_{90}$) of *P. aeruginosa* inoculation, and the lower antibody dosage of 10 mg/kg mouse weight, all anti-Psl antibodies exhibited significant survival improvement as compared to negative control HIV-10E8(P<0.05). Also, the anti-Psl antibody 7H9 and 6G7 exhibited significantly better survival improvement than the reference antibody Cam-003 (P<0.05), while the anti-Psl antibodies P59, 1D10, and 2A2 exhibited comparable or better survival improvement as compared to the reference antibody Cam-003. Differences in survival were calculated by the log-rank test.

Survival Improvement in Mouse Bacteremia Model by the Anti-Psl Antibody with a Lower Dosage and Higher *P. aeruginosa* Inoculation The ability of the anti-Psl antibodies 3F12 and 7H9 to improve survival in a mouse bacteremia model at a lower antibody dosage of 10 mg/kg mouse weight and a higher *P. aeruginosa* inoculation ($4 \times LD90 = 9 \times 10^5$ CFU)) was evaluated in comparison with the reference antibody psl0096. HIV-10E8 was used as a negative control.

7-8 weeks old BALB/c mice (Vital River Laboratory) were randomly assigned into groups, with 8-10 mice for each group. Anti-Psl antibodies were administered by intraperitoneal (i.p.) injection 24 hours before infection at a dose of 10 mg/kg mouse weight. The mice were intraperitoneally inoculated with *P. aeruginosa* (O6-57/66 strain) at 4 times the lethal dose ($4 \times LD90 = 9 \times 10^5$ CFU). Mice survival was recorded for up to 6 days post-infection.

Figure 9C:
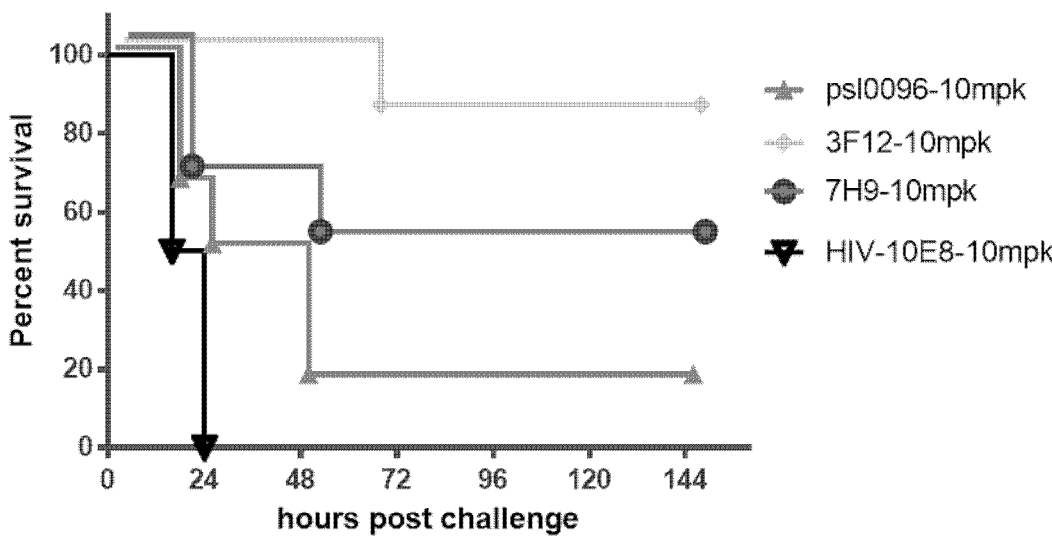
FIG. 9C shows the ability of the anti-Psl antibody 3F12 or 7H9 at dose of 10 mg/kg mouse weight to improve survival in a mouse bacteremia model at 4 times the lethal dose ($4 \times LD_{90}$) of *P. aeruginosa* inoculation compared to the reference antibody psl0096.

As shown in FIG. 9C, at 4 times the lethal dose ($4 \times LD_{90}$) of *P. aeruginosa* inoculation and a lower antibody dosage of 10 mg/kg mouse weight, anti-Psl antibodies 3F12 and 7H9 exhibited significantly better survival improvement than the reference antibody psl0096(P<0.05). Differences in survival were calculated by the log-rank test.

Survival Improvement in Mouse Bacteremia Model by the Variants of Anti-Psl Antibodies The ability of the variants of anti-Psl antibodies 7H9-m23, 7H9-m24, 7H9-m25, 3F12-m01, and P59-m21 to improve survival in a mouse bacteremia model at a lower antibody dosage (10 mg/kg mouse weight) and a higher *P. aeruginosa* inoculation ($4 \times LD90 = 9 \times 10^5$ CFU) was evaluated. HIV-10E8 was used as a negative control.

7-8 weeks old BALB/c mice (Vital River Laboratory) were randomly assigned into groups, with 8-10 mice for each group. Variants of the anti-Psl antibodies were administered by intraperitoneal (i.p.) injection 24 hours before infection at a doses of 10 mg/kg mouse weight. The mice were intraperitoneally inoculated with *P. aeruginosa* (O6-57/66 strain) at 4 times the lethal dose ($4 \times LD90 = 9 \times 10^5$ CFU). Mice survival was recorded for up to 6 days post-infection.

Figure 9D:
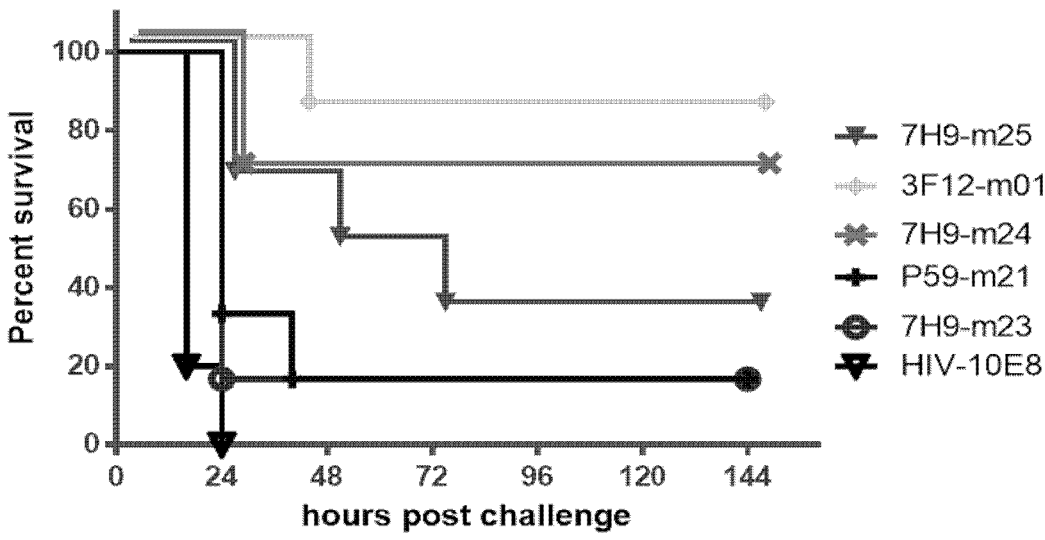
FIG. 9D shows the ability of the anti-Psl antibody variant 7H9-m23, 7H9-m24, 7H9-m25, 3F12-m01, or P59-m21 at dose of 10 mg/kg mouse weight to improve survival in a mouse bacteremia model at 4 times the lethal dose ($4 \times LD_{90}$) of *P. aeruginosa* inoculation.

As shown in FIG. 9D, at 4 times the lethal dose ($4 \times LD90$) of *P. aeruginosa* inoculation and a lower antibody dosage of 10 mg/kg mouse weight, all the variants of anti-Psl antibodies 7H9-m23, 7H9-m24, 7H9-m25, 3F12-m01 and P59-m21 exhibited significant survival improvement as compared to the negative control HIV-10E8 (P<0.05). Differences in survival were calculated by the log-rank test.

Example 8: Variants of Anti-Psl Antibodies Reduce Organ Burden in a Mouse Acute Pneumonia Model The ability of the variants of anti-Psl antibodies 3F12-m01, 7H9-m24, and P59-m21 to reduce *P. aeruginosa* organ burden in a mouse acute pneumonia model was evaluated. HIV-10E8 was used as the negative control.

7-8 weeks old BALB/c mice (Vital River Laboratory) were administered with antibodies or PBS intraperitoneally (i.p.) 24 hours before infection, at 15 mg/kg mouse weight. To induce acute pneumonia, the mice were intranasally inoculated with *P. aeruginosa* (57/66 strain) at $5 \times 10^6$ CFU. At 24 hours post-infection, mice were euthanized, followed by harvesting of lungs, spleens, and kidneys for determination of the viable bacteria forming units (in CFU), which represented the *P. aeruginosa* burden in the respective organ sample.

Figure 10:
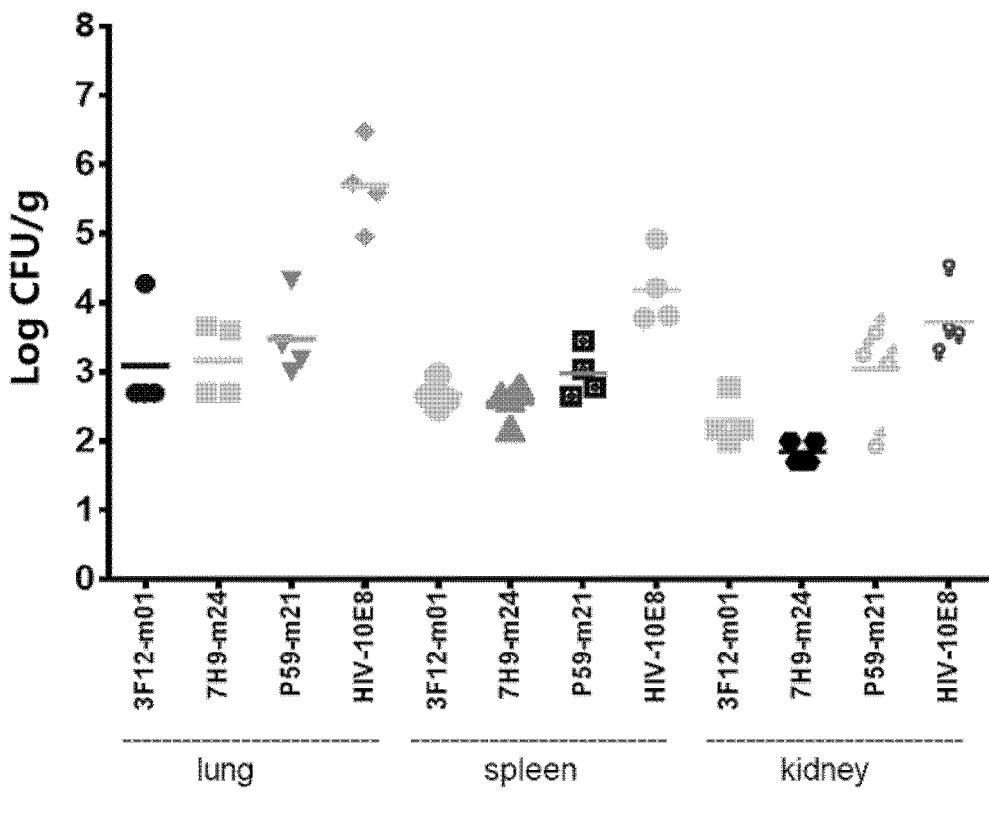
FIG. 10 shows the ability of the anti-Psl antibody variant 3F12-m01, 7H9-m24, or P59-m21 in reducing organ bacteria burden in the lung, spleen, and kidney.

As shown in FIG. 10, all the variants of anti-Psl antibodies 3F12-m01, 7H9-m24, and P59-m21 exhibited better efficacy in reducing organ burden in lung, spleen, and kidney as compared to the negative control HIV-10E8 (P<0.05).

Example 9: Combination Treatment of *P. aeruginosa* Infection Using Anti-Psl Antibodies with Antibiotics Survival Improvement in Mouse Intraperitoneal Infection Model by Anti-Psl Antibodies in Combination with Antibiotics The ability of the anti-Psl antibody 3F12 and combination treatment of 3F12 with antibiotics Meropenem, Tobramycin, or Ciprofloxacin to improve survival in mouse intraperitoneal infection model was evaluated. HIV-10E8 was used as a negative control.

7-8 weeks old BALB/c mice (Vital River Laboratory) were intraperitoneally injected with antibody 24h before infection or with antibiotic 2h post infection. Specifically, the mice were administered with either anti-Psl antibody 3F12 (at 7 mg/kg), Meropenem (at 8 mg/kg), Tobramycin (at 2 mg/kg), Ciprofloxacin (at 2 mg/kg). For combination treatment, the mice were intraperitoneally injected with antibody 3F12 (at 7 mg/kg) 24h before infection and with Meropenem (at 8 mg/kg), Tobramycin (at 2 mg/kg) or Ciprofloxacin (at 2 mg/kg) 2h post infection, respectively. To induce intraperitoneal infection, the BALB/c mice were intraperitoneally inoculated with *P. aeruginosa* (57/66 strain) at triple the lethal dose ($3 \times LD90 = 7 \times 10^5$ CFU). Mouse survival was recorded for up to 5 days post-infection.

Figure 11:
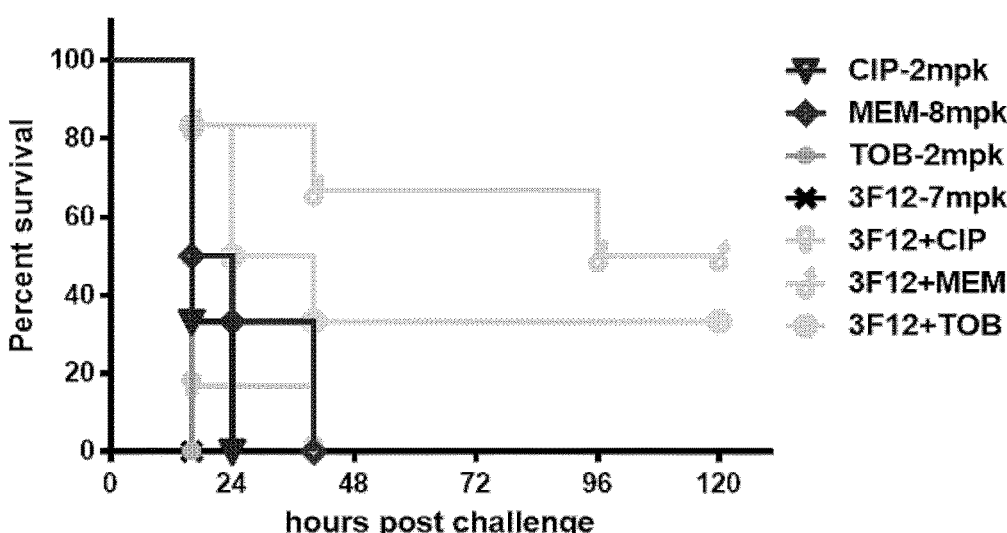
FIG. 11 shows the ability of the anti-Psl antibody 3F12 to improve survival in a mouse intraperitoneal infection model, alone or combined with antibiotics Meropenem (MEM), Tobramycin (TOB), or Ciprofloxacin (CIP).

As shown in FIG. 11, at triple the lethal dose ($3 \times LD_{90}$) of *P. aeruginosa* (57/66 strain) inoculation, the combination of 3F12 (at 7 mg/kg) with antibiotics Meropenem (at 8 mg/kg), Tobramycin (at 2 mg/kg) or Ciprofloxacin (at 2 mg/kg) exhibited enhanced survival improvement as compared to either the antibody treatment alone or the respective antibiotics treatment alone (p<0.05). These results here demonstrated the clinical potential of the use of the anti-Psl antibodies disclosed herein combined with antibiotics in neutralizing *P. aeruginosa*.

Example 10: Pharmacokinetic Profile of Anti-Psl Antibodies and Variants

To investigate the in vivo pharmacokinetics of the anti-Psl antibody 3F12, variants 7H9-m23 and P59-m21 as compared to the reference antibody psl0096, the plasma levels of 3F12, 7H9-m23, P59-m21, and the reference antibody psl0096 in rats were measured over time.

Pharmacokinetic profile in rats: 20 healthy adult rats with similar weight (about 0.2 kg by weight) were injected intravenously with 3 mg/kg of 3F12, 7H9-m23, P59-m21, or psl0096, respectively. Blood was collected at one hour after injection, and subsequently at 0 hour, 0.5 hour, 2 hours, 8 hours, 1 day, 3 days, 7 days, 11 days, 17 days, 23 days, 31 days, and 35 days after injection. After centrifugation, the plasma was used for analyzing antibody concentration using ELISA. For the ELISA experiment, Psl polysaccharide was used to coat the wells of a 96-well plate. On the following day, after washing with PBST, blocking with 200 μL PBS-milk for an hour, and another wash with PBST, the plasma was added and incubated for an hour at 37° C. The plate was washed with 0.1% TBST 6 times before 100 μL of Goat-anti-human Fc antibody-AP (1:3000 in PBS) was added to each well and incubated for an hour. After washing with 0.1% TBST 6 times, 50 μL of pNPP was added to each well and a colorimetric signal generated by the antibody-linked alkaline phosphatase was developed for 10-20 minutes at 37° C. The colorimetric signals were read by a microplate reader at 410 nm.

Figure 12:
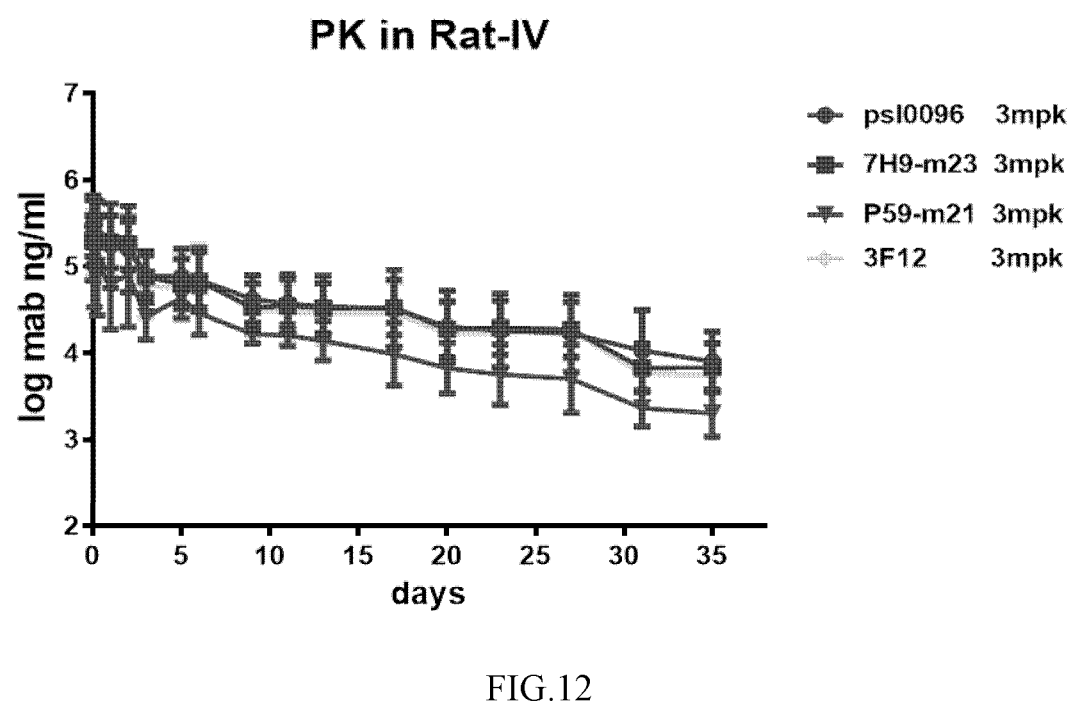

As shown in FIG. 12, the half-lives of 3F12, 7H9-m23, and P59-m21 at the tested i.v. dosage (3 mg/kg) was comparable to that of the reference antibody psl0096, indicating that the anti-Psl antibodies and variants displayed stable pharmacokinetic profiles which are comparable to the reference antibody psl0096.

---

The invention claimed is:

1. An isolated antibody or antigen binding fragment thereof which specially binds to *Pseudomonas* Psl, comprises:

a V$_H$ comprising an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 24; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(ii) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 171; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(iii) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 172; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(iv) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 173; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(v) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 36; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(vi) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 174; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(vii) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 175; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(viii) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 176; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(ix) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 177; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(x) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 178; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(xi) a V$_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 179; and a V$_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(xii) a $V_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 180; and a $V_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(xiii) a $V_H$ comprising an HC-CDR1 comprising the amino acid sequence of SEQ ID NO: 1, an HC-CDR2 comprising the amino acid sequence of SEQ ID NO: 13, and an HC-CDR3 comprising the amino acid sequence of SEQ ID NO: 181; and a $V_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(xiv) a $V_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 182; and a $V_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62;

(xv) a $V_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 185; and a $V_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62; or (xvi) a $V_H$ comprising an HC-CDR1 comprising the amino acid sequence of SEQ ID NO: 1, an HC-CDR2 comprising the amino acid sequence of SEQ ID NO: 163, and an HC-CDR3 comprising the amino acid sequence of SEQ ID NO: 186; and a $V_L$ comprising an LC-CDR1 comprising the amino acid sequence of SEQ ID NO: 37, an LC-CDR2 comprising the amino acid sequence of SEQ ID NO: 51, and an LC-CDR3 comprising the amino acid sequence of SEQ ID NO: 62.

2. The isolated antibody or antigen binding fragment thereof which specially binds to *Pseudomonas* Psl of claim 1, comprises:

(i) a $V_H$ comprising the amino acid sequence of SEQ ID NOs: 79 or a variant thereof having at least about 90% sequence identity to the amino acid sequence of SEQ ID NO:79, and a $V_L$ comprising the amino acid sequence of SEQ ID NO: 91 or a variant thereof having at least about 90% sequence identity to the amino acid sequence of SEQ ID NO:91; or (ii) a $V_H$ comprising the amino acid sequence of any one of SEQ ID NOs: 129-139, SEQ ID NOs: 149, 151, and SEQ ID NOs: 154-155 or a variant thereof having at least about 90% sequence identity to the amino acid sequence of any one of SEQ ID NOs: 129-139, SEQ ID NOs: 149, 151, and SEQ ID NOs: 154-155, and a $V_L$ comprising the amino acid sequence of SEQ ID NO: 91 or a variant thereof having at least about 90% sequence identity to the amino acid sequence of SEQ ID NO: 91.

3. The isolated antibody or antigen binding fragment thereof which specially binds to *Pseudomonas* Psl according to claim 1, wherein i) the antibody or antigen binding fragment comprises an Fc fragment; and/or ii) the antibody or antigen binding fragment is a full-length IgG antibody; and/or iii) the antibody or antigen binding fragment is chimeric, human, or humanized; and/or iv) the antibody or antigen binding fragment is selected from the group consisting of a Fab, a Fab', a F (ab)'2, a Fab'-SH, a single-chain Fv (scFv), an Fv fragment, and a diabody.

4. The isolated antibody or antigen binding fragment thereof which specially binds to *Pseudomonas* Psl of claim 3, wherein the antibody or antigen binding fragment is a full-length IgG1 or IgG4 antibody.

5. An isolated nucleic acid molecule that encodes the isolated antibody or antigen binding fragment thereof which specially binds to *Pseudomonas* Psl according to claim 1.

6. A vector comprising the nucleic acid molecule of claim 5.

7. An isolated host cell comprising the isolated antibody or antigen binding fragment of claim 6.

8. A method of producing an isolated antibody or antigen binding fragment thereof which specially binds to *Pseudomonas* Psl, comprising:

a) culturing the host cell of claim 7 under conditions effective to express the anti-Psl antibody or antigen binding fragment; and b) obtaining the expressed anti-Psl antibody or antigen binding fragment from the host cell.

9. A pharmaceutical composition comprising the isolated antibody or antigen binding fragment thereof which specially binds to *Pseudomonas* Psl according to claim 1, and a pharmaceutically acceptable carrier.

* * * * *